(12) United States Patent
Morman et al.

(10) Patent No.: US 6,475,600 B1
(45) Date of Patent: *Nov. 5, 2002

(54) COMPOSITE MATERIAL HAVING STRETCH AND RECOVERY INCLUDING A LAYER OF AN ELASTIC MATERIAL AND A TRANSVERSELY EXTENSIBLE AND RETRACTABLE NECKED LAMINATE OF NON-ELASTIC SHEET LAYERS

(75) Inventors: Michael Tod Morman, Alpharetta, GA (US); Robert John Schwartz, Cumming, GA (US); Howard Martin Welch, Woodstock, GA (US); Patricia Hsiaoyin Hwang, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/461,162

(22) Filed: Dec. 14, 1999

Related U.S. Application Data

(60) Provisional application No. 60/113,551, filed on Dec. 23, 1998, provisional application No. 60/113,467, filed on Dec. 23, 1998, and provisional application No. 60/113,552, filed on Dec. 23, 1998.

(51) Int. Cl.$^7$ .............................. B32B 5/04; B32B 3/26; B32B 3/24

(52) U.S. Cl. ...................... 428/152; 428/141; 428/131; 428/137; 428/198; 428/219; 428/500; 442/401; 442/398; 442/328; 442/400; 442/394

(58) Field of Search ............................... 428/152, 141, 428/131, 137, 198, 219, 500; 442/394, 400, 401, 398, 328

(56) References Cited

U.S. PATENT DOCUMENTS

| 3,341,394 A | 9/1967 | Kinney ..................... 161/72 |
| 3,679,538 A | 7/1972 | Druin et al. ................ 161/159 |
| 3,843,761 A | 10/1974 | Bierenbaum et al. ....... 264/210 |
| 4,110,392 A | 8/1978 | Yamazaki ................... 264/127 |
| 4,443,511 A | 4/1984 | Worden et al. ............. 428/198 |

(List continued on next page.)

FOREIGN PATENT DOCUMENTS

| EP | 0 321 985 | 6/1989 | ............. A61F/5/44 |
| EP | 0 419 742 | 4/1991 | ........... B32B/25/08 |
| EP | 0604731 A1 | 7/1994 | |
| EP | 0688263 B1 | 7/1998 | |
| WO | 91/15365 | 10/1991 | ........... B32B/25/08 |
| WO | 93/14928 | 8/1993 | ............. B32B/3/30 |
| WO | WO-9702133 A * | 1/1997 | ............. B32B/3/28 |
| WO | 97/02378 | 1/1997 | ........... D04H/1/54 |
| WO | 98/29239 | 7/1998 | |

Primary Examiner—William P. Watkins, III
(74) Attorney, Agent, or Firm—Steven D. Flack

(57) ABSTRACT

The present invention is directed to a composite material and a process for making the material. The composite material may be breathable and is formed from at least one layer of an elastic material and a necked laminate of sheet layers. The sheet layers include at least one non-elastic neckable material laminated to at least one non-elastic film defining a longitudinal and transverse dimension wherein the laminate is extensible and retractable in at least one dimension without significantly reducing the breathability and/or liquid barrier properties of the film layer. This laminate extensibility and retractability is the result of striated rugosities in, for instance, the longitudinal dimension of the film layer which enables the necked laminate to have an amount of extensibility and retractability in the transverse dimension. A breathable laminate may be made by first partially stretching a filled non-elastic film layer, attaching a non-elastic neckable layer to form a laminate and then stretching the laminate to neck the laminate and lengthen the film to its desired fully stretched configuration. Attachment of at least one layer of an elastic material to the necked laminate further provides stretch and recovery in at least one dimension.

25 Claims, 37 Drawing Sheets

U.S. PATENT DOCUMENTS

| | | | |
|---|---|---|---|
| 4,457,254 A | 7/1984 | Hungerford | 118/34 |
| 4,596,738 A | 6/1986 | Metcalfe et al. | 428/308.4 |
| 4,640,859 A | 2/1987 | Hansen et al. | 428/105 |
| 4,655,760 A | 4/1987 | Morman et al. | 604/385 A |
| 4,663,220 A | 5/1987 | Wisneski et al. | 428/221 |
| 4,720,415 A | 1/1988 | Vander Wielen et al. | 428/152 |
| 4,758,239 A | 7/1988 | Yeo et al. | 604/366 |
| 4,789,699 A | 12/1988 | Kieffer et al. | 524/271 |
| 4,833,026 A | 5/1989 | Kausch | 428/315.5 |
| 4,833,172 A | 5/1989 | Schwarz et al. | 521/62 |
| 4,847,134 A * | 7/1989 | Fahrenkrug et al. | 156/163 |
| 4,892,779 A | 1/1990 | Leatherman et al. | 428/220 |
| 4,910,064 A * | 3/1990 | Sabee | 156/62.4 |
| 4,923,650 A | 5/1990 | Antoon, Jr. et al. | 264/41 |
| 4,965,122 A | 10/1990 | Morman | 428/225 |
| 4,975,469 A | 12/1990 | Jacoby et al. | 521/84.1 |
| 5,114,781 A | 5/1992 | Morman | 428/198 |
| 5,116,662 A | 5/1992 | Morman | 428/198 |
| 5,143,679 A | 9/1992 | Weber et al. | 264/288.8 |
| 5,226,992 A | 7/1993 | Morman | 156/62.4 |
| 5,238,618 A | 8/1993 | Kinzer | 264/41 |
| 5,244,482 A | 9/1993 | Hassenboehler et al. | 55/528 |
| 5,317,035 A | 5/1994 | Jacoby et al. | 521/143 |
| 5,336,545 A | 8/1994 | Morman | 428/152 |
| 5,385,775 A | 1/1995 | Wright | 428/284 |
| 5,462,708 A * | 10/1995 | Swenson et al. | 264/174.11 |
| 5,514,470 A | 5/1996 | Haffner et al. | 428/246 |
| 5,536,555 A * | 7/1996 | Zelazoski et al. | 128/849 |
| 5,594,070 A | 1/1997 | Jacoby et al. | 525/88 |
| 5,683,787 A | 11/1997 | Boich et al. | 428/198 |
| 5,695,868 A | 12/1997 | McCormack | 428/283 |
| 5,704,101 A * | 1/1998 | Majors et al. | 156/515 |
| 5,728,085 A | 3/1998 | Widlund et al. | 604/378 |
| 5,763,041 A | 6/1998 | Leak et al. | 428/100 |
| 5,773,374 A | 6/1998 | Wood et al. | 442/328 |
| 5,779,860 A | 7/1998 | Hollenberg et al. | 162/206 |
| 5,789,065 A | 8/1998 | Haffner et al. | 428/152 |
| 5,804,011 A | 9/1998 | Dutta et al. | 156/160 |
| 5,804,241 A | 9/1998 | Isohata | 426/415 |
| 5,851,937 A * | 12/1998 | Wu et al. | 156/229 |
| 5,885,908 A * | 3/1999 | Jaeger et al. | 442/1 |
| 5,914,084 A | 6/1999 | Benson et al. | 264/284 |
| 5,916,663 A | 6/1999 | Chappell et al. | 428/152 |
| 6,114,263 A * | 9/2000 | Benson et al. | 442/394 |

* cited by examiner

COMPOSITE MATERIAL HAVING STRETCH AND RECOVERY INCLUDING A LAYER OF AN ELASTIC MATERIAL AND A TRANSVERSELY EXTENSIBLE AND RETRACTABLE NECKED LAMINATE OF NON-ELASTIC SHEET LAYERS

This application claims priority from U.S. Provisional Applications Nos. 60/113,467, 60/113,551 and 60/113,552, all filed Dec. 23, 1998.

FIELD OF THE INVENTION

The present invention is directed to a composite material and a process for making the composite material. The composite material may be breathable and is formed from at least one non-elastic film layer, at least one non-elastic neckable material, and at least one layer of an elastic material. Sheet layers of at least one non-elastic neckable material laminated to at least one non-elastic film are combined to form a necked laminate defining longitudinal and transverse dimensions wherein the necked laminate is extensible and retractable in at least one dimension without significantly reducing the breathability and/or liquid barrier properties of the film layer. The necked laminate extensibility and retractability is the result of striated rugosities in, for instance, the longitudinal dimension of the film layer which enables the necked laminate to have an amount of extensibility and retractability in the transverse dimension. Addition of at least one layer of an elastic material to the necked laminate to form a composite material provides stretch and recovery which was not present in the necked laminate while still maintaining breathability and barrier properties.

BACKGROUND OF THE INVENTION

Composite materials of multiple sheet layers of, for instance, film and nonwoven web layers, are known to be useful in such articles as diapers, training pants, incontinence garments, mattress pads, wipers, feminine care products such as sanitary napkins, in medical applications such as surgical drapes, gowns and facemasks, articles of clothing or portions thereof including workwear and lab coats, and the like.

These composite materials are made such that the article can be produced with relatively low cost and are thus disposable after only one or a few uses. Much research and development continues, however, to achieve "cloth-like" visual and tactile qualities in these articles without sacrificing breathability and low cost, while also providing an article that is liquid-impermeable. In particular, one disadvantage of such articles is that the material used to make the article does not "give" like, for instance, a fabric made from cotton, which due to its fiber and yarn structure, has a natural ability to extend and retract. These properties are necessary to allow the article to conform to the user's body, thereby feeling and appearing to be more "cloth-like". Even when the article "gives" it may quickly lose its shape if it does not exhibit stretch and recovery. One known solution to this problem has been to use an elastomeric or elastic material to form, for instance, the film layer of a film/nonwoven laminate. If breathability is attained by stretching a filled elastic film to form micropores, there are problems associated with maintaining breathability of filled elastic films since the recovery of the elastic material after stretching generally closes or partially closes the micropores which had been created for breathability.

Layers of a nonwoven web have been necked (as defined below) prior to applying an elastomeric sheet made using an elastomeric polymer as described in, for instance, commonly assigned U.S. Pat. No. 5,336,545 to Morman. Necking of the nonwoven web allowed it to extend in the transverse direction, but it would not recover without attachment of the elastic sheet.

Prior art laminates made from non-elastic materials which were used as, for example, diaper outer cover would not stretch in all directions and still be breathable through a non-elastic microporous film. Further, the prior art laminates of non-elastic materials that have been used in waistband components in articles such as diapers, have been made to be more conformable by first stretching an elastic waistband, then attaching the laminate to the stretched waistband such that when the waistband retracts, it draws in the laminate. A problem with this design is that the laminate is difficult to gather or bunch and the resulting product has minimal extensibility and retractability. Such bunched laminates are also very difficult to fabricate, have a cheap appearance and are uncomfortable when in contact with the body.

The present invention avoids these and other difficulties by providing an inexpensive composite material of a non-elastic necked laminate and at one elastic material which achieves stretch and recovery without compromising other properties such as breathability, liquid barrier properties and strength.

SUMMARY OF THE INVENTION

The present invention is directed to a composite material and a process for making the material. The composite material may be breathable and is formed from at least one layer of an elastic material and a necked laminate of sheet layers. The sheet layers include at least one non-elastic neckable material laminated to at least one non-elastic film defining a longitudinal and transverse dimension wherein the laminate is extensible and retractable in at least one dimension without significantly reducing the breathability and/or liquid barrier properties of the film layer. This laminate extensibility and retractability is the result of striated rugosities in, for instance, the longitudinal dimension of the film layer which enables the necked laminate to have an amount of extensibility and retractability in the transverse dimension. A breathable laminate may be made by first partially stretching a filled non-elastic film layer, attaching a non-elastic neckable layer to form a laminate and then stretching the laminate to neck the laminate and lengthen the film to its desired fully stretched configuration. Attachment of at least one layer of an elastic material to the necked laminate further provides stretch and recovery in at least one dimension.

DETAILED DESCRIPTION OF THE INVENTION

Figure 1:
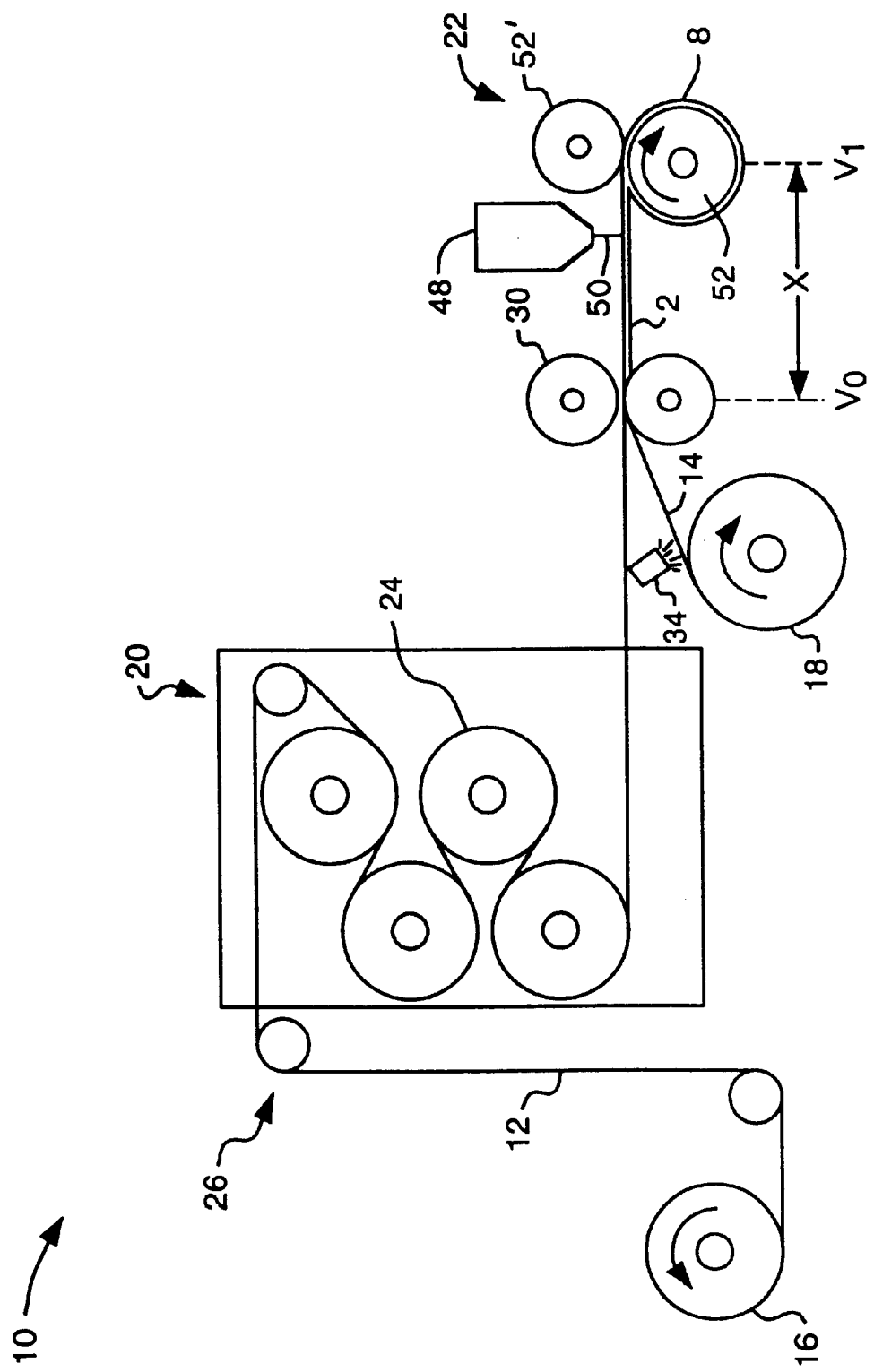
FIG. 1 is a schematic representation of an exemplary process for forming the composite material of the present invention.

The present invention is directed to a composite material which may be breathable and is formed from at least one non-elastic film layer, at least one non-elastic neckable material, and an elastic material. Sheet layers of at least one non-elastic neckable material laminated to at least one non-elastic film are combined to form a necked laminate, wherein the laminate defines longitudinal and transverse dimensions such that the laminate is extensible and retractable in at least one dimension without significantly reducing the breathability and/or liquid barrier properties of the film layer. This laminate extensibility and retractability is the result of striated rugosities in, for instance, the longitudinal dimension ("LD" as defined below) of the film layer which enable the necked laminate to have an amount of extensibility and retractability in the transverse dimension ("TD" as defined below). At least one layer of elastic material is attached to the necked laminate to form a composite material which is both stretchable and recoverable.

As contemplated herein, the elastic material may be present in the composite material in various forms. For instance, the elastic material may be in the form of an elastic non-neckable material, (such as a layer of an elastic meltblown nonwoven web), elastomeric filaments, (such as long, essentially continuous fibers as found in commonly assigned U.S. Pat. No. 5,385,775 to Wright), and the like.

If the elastic material is present in the composite material of the present invention as a layer of elastomeric filaments, these filaments may or may not be stretched in the longitudinal direction before attaching it to a necked laminate having extensibility and retractability in the transverse direction. When the elastomeric filaments are longitudinally stretched and attached while being stretched to the necked laminate along the TD of the necked laminate, the composite material exhibits stretch and recovery in the LD and extensibility and retractability in the TD. Further, the layer of elastomeric filaments may be attached lengthwise in the transverse dimension of the necked laminate, thereby providing TD stretch and recovery.

If the elastic material is present as an unstretched elastic material, the resulting composite material will exhibit TD stretch and recovery. The TD stretch is, however, limited by the extensibility of the necked laminate, because the inelastic film portion of the necked laminate does not actually stretch—instead the striated rugosities are essentially temporarily removed when a biasing force is applied in the transverse direction. If these striated rugosities are not permanently removed by, for instance, overextending the laminate in the transverse direction or heating the extended laminate to impart a "new" memory, then the laminate will tend to return to, or retract to, close to its original dimension.

If the elastic material is present as an elastic non-neckable material, it may be stretched and while being stretched, attached to the necked laminate to form a composite material which is both stretchable and recoverable in multiple directions. The elastic non-neckable material may, for instance, be stretched in the LD, and then attached to the necked laminate having extensibility and retractability in the TD. By addition of the longitudinally stretched elastic non-neckable material, LD stretch and recovery can be achieved which would complement the TD stretch and recovery found in the necked laminate and unstretched elastic non-neckable material. This composite material would not only stretch and recover in the LD and TD, but instead would have some stretch and recovery in all directions.

The necked laminate is made, for example, by first partially stretching the non-elastic film layer, attaching a non-elastic neckable layer to the film layer to form a laminate, and then stretching the laminate to neck the laminate and to complete the stretching/orientation of the film layer to its desired fully stretched configuration. A layer of elastomeric filaments may then be attached to the necked laminate to form the composite material. Alternatively, an elastic material may be stretched in the longitudinal direction and then attached to the necked laminate to form the composite material. As another alternative embodiment, an elastic material is attached, without first stretching, to the necked laminate to form the composite material. When a laminate is "fully stretched" it exhibits properties completely sufficient for the intended use, for example, breathability and tensile strength. As used herein, the term "partially stretched" means that the film and/or laminate is not fully stretched.

As used herein, the term "neck" or "neck stretch" interchangeably means that the laminate is drawn such that it is extended under conditions reducing its width or its transverse dimension by drawing and elongating to increase the length of the fabric. The controlled drawing may take place under cool temperatures, room temperature or greater temperatures and is limited to an increase in overall dimension in the direction being drawn up to the elongation required to break the laminate, which in many cases is about 1.2 to 1.6 times. When relaxed, the laminate does not retract toward its original longitudinal dimension or extend to its original transverse dimension, but instead essentially maintains its necked dimension. The necking process typically involves unwinding a sheet from a supply roll and passing it through a brake nip roll assembly driven at a given linear speed. A take-up roll or nip, operating at a linear speed higher than the brake nip roll, draws the fabric and generates the tension needed to elongate and neck the fabric. U.S. Pat. No. 4,965,122 issued to Morman, and commonly assigned to the assignee of the present invention, discloses a reversibly necked nonwoven material which may be formed by necking the material, then heating the necked material, followed by cooling and is incorporated herein by reference in its entirety. The heating of the necked material causes additional crystallization of the polymer giving it a partial heat set and some retraction.

As used herein, the term "neckable material or layer" means any material which can be necked such as a nonwoven, woven, or knitted material. As used herein, the term "necked material" refers to any material which has been drawn in at least one dimension, (e.g. lengthwise), reducing the opposite dimension, (e.g. width), such that when the drawing force is removed, the material can be pulled back to its original width. It should be understood that the term "neckable" describes the attribute of the material as being capable of being necked and does not require that the material actually be necked. The necked material has a higher basis weight per unit area than the un-necked material. When the necked material is pulled back to its original un-necked width, it should have about the same basis weight as the un-necked material. This differs from stretching/orienting the film layer, during which the film is thinned and the basis weight is reduced.

The term "laminate" as used herein means a combination made up of at least two sheet layers wherein at least one sheet layer is a non-elastic film layer and at least one sheet layer is a layer of non-elastic neckable material. Also, the term "longitudinal direction or LD" means the length of a material in the direction in which the material is moving when it is produced. The "longitudinal dimension" therefore, is the dimension of the longitudinal direction. The term "transverse direction or TD" means the width of the material, i.e. a direction generally perpendicular to the longitudinal direction. Likewise, the "transverse dimension" therefore, is the dimension of the transverse direction.

Referring to FIG. 1, there is schematically illustrated an exemplary process 10 for forming a composite material 8 according to the present invention. For all of the figures, like reference numerals represent the same or equivalent structure or element. A non-elastic film layer 12 is unwound from a first supply roll 16 and fed into a stretching means 20 using guide rollers 26. Once in the stretching means 20, the non-elastic film layer 12 is partially stretched in a longitudinal direction by stretching rollers 24 which stretch and thin the film layer 12. Such stretching usually occurs with little or no necking of the film layer. If the distance between the rolls is too large, irreversible narrowing of the film layer can occur. After partially stretching the film layer 12 and prior to laminating to the neckable material 14, the tension of the film layer 12 is only that which is sufficient to keep the layer from sagging or recovery. In other words, it is not necessary to continue stretching film layer 12 between the stretching means 20 and laminating means 30.

A non-elastic neckable material 14, likewise is unwound from second supply roll 18 which rotates in the direction of the arrows associated therewith. In an embodiment where partial film stretching is controlled to avoid film necking, matching the film width to the width of the neckable material is facilitated. It should be understood that the non-elastic neckable material and/or film layer may just as well be formed in-line rather than being pre-made and unwound.

Adhesive sprayer 34 applies adhesive to the surface of the neckable material 14 which is then laminated to the film layer 12 using laminating means 30 (e.g. nip rolls) to form the necked laminate. The laminate could also be formed by thermal point bonding, sonic welding, point bonding, or the like. The thus formed laminate 2 is then necked by a necking means 22 (e.g. take-up roll) which may be accomplished as shown in FIG. 1 wherein the surface speed $V_0$ of laminating means 30 is less than the surface speed $V_1$ of necking means 22. As used herein, to say that the laminate has been drawn 1X means that surface speed $V_0$ is equal to surface speed $V_1$. The "necking draw", therefore, is the surface speed $V_1$ divided by surface speed $V_0$. Further, the distance x between laminating means 30 and necking means 22, must be sufficient to allow for necking of the laminate, such that the transverse dimension of the laminate is less than that of the un-necked laminate. As a general rule, the distance x should be at least two times the transverse dimension (width) of the laminate. Such necking provides striated rugosities in the film and/or laminate resulting in transverse extensibility and retractability to the necked laminate 2 and more "cloth-like" aesthetics (e.g. the necked laminate is softer than prior art laminates and looks more like a woven material because of the striated rugosities).

Additionally, an elastic material forming apparatus 48, such as an apparatus conventionally used to form an elastic meltblown nonwoven web, such as that found in commonly assigned U.S. Pat. No. 4,663,220, to Wisneski et al., which is incorporated herein by reference in its entirety, is used to form the elastic material 50. The meltblown fibers are deposited onto the necked laminate 2 and may be sent through a pair of bonding rollers 52 and 52' to bond the layer of elastic material 50 to the necked laminate 2. Alternatively, a layer of long, essentially continuous elastomeric filaments 51 (which may be seen in FIG. 4), may be similarly attached to the necked laminate 2. As previously discussed, the elastic material may be attached in either a stretched or unstretched state, depending on the intended properties.

Figure 3:
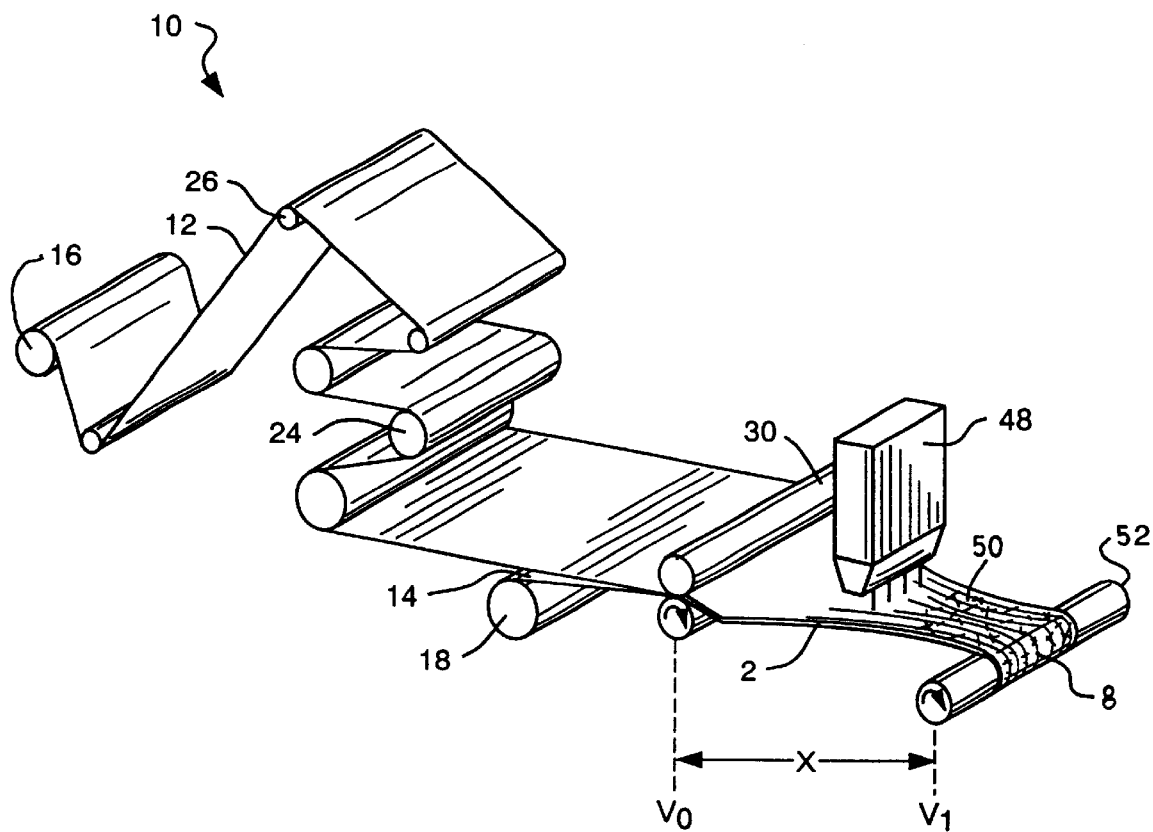
FIG. 3 is a perspective view of the process of FIG. 1 showing the stretching of the non-elastic film layer, attachment of the non-elastic neckable material, the necking of the laminate, and the attachment of the elastic material to form the composite material of the present invention.

As shown in FIG. 1, bonding rollers 52 and 52' rotate at speeds sufficient to perform the necking function as described above so that these have a dual function of bonding and necking in this illustration. Further, the composite material 8, is shown here as being wound onto the roll 52. Since the elastic material 50 may be sticky and therefore not easily unwound, the composite material 8 may just as easily be converted into an article in-line. FIG. 3 is essentially the same as FIG. 1 except that it is a perspective view and the upper bonding roller 52' has been removed since the bonding roller may not be necessary to bond the layer of elastic material 50 to necked laminate 2. In other words, the layer of elastic material 50 may be essentially melted onto the necked laminate 2.

Figure 13:
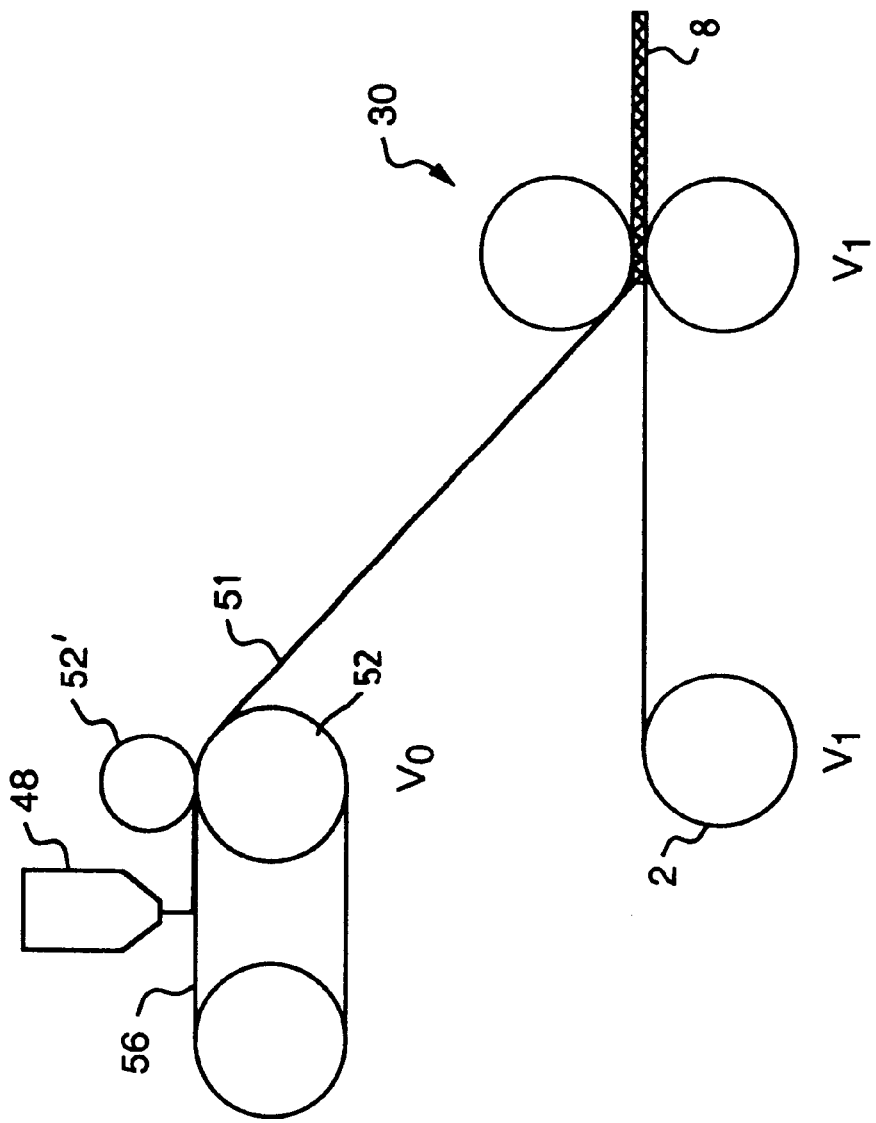
FIG. 13 is a schematic representation of an exemplary process for forming the composite material of the present invention having a stretched layer of elastomeric filaments.

Referring to FIG. 13, an elastic material forming apparatus 48 in this case is used to form the substantially parallel rows of elastomeric filaments 51. The long, essentially continuous elastomeric filaments are deposited onto the forming wire 56. The layer of elastomeric filaments 51 is stretched while bonding to the necked laminate 2 by the same means as described above for the necking means. The surface speed $V_0$ of bonding rollers 52 is less than the surface speed $V_1$ of laminating means 30 such that the layer of elastomeric filaments 51 is being stretched while being laminated to necked material 2. The tension of the stretched elastomeric filaments 51 is, therefore, maintained while laminating to necked laminate 2. In this embodiment, the thus formed composite material 8 exhibits stretch and recovery in the LD and extensibility and retractability in the TD.

Figure 20:
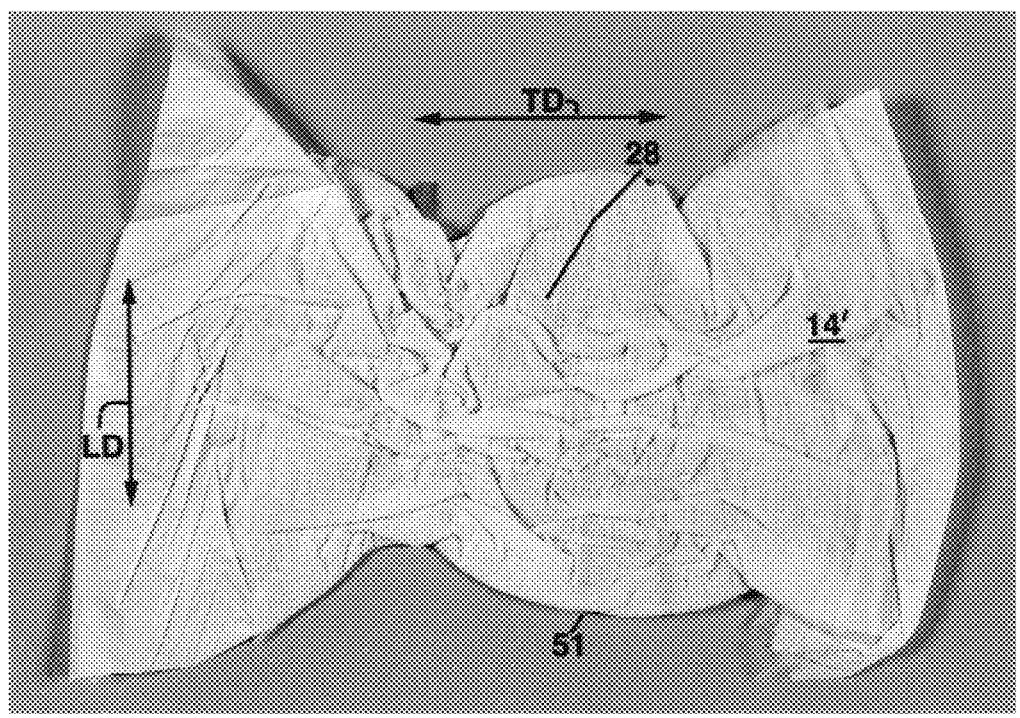
FIG. 20 is a top plan view of an image of the non-elastic neckable material side of the necked laminate which makes up the composite material of the present invention.
Figure 21:
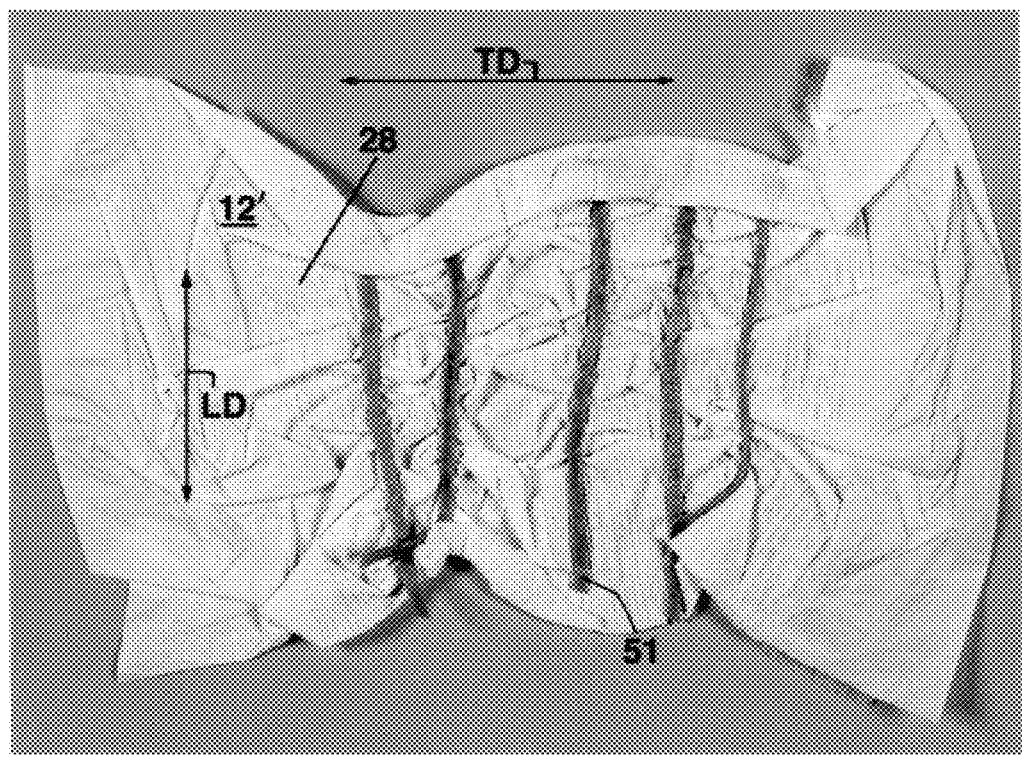
FIG. 21 is the opposite side of FIG. 20, showing the layer of elastomeric filaments which were stretched in the LD while being attached to the longitudinal dimension of the non-elastic film side of the necked laminate.
Figure 22:
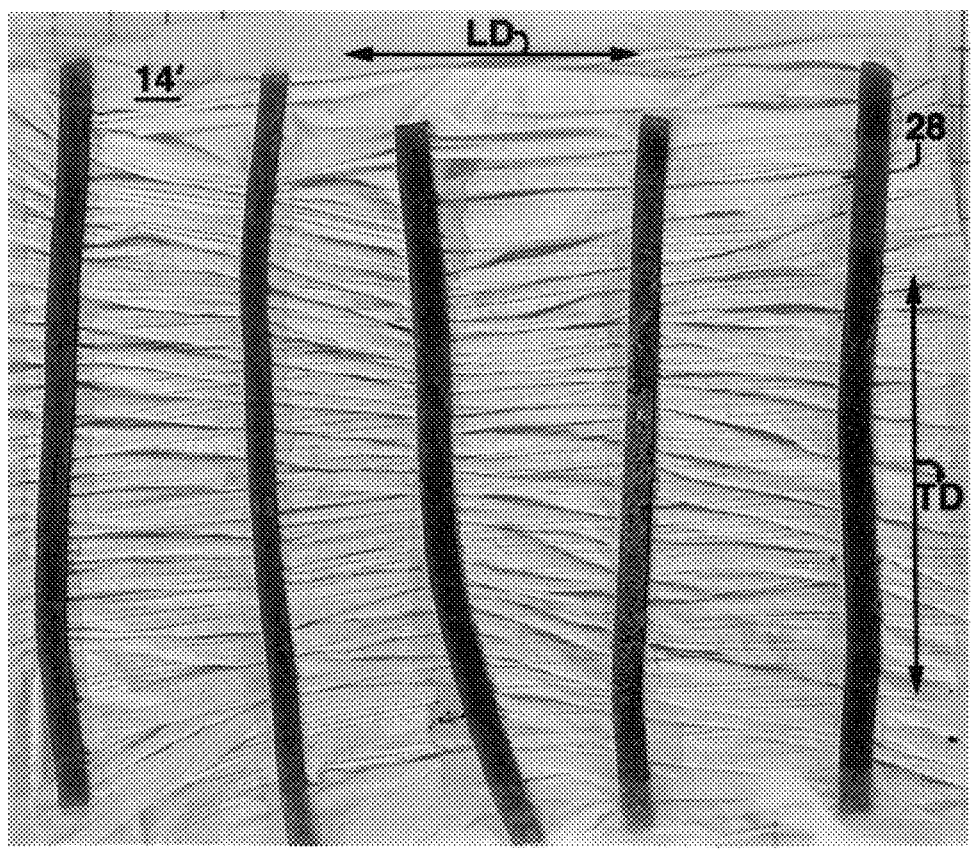
FIG. 22 is a top plan view of an image of the non-elastic neckable material side of the necked laminate which makes up the composite material of the present invention, showing the layer of elastomeric filaments which were lengthwise attached to the TD of the non-elastic film side of the necked laminate.
Figure 23:
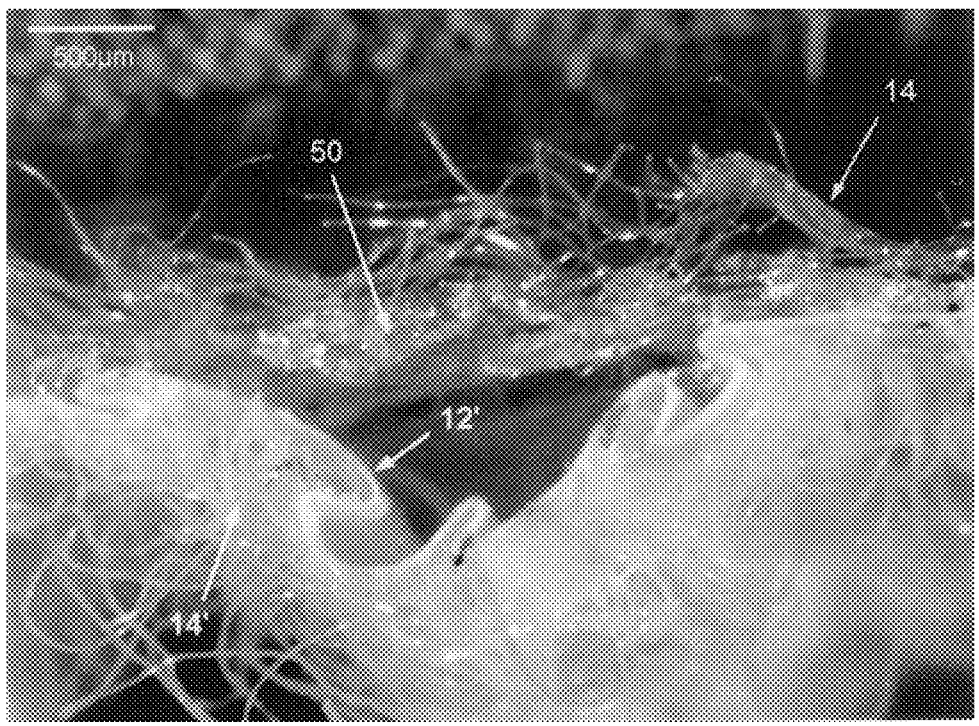
FIG. 23 is a cross-sectional optical photomicrograph of the composite material, in this case using an unstretched elastic meltblown nonwoven web to form the elastic material layer according to the present invention.
Figure 24:
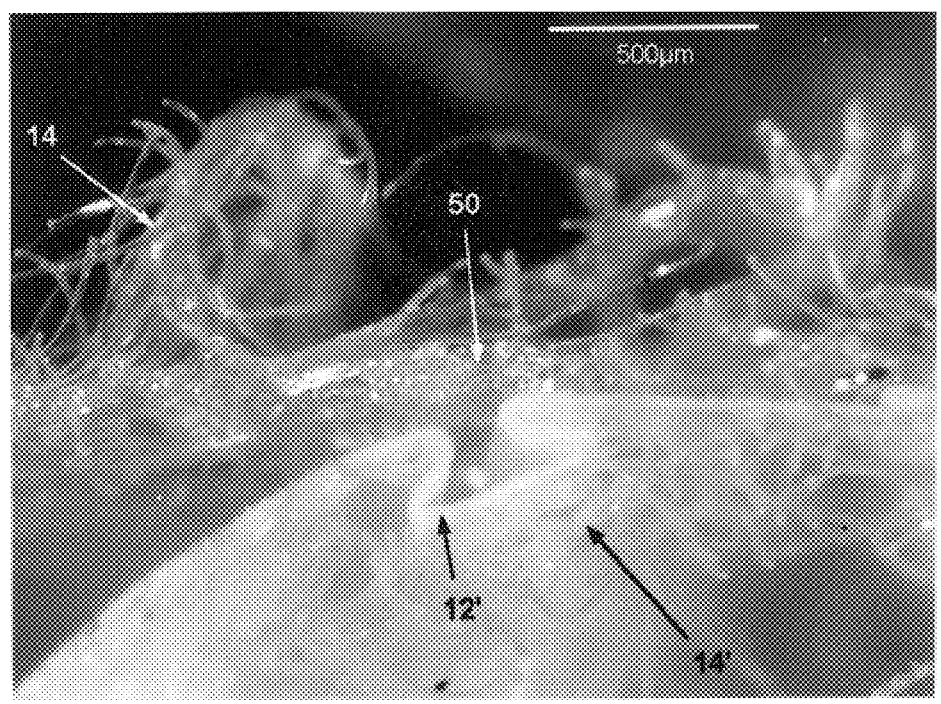
FIG. 24 is a cross-sectional optical photomicrograph of the composite material, in this case using an unstretched elastic meltblown nonwoven web to form the elastic material layer according to the present invention.

Now referring to FIG. 20, a top plan view is shown of an image of the non-elastic neckable material 14' side of the necked laminate 2 which makes up the composite material 8 of the present invention. Striated rugosities can be seen in the LD at 28. FIG. 21 is the opposite side of FIG. 20, showing the layer of elastomeric filaments 51 which were stretched in the LD while being attached to the longitudinal dimension of the non-elastic film 12' side of the necked laminate 2. FIG. 22 is a top plan view of an image of the non-elastic neckable material 14' side of the necked laminate 2 which makes up the composite material 8 of the present invention, showing the layer of elastomeric filaments 51 which were lengthwise attached to the TD of the non-elastic film 12' side of the necked laminate 2.

Figure 2:
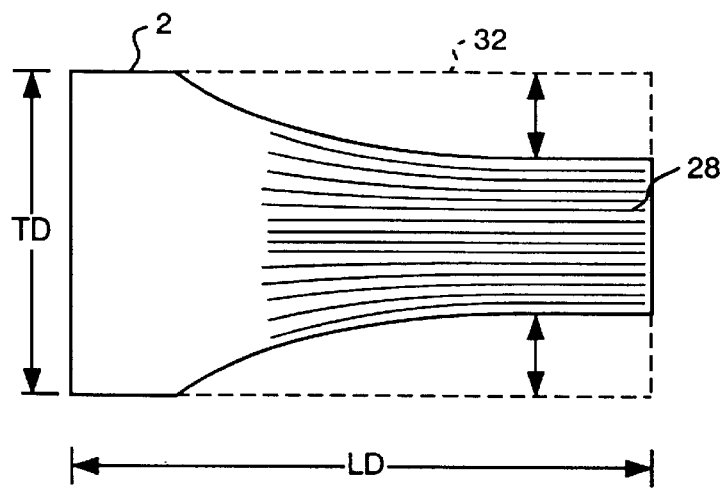
FIG. 2 is a top plan view of the laminate that forms the composite material of the present invention as it is being necked showing the striated rugosities in the longitudinal dimension.
Figure 6:
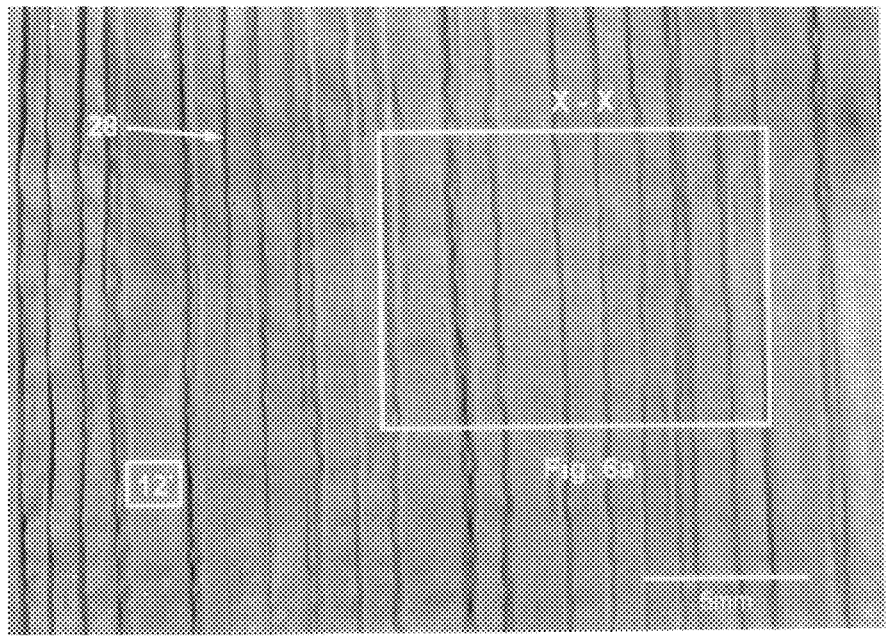
FIG. 6 is a top plan view of an optical photomicrograph (High Resolution Digital Image) of the non-elastic film layer side of the necked laminate that forms the composite material of the present invention showing the striated rugosities.
Figure 6A:
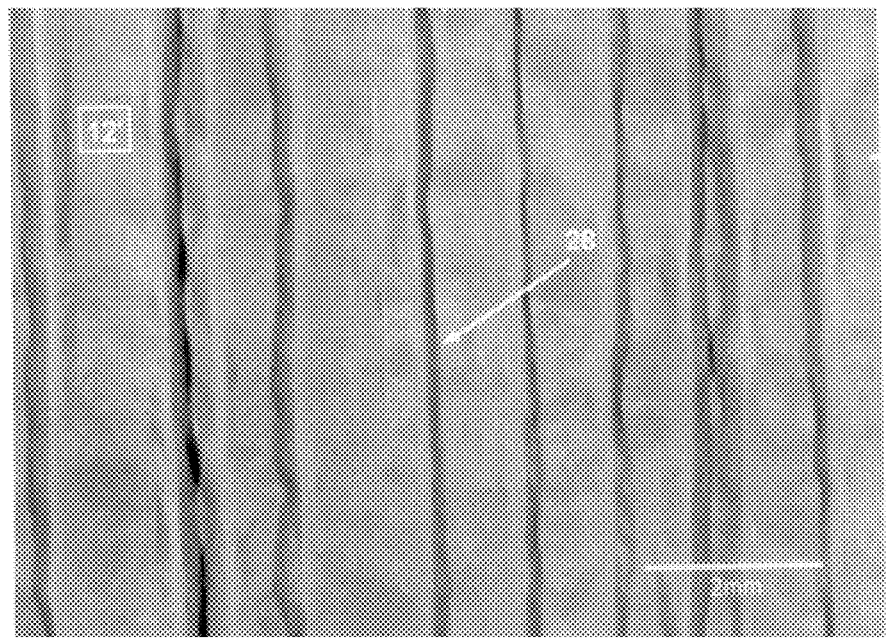
FIG. 6*a* is a top plan view of an optical photomicrograph of the enlarged section of FIG. 6 showing the variation and randomness of the striated rugosities.
Figure 7:
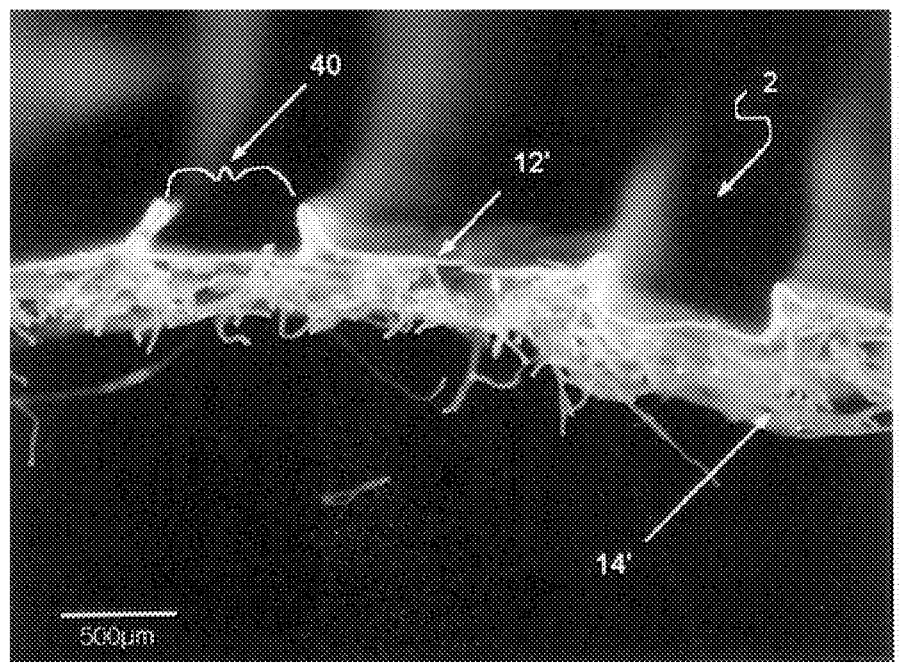
FIGS. 7, 8, and 9 are cross-sectional optical photomicrographs of a laminate that forms the composite material of the present invention showing trapezoidal, pleated, and crenellated striations, respectively.
Figure 8:
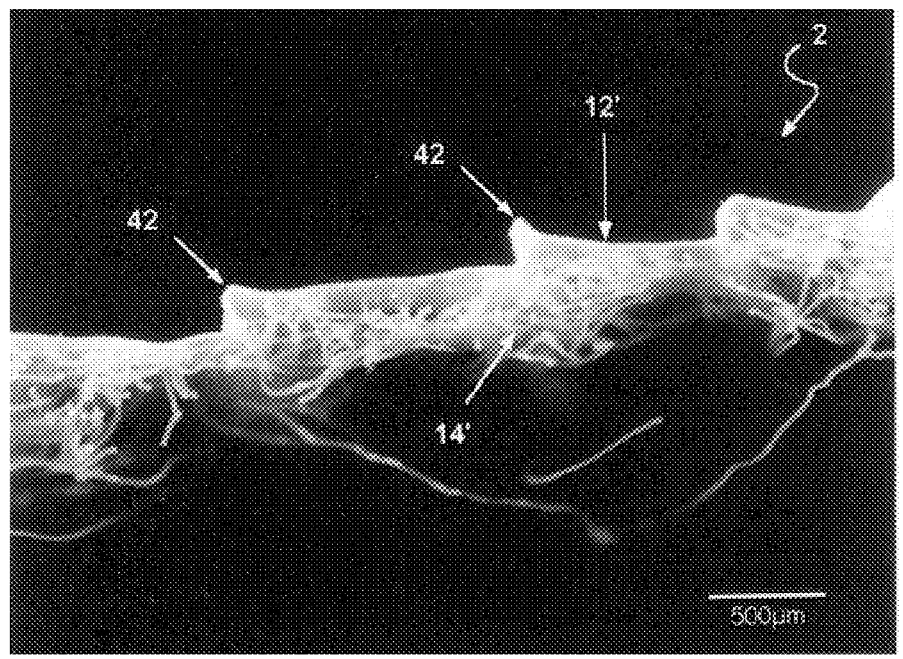
Figure 9:
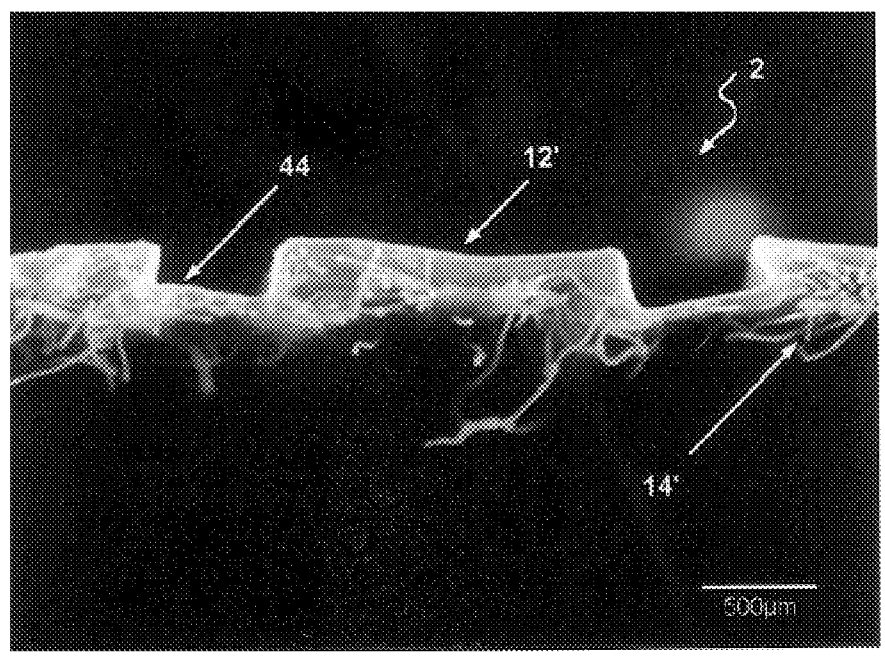

It is known that stretching and orienting a filled film layer causes micropores to form in the film, but longitudinal striated rugosities do not typically form in the film layer when stretched. The film layer would instead become physically thinner and may narrow slightly. Further, to then attempt to elongate the oriented filled film layer in the TD could result in tearing when very little force is applied, which is likely due to tearing along the LD microslits which have formed from stretching and orienting the filled film layer. The polymer used to make the film, the amount of filler, and how much the film was totally drawn affects how much the film can be TD extended before it splits. By necking the laminate, the non-elastic neckable material, which is attached to the non-elastic film layer, will neck and bring the non-elastic film layer with it, thereby forming the longitudinal striated rugosities in the film which allow the film layer to extend and retract in the TD without adversely affecting the breathability and/or barrier properties of the film. In FIG. 2, the striated rugosities 28 are shown figuratively in the longitudinal direction LD of laminate 2 which has been necked in the transverse direction TD. The un-necked transverse dimension 32 is the dimension the laminate would have but for the necking. The double edged arrows indicate the extensibility and retractability of the laminate in the TD. As used herein, the term "striated rugosities" refers to thin, narrow groved, or channeled wrinkles in the non-elastic film layer 12 of necked laminate 2. Referring to FIG. 6, the striated rugosities can be shown generally at 28 in the surface of film layer 12' of sample 6 (in the Examples below). FIG. 6a is an enlarged view of FIG. 6. As can be seen in these figures, the striated rugosities have a variable and random pattern. FIGS. 7–9 are enlarged cross-sectional end views of the laminate 2 of FIG. 6 at different points along the section showing the variable striations in film layer 12' which is attached to neckable material 14'. FIG. 7 generally shows a trapezoidal striation 40; FIG. 8 generally shows pleats 42; while FIG. 9 generally shows crenellated striations 44. As used herein, the term "crenellated" is used as in crenellated molding which, according to Webster's Third New International Dictionary, unabridged, copyright 1986, is "a molding of . . . [an] indented pattern common in medieval buildings". The striated rugosities actually occur predominantly in the non-elastic film layer, but can be seen through the necked material and give the entire laminate a more cloth-like appearance. If one were to delaminate the film layer from the neckable material after necking, the film layer would visually retain the striated rugosities while the neckable material would not. The separated film would extend and retract in the TD much like an accordian. A theory that may be ascribed to this phenomena is that the film actually crystallizes and/or plastically deforms to some degree when forming the striated rugosities, thereby setting a "memory" into the film which works to retract the laminate once it has been extended.

By the term "non-elastic", what is meant is that the sheet layers are made from polymers that are generally considered to be inelastic. In other words, use of such inelastic polymers to form the sheet layers would result in sheet layers which are not elastic. As used herein, the term "elastic" means any material which, upon application of a biasing force, is stretchable, that is, elongatable, at least about 60 percent (i.e., to a stretched, biased length which is at least about 160 percent of its relaxed unbiased length), and which will immediately recover at least 55 percent of its elongation upon release of the stretching, elongating force. By "immediately" what is meant is that the elastic material will behave, for instance, as a rubber band to recover as soon as the elongating force is removed. A hypothetical example would be a one (1) inch sample of a material which is elongatable to at least 1.60 inches (4.06 cm) and which upon being elongated to 1.60 inches (4.06 cm) and released, will immediately, i.e. within less than one second, recover to a length of not more than 1.27 inches (3.23 cm). Many elastic materials may be elongated by much more than 60 percent, for example, 100 percent or more, and many of these will recover to substantially their initial relaxed length, for example, to within 105 percent of their initial relaxed length upon release of the stretching force.

The terms "extensible and retractable" have been chosen to describe what the laminate made of non-elastic sheet layers of the present invention does upon application and removal of a biasing force. For the novel necked laminates described herein, the materials used to form the sheet layers are not elastic and so the terminology chosen to describe the phenomena exhibited by the laminate upon application and removal of a biasing force is "extensible and retractable". Those having skill in the art of elastic materials have conventionally used the phraseology "stretch and recover" to describe what an elastic material does upon application and removal of a biasing force as described above. As used herein, the terms "recover" and "recovery" refer to the immediate contraction of the stretched elastic material upon termination of the biasing force following stretching of the material by application of the biasing force.

As used herein, the term "polymer" generally includes, but is not limited to, homopolymers, copolymers, for example, block, graft, random and alternating copolymers, terpolymers, etc. and blends and modifications thereof. Such blends include blends of inelastic polymers with elastic polymers as long as the elastic polymers are used in such a quantity and composition that the use of these would not render the polymer elastic. Unless otherwise specifically limited, the term "polymer" shall include all possible geometrical configurations of the molecule. These configurations include, but are not limited to, isotactic, syndiotactic and random symmetries.

The non-elastic film layer 12 can be made from either cast or blown film equipment, can be coextruded and can be embossed if so desired. The film layer may be made from any suitable non-elastic polymer composition.

Such polymers include but are not limited to non-elastic extrudable polymers such as polyolefin or a blend of polyolefins, nylon, polyester, and ethylene vinyl alcohol. More particularly, useful polyolefins include polypropylene and polyethylene. Other useful polymers include those described in U.S. Pat. No. 4,777,073 to Sheth, assigned to Exxon Chemical Patents Inc., such as a copolymer of polypropylene and low density polyethylene or linear low density polyethylene.

Other useful polymers include those referred to as single site catalyzed polymers such as "metallocene" polymers produced according to a metallocene process and which have limited elastic properties. The term "metallocene-catalyzed polymers" as used herein includes those polymer materials that are produced by the polymerization of at least ethylene using metallocenes or constrained geometry catalysts, a class of organometallic complexes, as catalysts. For example, a common metallocene is ferrocene, a complex metal between two cyclopentadienyl (Cp) ligands. Metallocene process catalysts include bis(n-butylcyclopentadienyl)titanium dichloride, bis(n-butylcyclopentadienyl)zirconium dichloride, bis (cyclopentadienyl)scandium chloride, bis(indenyl) zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl (cyclopentadienyl,-1-flourenyl)zirconium dichloride, molybdocene dichloride, nickelocene, niobocene dichloride, ruthenocene, titanocene dichloride, zirconocene chloride hydride, zirconocene dichloride, among others. A more exhaustive list of such compounds is included in U.S. Pat. No. 5,374,696 to Rosen et al. and assigned to the Dow Chemical Company. Such compounds are also discussed in U.S. Pat. No. 5,064,802 to Stevens et al. and also assigned to Dow.

Such metallocene polymers are available from Exxon Chemical Company of Baytown, Tex. under the trade name EXXPOL® for polypropylene based polymers and EXACT® for polyethylene based polymers. Dow Chemical Company of Midland, Mich. has polymers commercially available under the name ENGAGE®. Preferably, the metallocene polymers are selected from copolymers of ethylene and 1-butene, copolymers of ethylene and 1-hexene, copolymers of ethylene and 1-octene and combinations thereof. For a more detailed description of the metallocene polymers and the process for producing same which are useful in the present invention, see commonly assigned U.S. patent application Ser. Nos. 774,852 abandoned and 854,658 abandoned first filed on Dec. 27, 1996 in the names of Gwaltney et al., each of which is incorporated herein by reference in its entirety. In general, the metallocene-derived ethylene-based polymers of the present invention have a density of at least 0.900 g/cc.

The non-elastic film layer may be a multi-layered film layer which may include a core layer, or "B" layer, and one or more skin layers, or "A" layers, on either side or both sides of the core layer. When more than one skin layer is present, is not a requirement that the skin layers be the same. For instance, there may be an A layer and an A' layer. Any of the polymers discussed above are suitable for use as a core layer of a multi-layered film. Any of the fillers disclosed herein are suitable for use in any film layer.

The skin layer will typically include extrudable thermoplastic polymers and/or additives which provide specialized properties to the non-elastic film layer. Thus, the skin layer may be made from polymers which provide such properties as antimicrobial, barrier, water vapor transmission, adhesion and/or antiblocking properties. The polymers are thus chosen for the particular attributes desired. Examples of possible polymers that may be used alone or in combination include homopolymers, copolymers and blends of polyolefins as well as ethylene vinyl acetate (EVA), ethylene ethyl acrylate (EEA), ethylene acrylic acid (EAA), ethylene methyl acrylate (EMA), ethylene butyl acrylate (EBA), polyester (PET), nylon (PA), ethylene vinyl alcohol (EVOH), polystyrene (PS), polyurethane (PU), and olefinic thermoplastic elastomers which are multistep reactor products wherein an amorphous ethylene propylene random copolymer is molecularly dispersed in a predominately semicrystalline high polypropylene monomer/low ethylene monomer continuous matrix. The skin layer can be formed of any semicrystalline or amorphous polymer, including one that is elastic. However, the skin layer is generally a polyolefin such as polyethylene, polypropylene, polybutylene or a ethylene-propylene copolymer, but may also be wholly or partly polyamide such as nylon, polyester such as polyethylene terephthalate, polyvinylidene fluoride, polyacrylate such as poly(methyl methacrylate)(only in blends) and the like, and blends thereof.

The non-elastic film layers in the laminate of the present invention can be made from breathable or non-breathable materials and can be apertured. The non-elastic film layer may contain such fillers as micropore developing fillers, e.g. calcium carbonate; opacifying agents, e.g. titanium dioxide; and antiblock additives, e.g. diatomaceous earth. Fillers may be incorporated for developing micropores during orientation of the non-elastic film layer resulting in breathable films. Once the particle-filled film has been formed, it is then either stretched or crushed to create pathways through the film layer. Generally, to qualify as being "breathable" for the present invention, the resultant laminate should have a water vapor transmission rate (WVTR) of at least about 250 g/m$^2$/24 hours as may be measured by a test method as described below. Preferably, the laminate will have a WVTR of at least about 1000 g/m$^2$/24 hours.

As used herein, a "micropore developing filler" is meant to include particulates and other forms of materials which can be added to the polymer and which will not chemically interfere with or adversely affect the extruded film but are able to be uniformly dispersed throughout the film layer. Generally, the micropore developing fillers will be in particulate form and usually will have somewhat of a spherical shape with average particle sizes in the range of about 0.5 to about 8 microns. The non-elastic film layer will usually contain at least about 20 volume percent, preferably about 20 to about 40 volume percent, of micropore developing filler based upon the total volume of the film layer. Both organic and inorganic micropore developing fillers are contemplated to be within the scope of the present invention provided that they do not interfere with the film formation process, the breathability of the resultant non-elastic film layer, the liquid barrier properties of the film layer or its ability to bond to another sheet layer.

Examples of micropore developing fillers include calcium carbonate ($CaCO_3$), various kinds of clay, silica ($SiO_2$), alumina, barium sulfate, sodium carbonate, talc, magnesium sulfate, titanium dioxide, zeolites, aluminum sulfate, cellulose-type powders, diatomaceous earth, magnesium sulfate, magnesium carbonate, barium carbonate, kaolin, mica, carbon, calcium oxide, magnesium oxide, aluminum hydroxide, pulp powder, wood powder, cellulose derivative, polymer particles, chitin and chitin derivatives. The micropore developing filler particles may optionally be coated with a fatty acid, such as stearic acid, or a larger chain fatty acid than starch such as behenic acid, which may facilitate the free flow of the particles (in bulk) and their ease of dispersion into the polymer matrix. Silica-containing fillers may also be present in an effective amount to provide antiblocking properties.

Also contemplated herein, is the attachment of an additional non-elastic neckable material which is not necked and which would most beneficially be attached to the unstretched elastic material, opposite of the necked laminate. Such an additional layer will provide a more pleasant appearance and feel to the other side of the composite material.

At least one layer of non-elastic neckable material is added to the composite material of the present invention. The non-elastic neckable material 14 (see, for instance, FIG. 1) includes nonwoven webs, woven materials and knitted materials which are air permeable.

As used herein, the term "nonwoven fabric or web" means a web having a structure of individual fibers or threads which are interlaid, but not in an identifiable manner as in a knitted fabric. Nonwoven fabrics or webs have been formed from many processes such as for example, bonded carded web processes, meltblowing processes and spunbonding processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91). The neckable material of the present invention has a basis weight of 5 to 90 gsm, preferably 10 to 90 gsm, more preferably 20 to 60 gsm.

Suitable fibers for forming the non-elastic neckable material include natural and synthetic fibers as well as bicomponent, multi-component, and shaped polymer fibers. A plurality of non-elastic neckable materials may also be used according to the present invention. Examples of such materials can include, for example, spunbond/meltblown composites and spunbond/meltblown/spunbond composites such as are taught in Brock et al., U.S. Pat. No. 4,041,203 which is incorporated herein by reference in its entirety. The non-elastic neckable materials may also be formed from "coform" as described in commonly assigned U.S. Pat. No. 4,100,324 to Anderson et al.

As used herein, the term "spunbonded fibers" refers to small diameter fibers which are formed by extruding through one or more extruders, attached to one or more banks made up of at least transfer piping and spinplates to produce molten thermoplastic material as filaments from a plurality of fine, usually circular, capillaries in a spinneret with the diameter of the extruded filaments then being rapidly reduced as by, for example, in Appel et al., U.S. Pat. No. 4,340,563; Matsuki, et al., U.S. Pat. No. 3,802,817; Dorschner et al., U.S. Pat. No. 3,692,618; Kinney, U.S. Pat. Nos. 3,338,992 and 3,341,394; Hartman, U.S. Pat. No. 3,502,763; and Dobo et al., U.S. Pat. No. 3,542,615. Spunbond fibers are generally not tacky when they are deposited onto a collecting surface. Spunbond fibers are generally continuous and have average diameters (from a sample of at least 10) larger than 7 microns, more frequently, between about 10 and 40 microns. The resulting matt of fibers is then bonded to form a strong neckable fabric. This bonding may be performed by ultrasonic bonding, chemical bonding, adhesive bonding, thermal bonding, needle punching, hydroentangling and the like.

As used herein the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, and are generally smaller than 20 microns in average diameter.

As used herein the term "microfibers" means small diameter fibers having an average diameter not greater than about 75 microns, for example, having an average diameter of from about 0.5 microns to about 50 microns, more particularly, from about 2 microns to about 40 microns. Another frequently used expression of fiber diameter is denier, which is defined as grams per 9000 meters of a fiber and may be calculated as fiber diameter (in microns) squared, multiplied by the polymer density in grams/cc, multiplied by 0.00707. For the same polymer, a lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2 \times 0.89 \times 0.00707 = 1.415$). Outside the United States the unit of measurement is more commonly the "tex", which is defined as the grams per kilometer of fiber. Tex may be calculated as denier/9.

The non-elastic neckable material is preferably formed from at least one member selected from fibers and filaments made of non-elastic polymers such as polyesters, for example, polyethylene terephthalate, polyolefins, for example, polyethylene and polypropylene, polyamides, for example, nylon 6 and nylon 66. These fibers or filaments are used alone or in a mixture of two or more thereof.

Many polyolefins are available for fiber production according to the present invention, for example, fiber forming polypropylenes include Exxon Chemical Company's Escorene® PD 3445 polypropylene and Himont Chemical Company's PF-304. Polyethylenes such as Dow Chemical's ASPUN® 6811A linear low density polyethylene, 2553

LLDPE and 25355 and 12350 high density polyethylene are also suitable polymers. The polyethylenes have melt flow rates of about 26, 40, 25 and 12 respectively. Many other polyolefins are commercially available.

If at least one layer of elastomeric filaments 51 is added to the composite material, these filaments may be formed by the method of forming substantially parallel rows of elastomeric filaments found in commonly assigned U.S. Pat. No. 5,385,775 to Wright which is incorporated herein by reference in its entirety. The elastomeric filaments may have an average diameter of at least about 40 microns (em), preferably ranging from at least about 40 to about 750 microns.

The layer of elastomeric filaments and/or the elastic material are preferably formed from at least one member selected from fibers and filaments made of elastic (or elastomeric) polymers which may be formed as described above for non-elastic neckable materials, for instance, into a nonwoven web of elastic fibers, e.g., meltblown elastic fibers. A useful layer of elastic material may have a basis weight ranging from about 5 gsm (grams per square meter) to about 300 gsm, for example, from about 5 gsm to about 150 gsm. Elastomeric thermoplastic polymers useful in the practice of this invention may be those made from block copolymers such as polyurethanes, copolyether esters, polyamide polyether block copolymers, ethylene vinyl acetates (EVA), block copolymers having the general formula A-B-A' or A-B like copoly(styrene/ethylene-butylene), styrene-poly(ethylene-propylene)-styrene, styrene-poly(ethylene-butylene)-styrene, (polystyrene/poly(ethylene-butylene)/polystyrene, poly(styrene/ethylene-butylene/styrene) and the like.

Useful elastomeric resins include block copolymers having the general formula A-B-A' or A-B, where A and A' are each a thermoplastic polymer endblock which contains a styrenic moiety such as a poly (vinyl arene) and where B is an elastomeric polymer midblock such as a conjugated diene or a lower alkene polymer. Block copolymers of the A-B-A' type can have different or the same thermoplastic block polymers for the A and A' blocks, and the present block copolymers are intended to embrace linear, branched and radial block copolymers. In this regard, the radial block copolymers may be designated (A-B)$_m$-X, wherein X is a polyfunctional atom or molecule and in which each (A-B)$_m$-radiates from X in a way that A is an endblock. In the radial block copolymer, X may be an organic or inorganic polyfunctional atom or molecule and m is an integer having the same value as the functional group originally present in X. It is usually at least 3, and is frequently 4 or 5, but not limited thereto. Thus, in the present invention, the expression "block copolymer", and particularly "A-B-A" and "A-B" block copolymer, is intended to embrace all block copolymers having such rubbery blocks and thermoplastic blocks as discussed above, which can be extruded (e.g., by meltblowing), and without limitation as to the number of blocks. The elastomeric nonwoven web may be formed from, for example, elastomeric (polystyrenelpoly(ethylene-butylene)/polystyrene) block copolymers. Commercial examples of such elastomeric copolymers are, for example, those known as KRATON® materials which are available from Shell Chemical Company of Houston, Tex. KRATON® block copolymers are available in several different formulations, a number of which are identified in U.S. Pat. Nos. 4,663,220 and 5,304,599, hereby incorporated by reference.

Polymers composed of an elastomeric A-B-A-B tetrablock copolymer may also be used in the practice of this invention. Such polymers are discussed in U.S. Pat. No. 5,332,613 to Taylor et al. In such polymers, A is a thermoplastic polymer block and B is an isoprene monomer unit hydrogenated to a poly(ethylene-propylene) monomer unit. An example of such a tetrablock copolymer is a styrene-poly(ethylene-propylene)-styrene-poly(ethylene-propylene) or SEPSEP elastomeric block copolymer available from the Shell Chemical Company of Houston, Tex. under the trade designation KRATON® G-1657.

Other exemplary elastomeric materials which may be used include polyurethane elastomeric materials such as, for example, those available under the trademark ESTANE® from B. F. Goodrich & Co. or MORTHANE® from Morton Thiokol Corp., polyetherester elastomeric materials such as, for example, those available under the trade designation HYTREL® from E. I. du Pont de Nemours and Company, Inc., and those known as ARNITEL®, formerly available from Akzo Plastics of Arnhem, Holland and now available from DSM of Sittard, Holland.

Another suitable material is a polyether block amide copolymer having the formula:

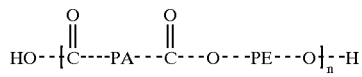

where n is a positive integer, PA represents a polyamide polymer segment and PE represents a polyether polymer segment. In particular, the polyether block amide copolymer has a melting point of from about 150° C. to about 170° C., as measured in accordance with ASTM D-789; a melt index of from about 6 grams per 10 minutes to about 25 grams per 10 minutes, as measured in accordance with ASTM D-1238, condition Q (235 C/1 Kg load); a modulus of elasticity in flexure of from about 20 Mpa to about 200 Mpa, as measured in accordance with ASTM D-790; a tensile strength at break of from about 29 Mpa to about 33 Mpa as measured in accordance with ASTM D-638 and an ultimate elongation at break of from about 500 percent to about 700 percent as measured by ASTM D-638. A particular embodiment of the polyether block amide copolymer has a melting point of about 152° C. as measured in accordance with ASTM D-789; a melt index of about 7 grams per 10 minutes, as measured in accordance with ASTM D-1238, condition Q (235 C/1 Kg load); a modulus of elasticity in flexure of about 29.50 Mpa, as measured in accordance with ASTM D-790; a tensile strength at break of about 29 Mpa, a measured in accordance with ASTM D-639; and an elongation at break of about 650 percent as measured in accordance with ASTM D-638. Such materials are available in various grades under the trade designation PEBAX® from Atochem Inc. Polymers Division (RILSAN®), of Glen Rock, N.J. Examples of the use of such polymers may be found in U.S. Pat. Nos. 4,724,184, 4,820,572 and 4,923,742 hereby incorporated by reference, to Killian et al. and assigned to the same assignee as this invention.

Elastomeric polymers also include copolymers of ethylene and at least one vinyl monomer such as, for example, vinyl acetates, unsaturated aliphatic monocarboxylic acids, and esters of such monocarboxylic acids. The elastomeric copolymers and formation of elastomeric nonwoven webs from those elastomeric copolymers are disclosed in, for example, U.S. Pat. No. 4,803,117.

The thermoplastic copolyester elastomers include copolyetheresters having the general formula:

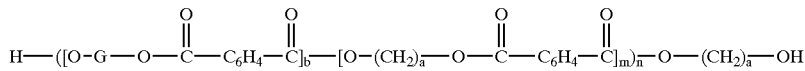

where "G" is selected from the group consisting of poly(oxyethylene)-alpha,omega-diol, poly(oxypropylene)-alpha,omega-diol, poly(oxytetramethylene)-alpha,omega-diol and "a" and "b" are positive integers including 2, 4 and 6, "m" and "n" are positive integers including 1–20. Such materials generally have an elongation at break of from about 600 percent to 750 percent when measured in accordance with ASTM D-638 and a melt point of from about 350° F. to about 400° F. (176 to 205° C.) when measured in accordance with ASTM D-2117.

Commercial examples of such copolyester materials are, for example, those known as ARNITEL®, formerly available from Akzo Plastics of Arnhem, Holland and now available from DSM of Sittard, Holland, or those known as HYTREL® which are available from E. I. du Pont de Nemours and Company, Inc., of Wilmington, Del. Formation of an elastomeric nonwoven web from polyester elastomeric materials is disclosed in, for example, U.S. Pat. No. 4,741,949 to Morman et al. and U.S. Pat. No. 4,707,398 to Boggs, hereby incorporated by reference.

A nonwoven web layer may be bonded to impart a discrete bond pattern with a prescribed bond surface area. This is known as thermal point bonding. "Thermal point bonding" involves passing a web of fibers to be bonded between a heated calender or patterned roll and an anvil roll. The calender roll is patterned so that the entire neckable material is not bonded across its entire surface. In fact, this feature is very important for necking of neckable materials as described herein. If too much bond area is present on the neckable material, it will break before it necks. If there is not enough bond area, then the neckable material will pull apart. Typically, the percent bonding area useful in the present invention ranges from around 5% to around 40% of the area of the neckable material. Many patterns for calender rolls have been developed. As will be understood by those skilled in the art, bond area percentages are, of necessity, described in approximations or ranges since bond pins are normally tapered and wear down over time. As those skilled in the art will also recognize, references to "pins/in.$^2$" and "bonds/in.$^2$" are somewhat interchangeable since the pins will create bonds in the substrate in essentially the same sizes and surface relationship as the pins on the roll. There are a number of discrete bond patterns which may be used. See, for example, Brock et al., U.S. Pat. No. 4,041,203. One example of a pattern has points and is the Hansen Pennings or "H&P" pattern with about 200 bonds/square inch as taught in U.S. Pat. No. 3,855,046 to Hansen and Pennings. The H&P pattern has square point or pin bonding areas wherein each pin may have a side dimension of 0.038 inches (0.965 mm), for example, resulting in a pattern having a bonded area of about 30%. Another typical point bonding pattern is the expanded Hansen and Pennings or "EHP" bond pattern which produces a bond area of about 15% to 18% which may have a square pin having a side dimension of 0.037 inches (0.94 mm), for example, and a pin density of about 100 pins/in$^2$. Another typical point bonding pattern designated "714" has square pin bonding areas wherein each pin may have a side dimension of 0.023 inches, for example, for a bond area of 15% to 20% and about 270 pins/in$^2$. Other common patterns include a "Ramisch" diamond pattern with repeating diamonds having a bond area of 8% to 14% and 52 pins/in.$^2$, a HDD pattern, which comprises point bonds having about 460 pins/in.$^2$ for a bond area of about 15% to about 23%, as well as a wire weave pattern looking as the name suggests, e.g. like a window screen and having a bond area of 15% to 20% and 302 bonds/in.$^2$. Another bond pattern for a spunbond facing web is a "S" weave pattern as described in commonly assigned U.S. Pat. No. 5,964,742 to McCormack et al., which is incorporated herein by reference in its entirety.

Laminating the non-elastic film layer to the non-elastic neckable material to form the necked laminate may occur by typical methods known in the art including adhesive bonding, point bonding, thermal point bonding and sonic welding. The use of inelastic and/or elastic adhesives for the adhesive bonding is also contemplated herein. As discussed in more detail below, the use of an elastic adhesive has not been found to significantly impact ease of extensibility. When the film layer and neckable material are bonded through the use of heat and/or pressure, laminating means 30 (FIG. 1) such as laminating rollers may be used. The laminating rollers may be heated and point bonding may be used. The temperature at which the laminating rollers are heated depends on the properties of the film and or neckable material but is usually in the range of 200–275° F. (93–135° C.). The laminating rollers may each be patterned or one roll may be smooth while the other roll is patterned. If one of the rolls is patterned it will create a discrete bond pattern with a prescribed bond surface area for the resultant necked laminate 2.

Figure 4:
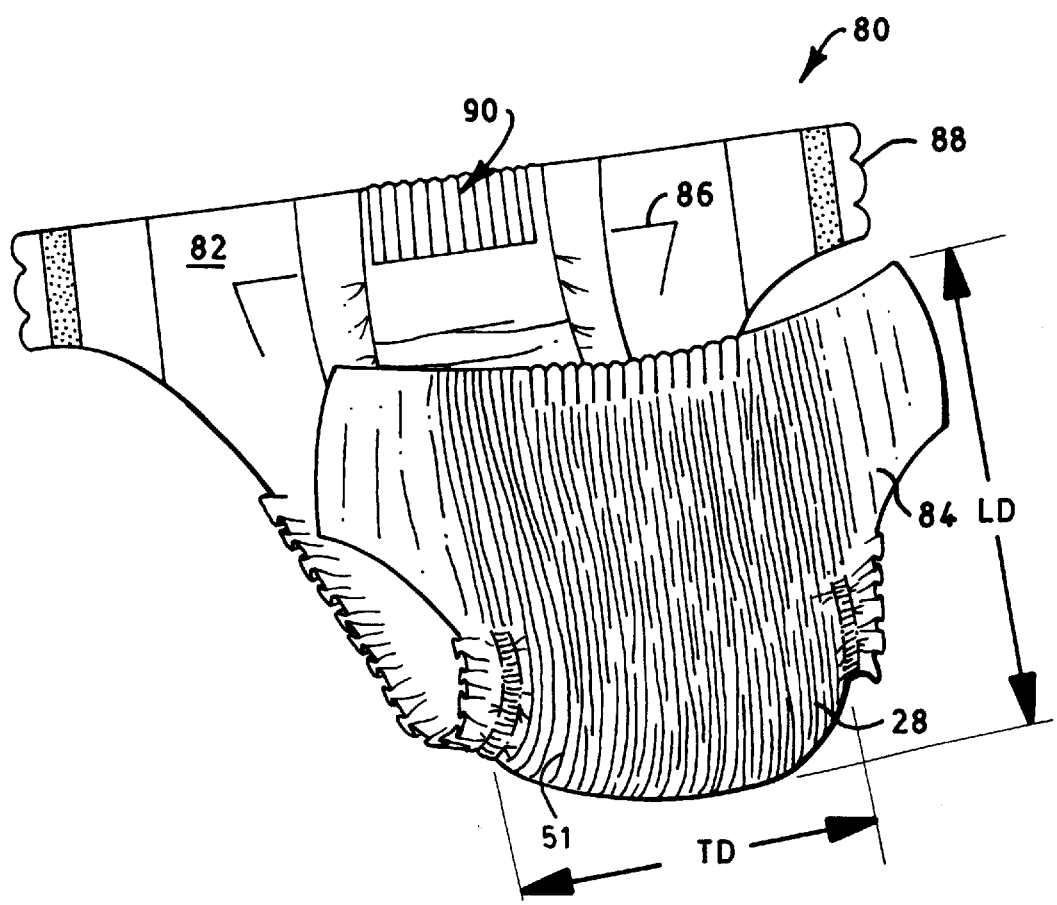
FIG. 4 is a partially cut-away top plan view of an exemplary personal care absorbent article, in this case a diaper, which may utilize the composite material according to the present invention.

As has been stated previously, the composite material having stretch and recovery may be used in a wide variety of applications, including personal care absorbent articles such as diapers, training pants, incontinence devices and feminine hygiene products such as sanitary napkins. An exemplary article 80, a diaper, is shown in FIG. 4. Referring to FIG. 4, most such personal care absorbent articles 80 include a liquid permeable top sheet or liner 82, a back sheet or outercover 84 and an absorbent core 86 disposed between and contained by the top sheet 82 and back sheet 84. Articles 80, such as diapers, may also include some type of fastening means 88 such as adhesive fastening tapes or mechanical hook and loop type fasteners to maintain the garment in place on the user.

The composite material may be used to form various portions of the article including, but not limited to, the top sheet 82 and the back sheet 84. If the composite material is to be used as the top sheet 82, it will most likely be apertured or otherwise made to be liquid permeable. When using the composite material as back sheet 84, it is usually advantageous to place the nonwoven side, if only one side has a nonwoven, facing out away from the user. In addition, in such embodiments it may be possible to utilize the nonwoven portion of the composite material as the loop portion of the hook and loop combination of fastening means 88.

Figure 5:
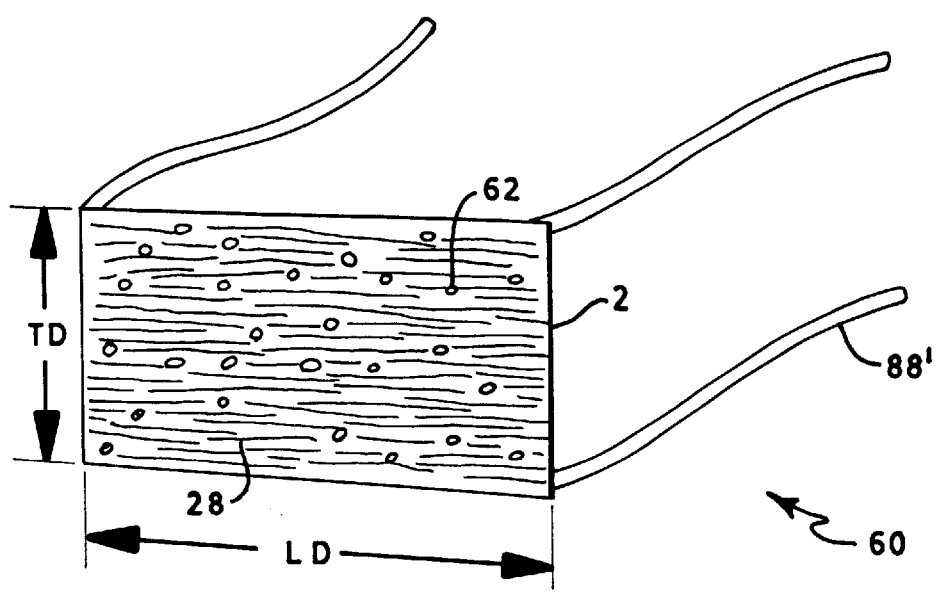
FIG. 5 is a plan view of an exemplary medical article, in this case a facemask, which may utilize the composite material according to the present invention.

As the composite material has stretch and recovery, the elastic waistband 90 can be attached/incorporated in a non-stretched configuration during diaper production, significantly simplifying the converting process. The resulting waistband will stretch, recover, and seal around the baby's waist much better. Composite materials of the present invention are equally useful in articles used in medical applications. Referring to FIG. 5, the composite material has been utilized to form an exemplary article useful in medical applications, in this case a facemask 60. The composite material is attached to fastening means 88' to tie the facemask 60 to the head of a user. In this application, the non-elastic film layer would most likely be apertured so that the wearer may breathe comfortably. Such apertures 62 will be sized and located such that breathing is not impaired but will not be too large or numerous such that the function of the facemask (e.g. to protect the wearer) is thwarted. One such embodiment may be to have the apertures on the TD edges of the facemask (not shown).

Yet another exemplary article is a protective garment such as a lab coat or workwear. One particularly bothersome aspect of use of the prior art non-elastic laminate is the lack of "give" as discussed above. This can be best understood in the context of bending a laminate-clad elbow. If the prior art laminate was used to create the garment, when the elbow bends, the material tightens around the elbow which may cause the material to tear or at the very least cause discomfort to the user. If the garment were to be made of the composite material of the present invention, however, the material will "give" when the elbow bends and afterwards tend to return to its prior form.

One advantage of using composite material in such applications is that the articles will be more "cloth-like" in both appearance and feel. Additionally, the stretch and recovery will allow the article to more closely conform to the body of the wearer.

The composite material of the present invention is able to maintain properties such as strength, hydrohead and breathability while getting improvements in "cloth-like" characteristics such as conformability and stretch and recovery. The advantages and other characteristics of the present invention are best illustrated by the following examples.

EXAMPLES

Samples of the present invention were prepared as described below. The samples were then subjected to the following tests:

Tensile Test: The tensile test measured strength and elongation or strain of a fabric when subjected to unidirectional stress according to ASTM Standard Test D 5034-95, as well as Federal Test Methods Standard No. 191A Method 5102-78. This test measured the strength in pounds and percent stretch while elongating the sample until it broke. Higher numbers indicate a stronger and/or more stretchable fabric, respectively. The term "peak load" means the maximum load or force, expressed in pounds, required to elongate a sample to break or rupture in a tensile test. The terms "elongation", "strain" or "percent stretch" means the increase in length of a sample during a tensile test expressed as a percentage. Values for peak load and strain at peak load were obtained using a width of fabric of 3×6 in. (76×152 mm), a 3 in. (76 mm) clamp width, a gauge length of 3 in. (76 mm), and a constant rate of extension of 12 inches/min. (305 mm/min.), where the entire sample width was gripped in the clamps. The specimen was clamped, for example, in an 1130 Instron, available from the Instron Corporation, or a Thwing-Albert Model INTELLECT II available from the Thwing-Albert Instrument Co., 10960 Dutton Rd., Philadelphia, Pa. 19154, and the unit was zeroed, balanced and calibrated according to the standard procedure.

Cycle Test: The samples were also cycled on the Instron tester with Microcon II using a 50 kg load cell. The sample sizes and tester were set up as described above except that the gage length was 2 inches (5.08 cm). Chart and crosshead speeds were set for 20 inches (50.8 cm) per minute. The maximum extension limit for the cycle length was set at a distance determined by calculating 50 percent of the "elongation to break" from the Tensile Test. The samples were cycled to the specified cycle length two times and then were taken to break on the third cycle. The test equipment was set to measure Peak Load in grams force for each cycle. On the third cycle (cycle to break), the Peak Elongation and Peak Load were measured.

% Permanent Set: The permanent set test measures the degree of retractability of a material after being stretched to a specific length. Generally, the greater the permanent set value, the less retractable the sample is. After the laminate was produced and wound onto a roll, indelible ink was used to mark a 2 in. (5.08 cm) wide strip of material in the transverse dimension. After the laminate was unwound, a sample area 3 in. (7.62 cm) (LD)×4.5 in. (11.43 cm) (TD) was cut out of the laminate to include the marked-off area. Each sample was placed between two 3 in. (7.62 cm) wide jaws. The jaws were separated a distance of 2 in. (5.08 cm) apart and the jaws were clamped on the marks that were previously made on the material. The samples were then elongated a specified amount, (e.g. 90% or 1.8 in. (4.57 cm)), and allowed to retract. The elongation was recorded when the force during retraction reached 25 grams. The permanent set was calculated as follows:

% Permanent set=100×(distance x between the jaws when the resistance of the laminate drops to 25 grams force during the retraction cycle−initial length)÷total stretched length=[x(in.)−2(in.)]÷1.8=[x(cm)−5.08(cm)]÷4.57

Three repetitions were performed and the average value is represented in the examples below.

Breathability Test: The water vapor transmission rate (WVTR) for the sample materials was calculated generally in accordance with the following test method in order to measure the breathability of the samples. The test procedure establishes a means to determine the normalized rate of water vapor transmission through solid and porous films, nonwoven materials, and other materials while under steady state conditions. The material to be evaluated is sealed to the top of a cup of water and placed in a temperature-controlled environment. Evaporation of water in the cup results in a relatively higher vapor pressure inside the cup than the vapor pressure of the environment outside of the cup. This difference in vapor pressure causes the vapor inside the cup to flow through the test material to the outside of the cup. The rate of this flow is dependent upon the permeability of the test material sealed to the top of the cup. The difference between the beginning and ending cup weights is used to calculate the water vapor transmission rate.

In particular, circular samples measuring three inches in diameter were cut from each of the test materials and a control which was a piece of CELGARD® 2500 film from Hoechst Celanese Corporation. CELGARD® 2500 film is a microporous polypropylene film. The test dish was a 68-1 Vapometer cup distributed by Thwing-Albert Instrument Company of Philadelphia, Pa. One hundred milliliters of water were poured into each Vapometer cup and individual samples of the test materials and control material were placed across the open tops of the individual cups. A rubber gasket and metal ring (fitted to the cup) were placed over the sample and clamped using metal clamps. The sample test material and control material were exposed to room temperature over a 6.5 centimeter diameter circle, having an exposed area of approximately 33.17 square centimeters. The cups were placed in an oven at a temperature of about 38° C. (100° F.), long enough for the cups to reach thermal equilibrium. The cups were removed from the oven, weighed and replaced in the oven. The oven was a constant temperature oven with external air circulating through it to prevent water vapor accumulation inside. A suitable forced air oven is, for example, a Blue M Power-O-Matic 60 oven distributed by Blue M. Electric Company of Blue speak, Ill. After 24 hours, the cups were removed from the oven and weighed again. The preliminary test water vapor transmission rate values were calculated with Equation (I) below:

APP MVT=(grams weight loss over 24 hours)×7571/24 expressed in g/m²/24 hours

Approximate moisture vapor transfer is designated by "APP MVT". Under the predetermined set conditions of about 38° C. (100° F.) and ambient relative humidity, the WVTR for the CELGARD® 2500 control has been defined to be 5000 grams per square meter for 24 hours. Accordingly, the control sample was run with each test and the preliminary test values were corrected to set conditions using Equation (II) below:

WVTR=(Test WVTR/control WVTR)×(5000 g/m²/24 hours)  (II)

Hydrohead: A measure of the liquid barrier properties of a fabric is the hydrohead test. The hydrohead test determines the height of water (in centimeters) which the fabric will support before a predetermined amount of liquid passes through, usually 3 drops. A fabric with a higher hydrohead reading has a greater barrier to liquid penetration than a fabric with a lower hydrohead. The hydrohead test is performed according to Federal Test Standard 191A, Method 5514 using a Textest FX-3000 Hydrostatic Head Tester available from Marto Industries, Inc., P.O. Box 1071, Concord, N.C. A circular head having an inner circumference of 26 cm was used to clamp down the sample.

% Theoretical Extensibility: The % Theoretical Extensibility is the amount of extensibility and retractability that can be expected for necked laminates of the present invention, based upon how much the original width is reduced and assuming the original laminate has no inherent extensibility. In the following equations, original width is the un-necked width (transverse dimension) of the laminate, while necked width is the width of the laminate after necking. % Theoretical Extensibility can be determined as follows:

% Theoretical Extensibility=100×[(original width—necked width)÷necked width]

which can be rewritten as:

% Theoretical Extensibility=100×[(original width÷necked width)−1]

The % of the original width that the laminate is necked can be represented by the following equation:

% original width=100×(necked width÷original width)

which can be rewritten as:

(original width÷necked width)=100÷% original width

Substituting this equation into % Theoretical Extensibility above:

% Theoretical Extensibility=100×[(100÷% original width)−1]

So, for each sample below, the original width was measured, as was the necked width, and % Theoretical Extensibility was calculated as shown below in Table 3.

Example 1

This Example explains the process used to prepare the necked laminate which was then used as part of the composite materials below. The necked laminate was prepared from a non-elastic film layer and a non-elastic nonwoven web layer. A 1.5 mil layer of blown film made of 48% by weight (25 volume percent) SUPERCOAT calcium carbonate as manufactured by English China Clay America, Inc. of Sylacauga, Ala., 47% by weight (68 volume percent) linear low density polyethylene (LLDPE) available under the trade designation DOWLEX NG3347A as manufactured by the Dow Chemical Company ("Dow"), 5% by weight (7 volume percent) low density polyethylene (LDPE) available under the trade designation 6401 as manufactured by Dow, and 2000 ppm antioxidant stabilizer available under the trade designation B900 as manufactured by Ciba Specialties Company of Tarrytown, N.Y. The film layer, made of the composition as described above, was pre-made and wound onto a roll. To make this film layer highly breathable, it should be stretched over about 4×(4 times its original length), e.g. up to 5× and more. The film layer was then unwound from a film unwind unit into a conventional machine direction orienter manufactured by the Marshall and Williams Company where it was partially stretched as shown in Table 1 below (stretching draw) in the machine direction to form a partially stretched, breathable film layer. Likewise, a 0.4 OSY basis weight standard polypropylene spunbond having a wireweave bond pattern, such as that made by the Kimberly-Clark Corporation of Dallas, Tex., was unwound and an adhesive of 3 gsm weight (at the application point) available as H2525A from Ato-Findley of Wauwatosa, Wis. was applied to one surface of the nonwoven web layer using an air assisted spraying device such as a meltblown device as described in Butin, et al., supra. Such devices are generally described in, for example, commonly assigned U.S. Pat. No. 4,949,668 to Heindel et al.; U.S. Pat. No. 4,983,109 to Miller et al., assigned to Nordson Corporation; and U.S. Pat. No. 5,728,219 to Allen et al., assigned to J&M Laboratories, Inc.

The adhesive side of the nonwoven web layer was then laminated to the partially stretched film layer using laminating rollers at a pressure of 30 pli (5.4 kg/linear cm) of a smooth resilient (rubber coated) anvil roll on one side and a smooth, unheated, steel roll to form a laminate.

Figure 10:
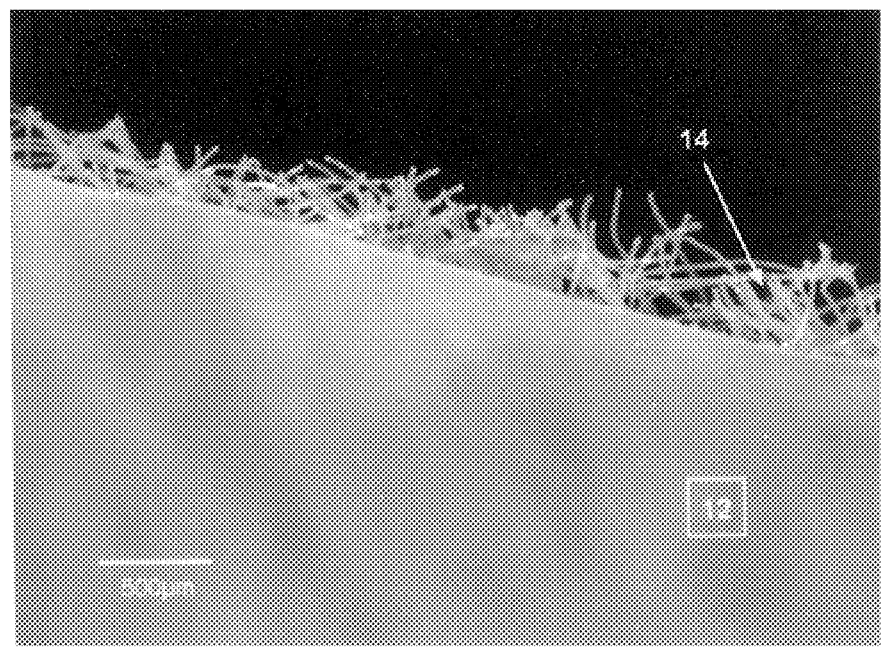
FIG. 10 is an oblique view of an optical photomicrograph of a prior art laminate.

The laminate was then stretched in the longitudinal dimension and necked in the transverse direction by passing it through a stretch nip at a greater speed than the speed of the laminating rollers (see Table 1 below, Laminate Necking Draw). The necking draw caused contraction (necking) of the laminate in the transverse direction. The laminating rollers were spaced about 8 feet (2.4 m) from the stretch nip. "Total draw" in Table 1 is the necking draw multiplied by the stretching draw and was sufficient to insure enough orientation or stretching of the film layer to make it highly breathable. The thus formed transversely extensible and retractable necked laminate was then wound onto a roll. Samples were cut from the necked laminate and subjected to tests, the results of which are reported below in Table 1. Samples C1 and C2 are comparative (baseline) examples wherein the film layer was stretched as indicated, but the laminate was not necked. FIG. 10 shows an oblique image of a prior art laminate of Sample C1, wherein the film layer 12 was fully stretched prior to lamination to the neckable material 14 to form the laminate which was not subsequently necked. Sample 8 was a repeat of Sample 7. "Peak strain" is the strain at "peak load".

TABLE 1

| Sample | Total Draw | Film Stretching Draw | Laminate Necking Draw | WVTR g/m²/ 24 hr | Hydrohead mbar | LD Peak Strain % | LD Peak Load lb. (kg) | TD Peak Strain % | TD Peak Load lb. (kg) |
|---|---|---|---|---|---|---|---|---|---|
| C1 | 5.0X | 5.0X | 1.0X | 2799 | 353 | 35.7 | 25.62 (11.62) | 92.15 | 5.11 (2.32) |
| C2 | 3.6X | 3.6X | 1.0X | 1759 | 265 | 66.4 | 23.36 (10.59) | 100.82 | 6.16 (2.79) |
| 3 | 3.9X | 3.6X | 1.1X | 1004 | 316 | 65.6 | 26.33 (11.94) | 99.98 | 6.15 (2.79) |
| 4 | 4.3X | 3.6X | 1.2X | 866 | 437 | 69.1 | 30.75 (13.95) | 94.99 | 6.01 (2.73) |
| 5 | 4.6X | 3.6X | 1.3X | 1474 | 383 | 65.2 | 33.32 (15.11) | 126.92 | 5.43 (2.46) |
| 6 | 50X | 3.6X | 1.4X | 1213 | 454 | 55.6 | 44.07 (19.99) | 197.79 | 4.99 (2.26) |
| 7 | 5.2X | 3.6X | 1.45X | — | 383 | 48.8 | 35.01 (15.88) | 144.25 | 5.46 (2.48) |
| 8 | 5.2X | 3.6X | 1.45X | 1140 | 387 | 56.0 | 40.20 (18.23) | 141.24 | 4.70 (2.13) |

Figure 11A:
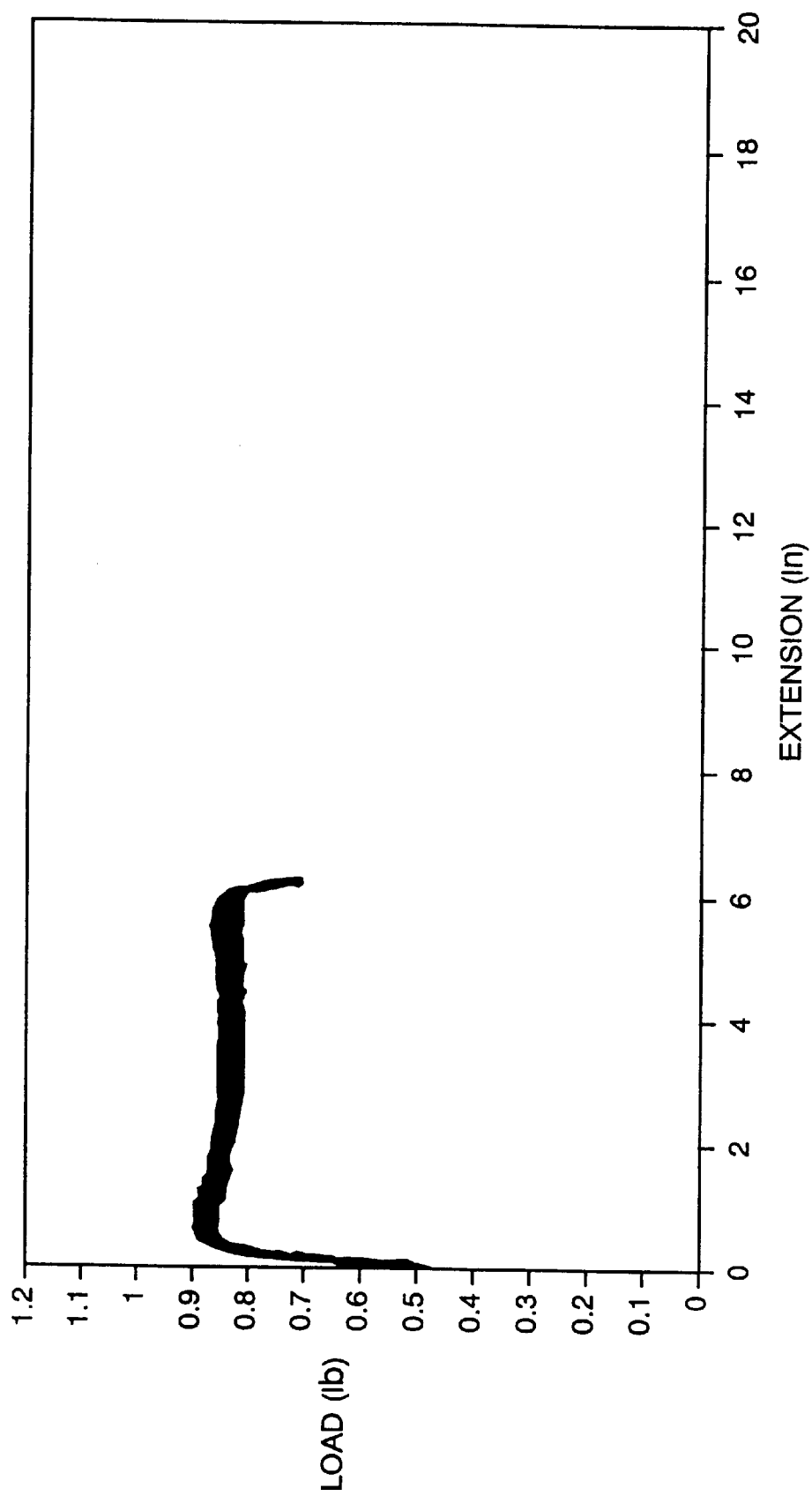
FIGS. 11*a, b* and *c*, and 12*a, b* and *c* graphically illustrate load versus extension curves for various samples.
Figure 11B:
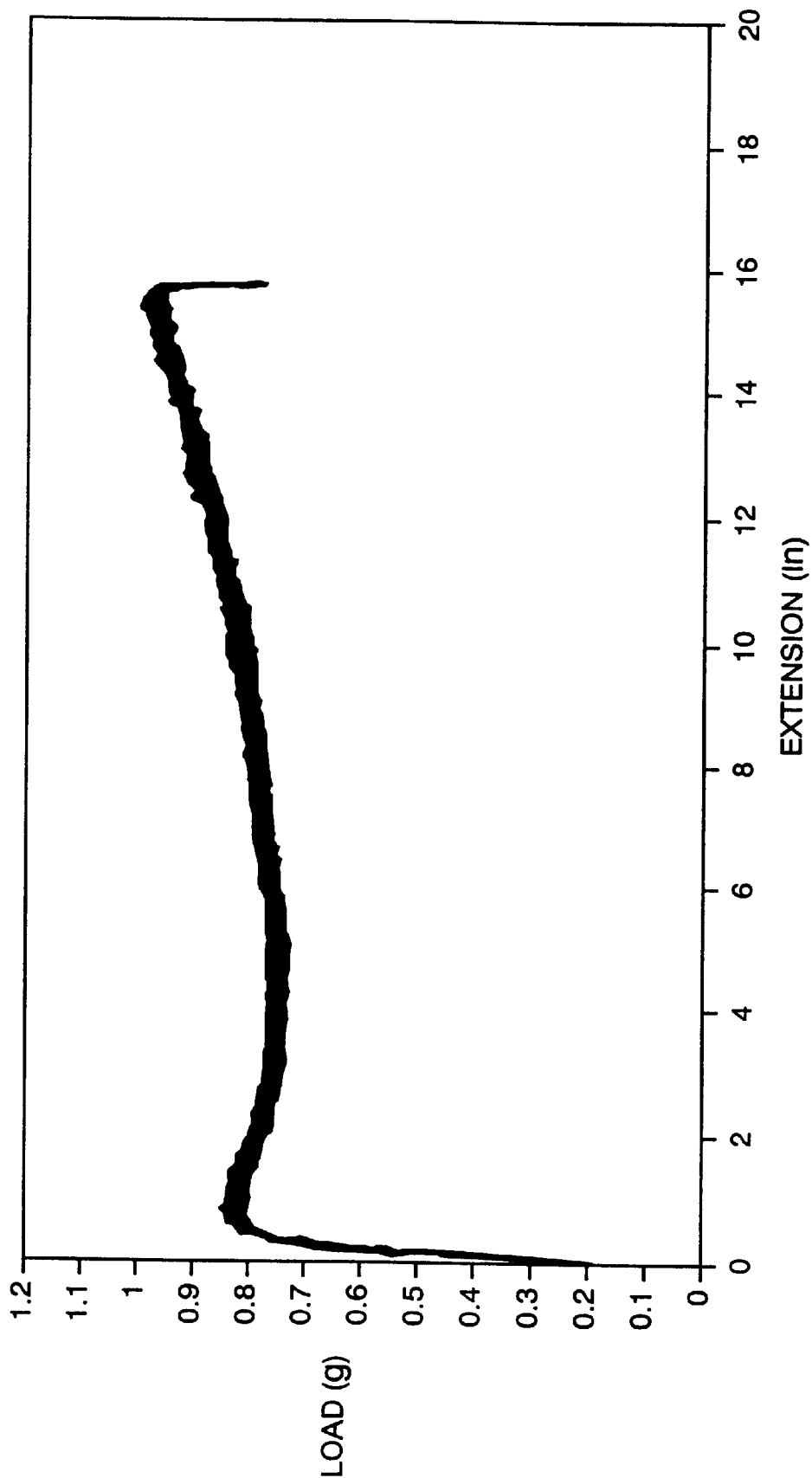
Figure 11C:
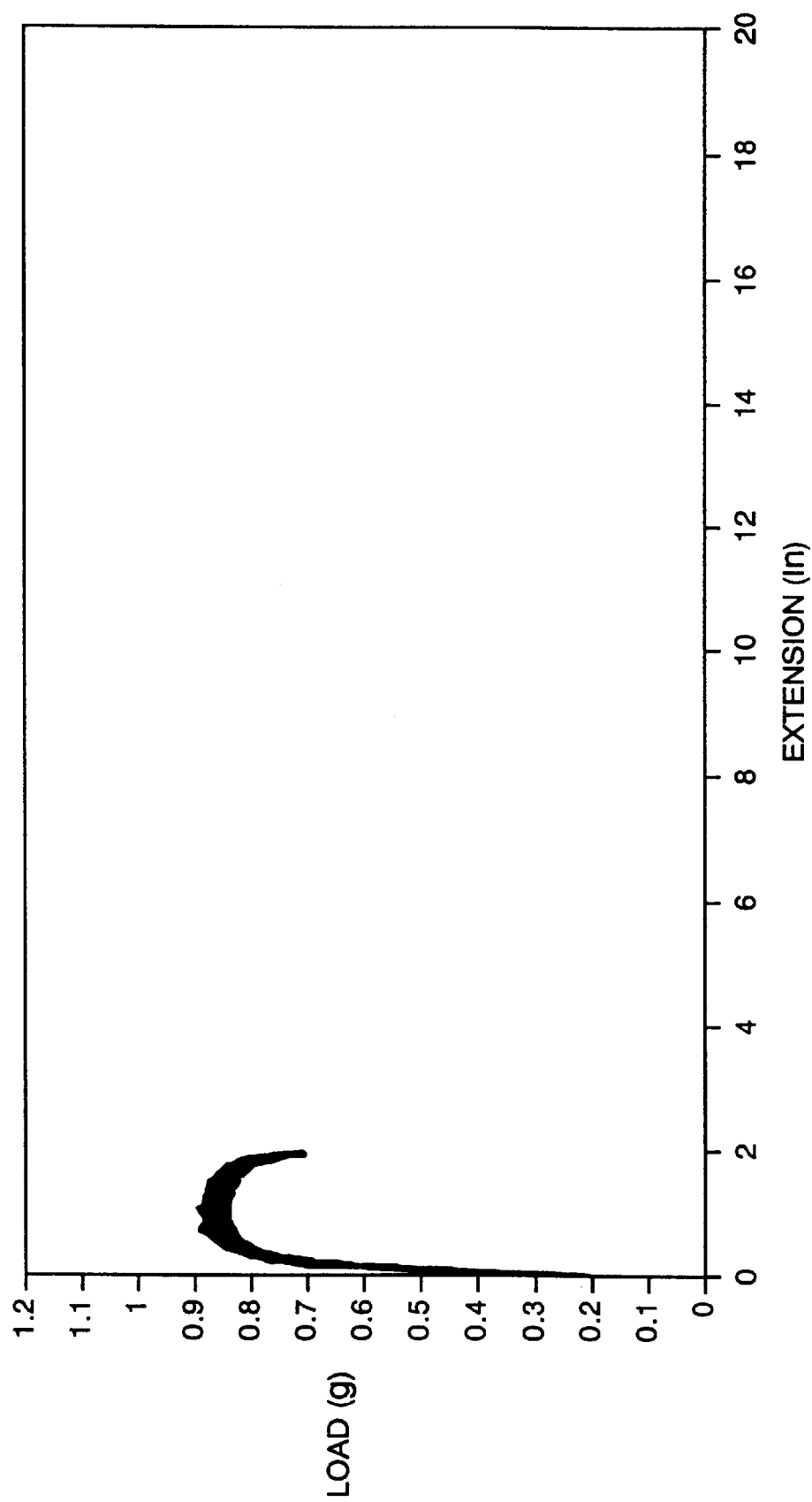
Figure 12A:
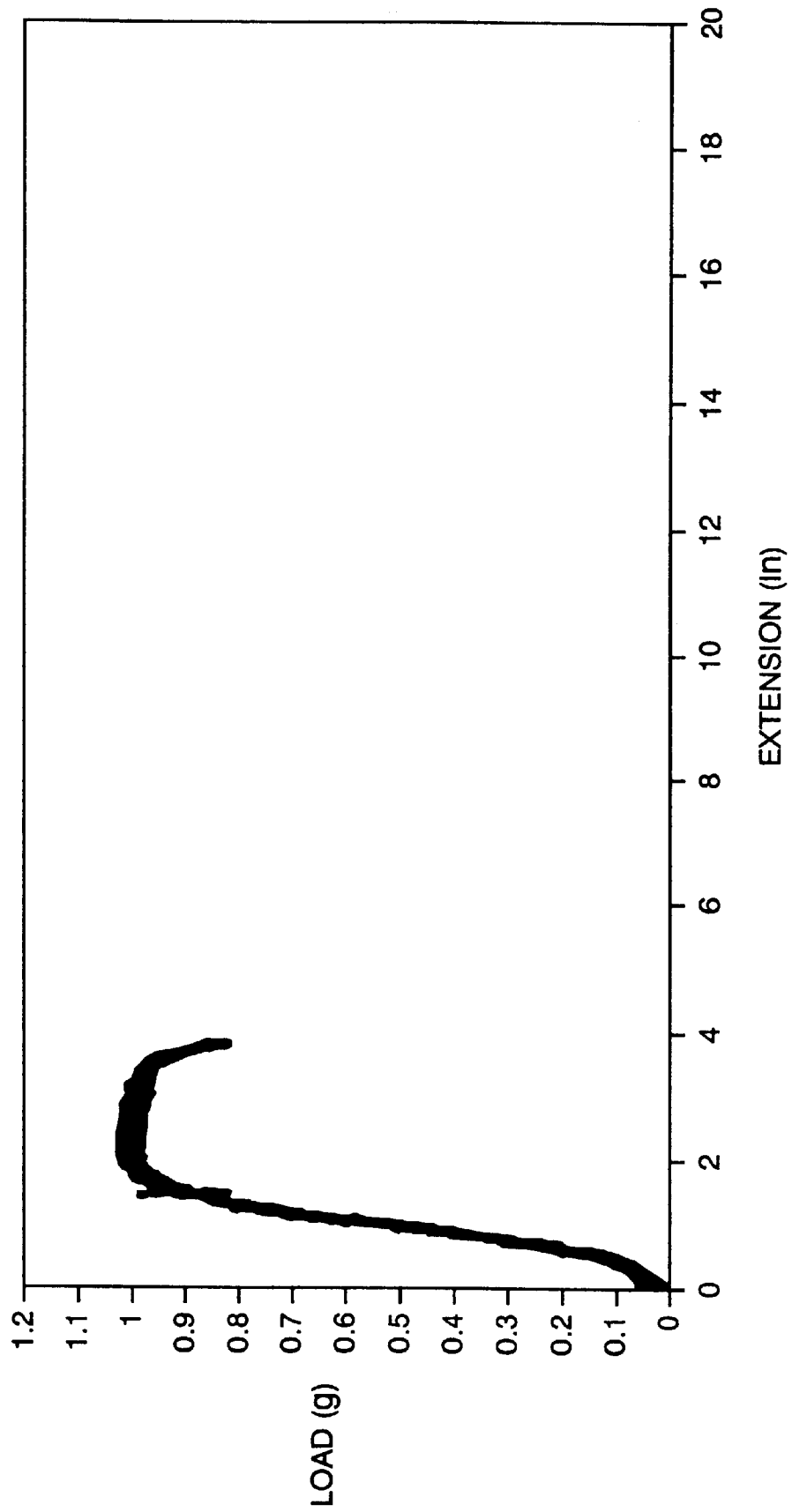
Figure 12B:
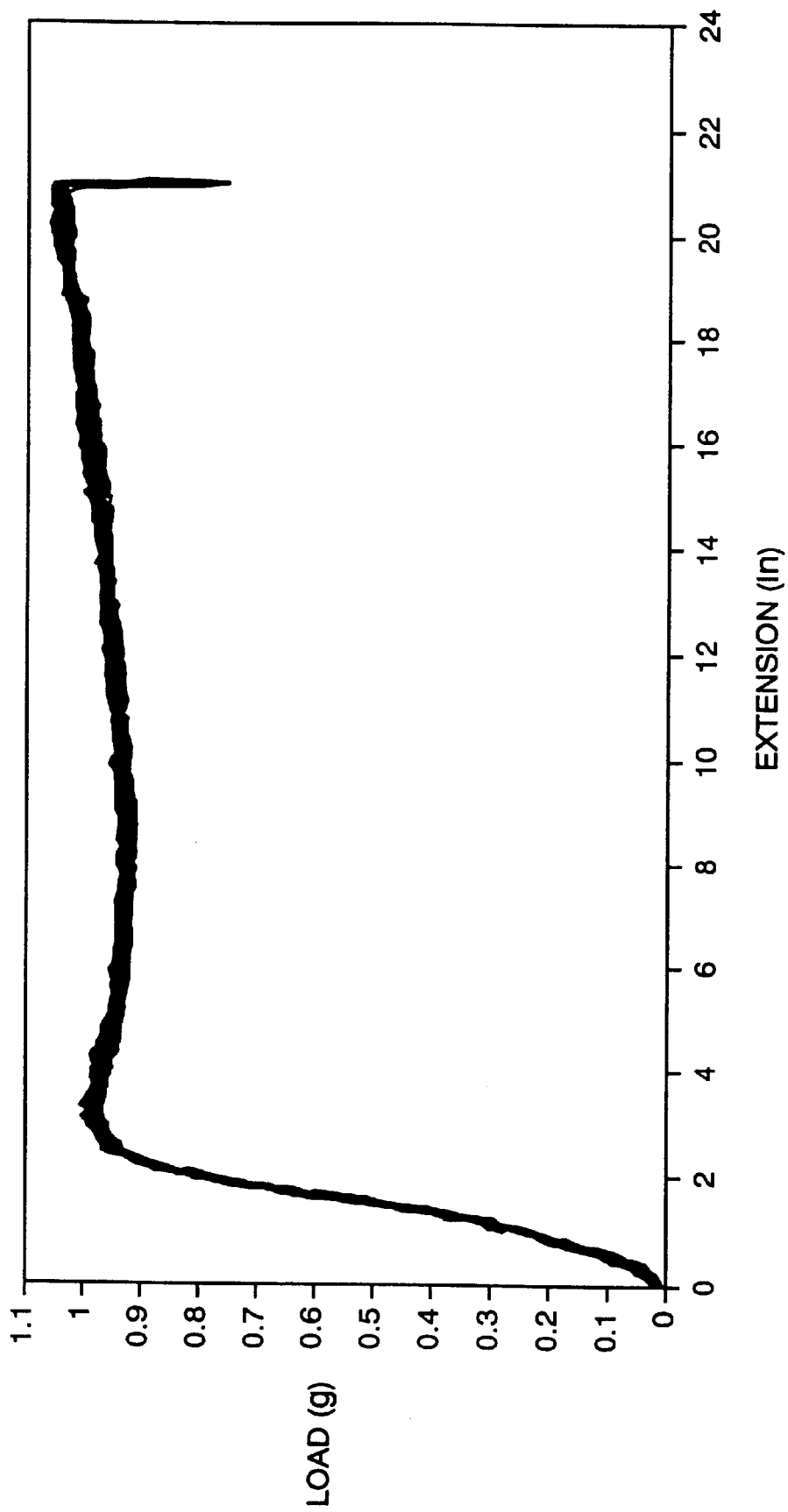
Figure 12C:
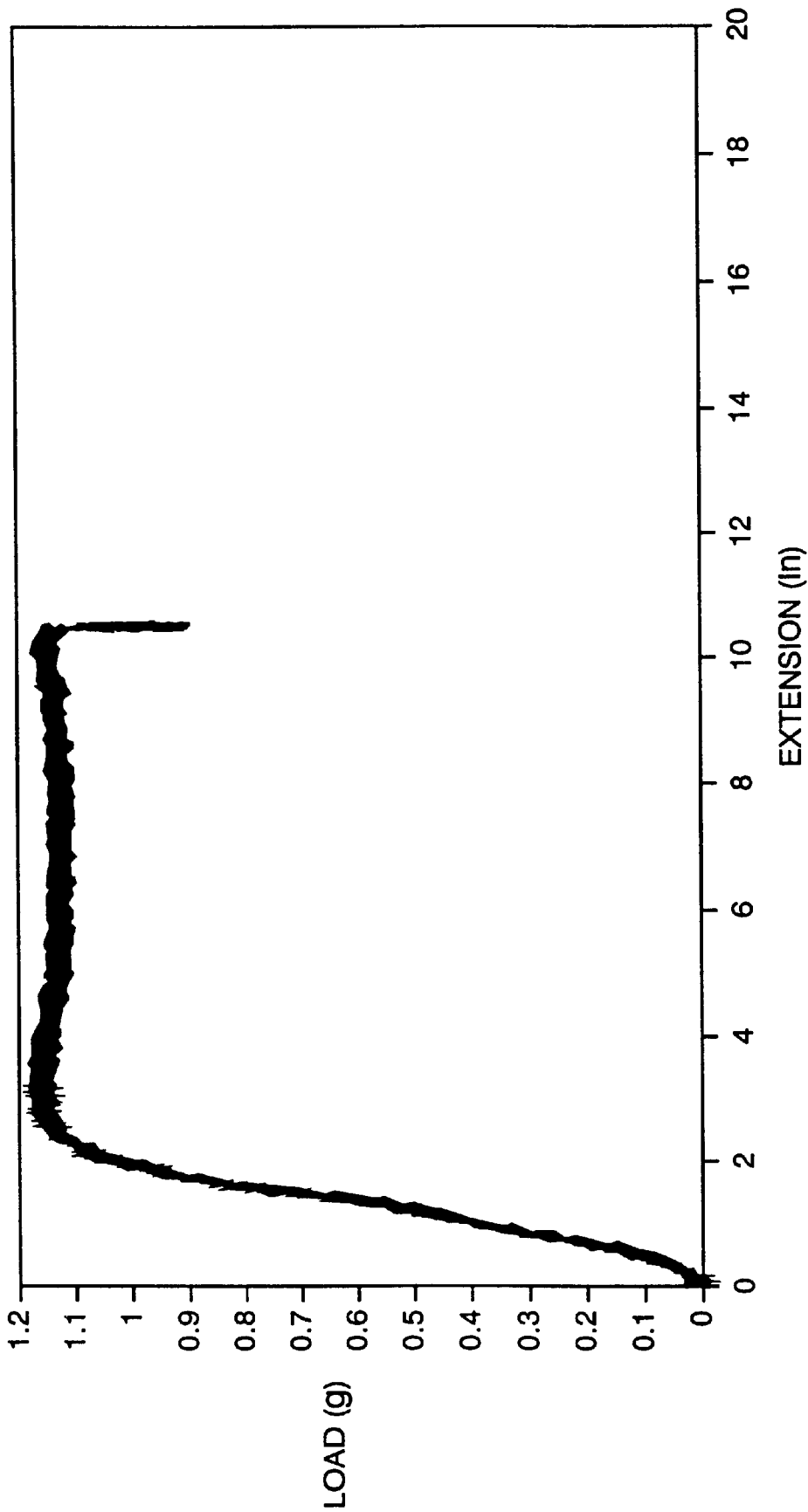
Figure 14:
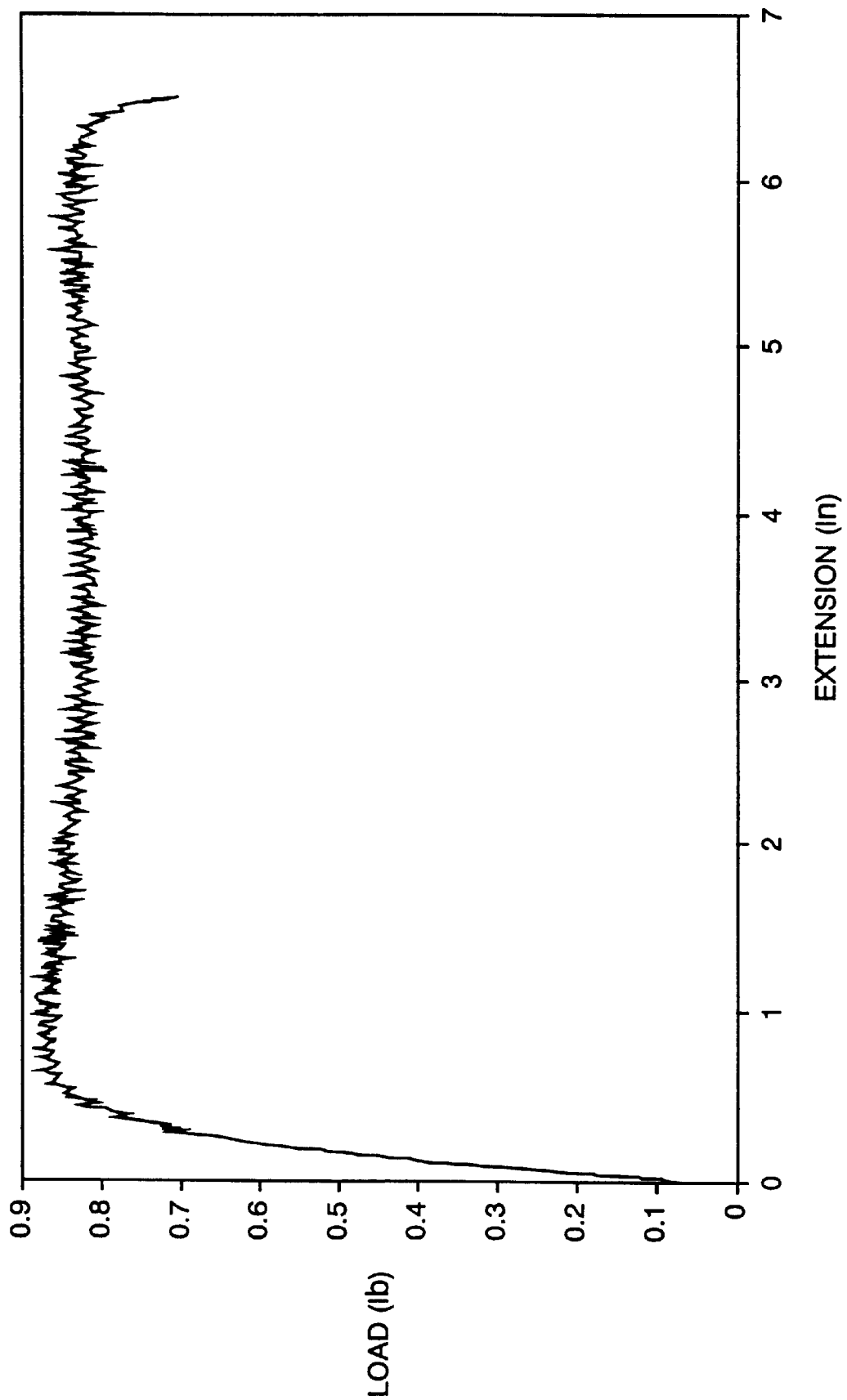
FIGS. 14–15 graphically illustrate enlarged curves of load versus extension for various samples.
Figure 15:
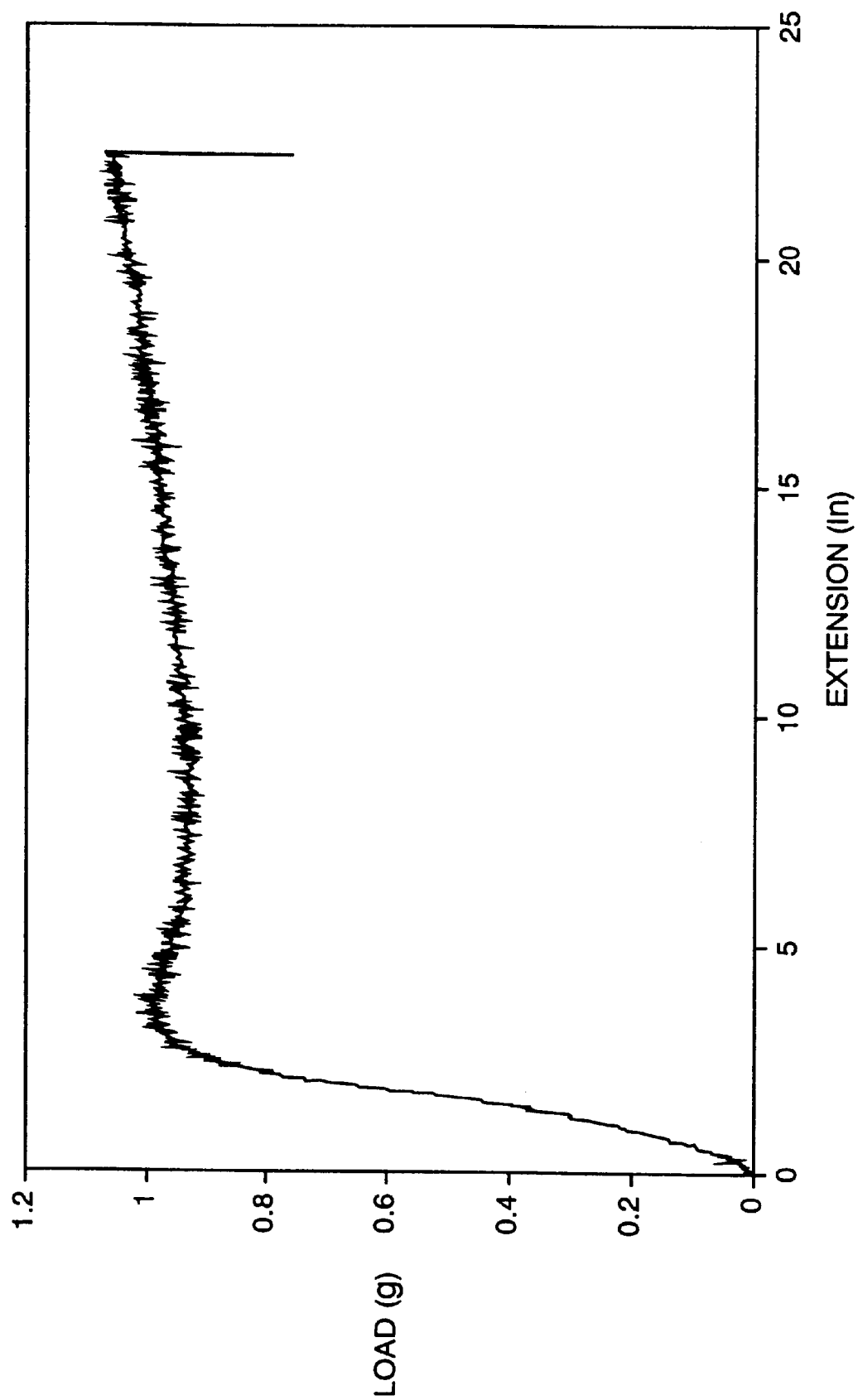

Sample 6 has the highest TD peak strain. In this laminate, the film layer has been drawn a total of 5.0×, which is typical drawing for such articles. The laminate has additionally been necked by a 1.4× draw. The film layer of Sample C1 has also been drawn a total of 5.0×, but the laminate has not been necked at all. Even though the film layers have been drawn by the same amount, the example of the present invention, Sample 6, has a much greater TD peak strain than the comparative example, which is an indication of the improvement of the transverse extensibility and retractability of the present invention. FIGS. 11a, b, and c, and 12a, b, and c, graphically illustrate load versus extension curves for samples C1 and 6, while FIGS. 14 and 15 graphically illustrate enlarged curves of load versus extension for these samples. FIGS. 11a, b, and c relate to three replicates of the delaminated film layer of Sample C1, whereas FIGS. 12a, b, and c relate to three replicates of the delaminated film layer of Sample 6, having the striated rugosities.

Table 3 below represents necked width in inches (cm) as a function of percent stretch and shows how readily the necked laminates elongated in the transverse direction for each of the samples of Table 1. From the tensile strength test above, the force in pounds (kilograms) was recorded below in Table 2 for each sample at 30%, 60%, 90%, 120%, 150%, and 180% The laminates which had been necked to a narrower width (Samples 5,6,8; Table 3 "Laminated Necked Width" column) elongated at a much less force at the same % elongation than the control and to a much greater extent before breaking. If the sample broke either on or before the percent step change, it has been designated as "- - ".

Table 3 additionally shows the calculated % Theoretical Extensibility as described above for each of the samples of Table 1.

TABLE 3

| Sample | Laminate Necked Width in (cm) | % Original Width | % Theoretical Extensibility |
|---|---|---|---|
| C1 | 12 ⅜ (31.43) | 100 | 0 |
| C2 | 12 ¼ (31.12) | 99 | 1 |
| 3 | 11 ½ (29.21) | 93 | 7.5 |
| 4 | 10 ¾ (27.31) | 87 | 15 |
| 5 | 8 ¾ (22.23) | 71 | 41 |
| 6 | 7 ½ (19.05) | 61 | 65 |
| 8 | 6 ⅜ (16.19) | 51 | 94 |

The breathability was measured by WVTR for the necked laminate when it was in the TD extended configuration, since this is the configuration it would have when in use as for instance in a diaper. Three repetitions of Sample 6 were extended 100% and 166% and tested for WVTR. The results were as follows in Table 4. Note that the TD extended laminate has a WVTR much higher than either of the comparative examples.

TABLE 2

| Sample | 30% | 60% | 90% | 120% | 150% | 180% |
|---|---|---|---|---|---|---|
| C1 | 2.51 (1.14) | 4.21 (1.91) | 5.05 (2.29) | — | | |
| C2 | 3.16 (1.43) | 5.05 (2.29) | 6.02 (2.73) | — | | |
| 3 | 2.74 (1.24) | 4.88 (2.21) | 5.88 (2.67) | — | | |
| 4 | 2.78 (1.26) | 4.89 (2.22) | 5.92 (2.69) | — | | |
| 5 | 1.30 (0.59) | 2.84 (1.29) | 4.41 (2.00) | 5.27 (2.39) | — | |
| 6 | 0.60 (0.27) | 1.28 (0.58) | 2.13 (0.97) | 3.22 (1.46) | 4.09 (1.86) | 4.73 (2.15) |
| 7 | 1.51 (0.68) | 2.78 (1.26) | 4.18 (1.90) | 5.06 (2.30) | 5.38 (2.44) | — |
| 8 | 1.21 (0.55) | 2.33 (1.06) | 3.42 (1.55) | 3.89 (1.76) | 4.47 (2.03) | — |

TABLE 4

| Sample 6 | WVTR g/m²/24 hr |
|---|---|
| Unstretched (from Table 1 above) | 1213 |
| 100% extended | 3960 |
| 166% extended | 4250 |

To better describe the TD extensibility of the film layer, for Samples C1 and 6 above, the film layer was delaminated from the spunbond layer for a further test. Prior to delamination, a length of 3 inches (7.62 cm) was marked on the film side of the laminate across the TD. The delamination was conducted by completely immersing and soaking the laminate in denatured ethyl alcohol (ethanol) which softened and partially dissolved the adhesive bonding between the film layer and spunbond layer, such that the striated rugosities of the film layer were not removed, damaged, or otherwise distorted, Once delaminated, the film layer was tested in a tensile tester as described above and the force was measured when the film layer had been extended by 0.3 inches (0.762 cm) (10% strain). The force required to extend Sample C1 (the average of three repetitions) was approximately 1000 grams per mil of the film layer thickness. The force required to extend Sample 6 (the average of three repetitions), on the other hand, was approximately 60 grams per mil of the film layer thickness, which was the thickness determined with the striated rugosities flattened out.

Example 2

Additional laminates were prepared as described above, except that a non-elastic adhesive was used in some samples and that some samples were heated after being necked. The modifications were made to evaluate the impact of: 1) using a non-elastic adhesive as compared with the semi-elastic adhesive used above, and 2) heating the laminate after the necking process. For each sample, the non-elastic film layer was stretched to 4× its length prior to lamination to the spunbond layer. The laminates were necked as indicated in Table 5 and tested for permanent set as described above. The non-elastic adhesive used was Rextac® 2730, available from Huntsman Polymers in Odessa, Tex. Further, the samples that were heated after necking were contacted with heated rolls maintained at a temperature of about 170° F. (76° C.).

A 10 cm×10 cm (3.94 in.×3.94 in.) sample was measured while the laminate was still wound on a roll. Since the materials were wound under tension and some degree of relaxation tends to occur over time, the samples were re-measured after being cut from the roll. Samples C9 and C10 are comparative (baseline) materials wherein the film was stretched but the laminate was not necked.

TABLE 5

| Sample | Laminate Necking Draw | Actual Draw | Adhesive Type | Heat Applied | Sample Size Measured cm (in.) | Sample Size After Relaxation cm (in.) | % Permanent Set cm (in.) |
|---|---|---|---|---|---|---|---|
| C9 | 1.1X | 1.03X | Non-elastic | No | 10 × 10 (3.94 × 3.94) | 10 × 10 (3.94 × 3.94) | — |
| C10 | 1.1X | 1.03X | Semi-elastic | No | 10 × 10 (3.94 × 3.94) | 10 × 10 (3.94 × 3.94) | — |
| 11 | 1.43X | 1.32X | Non-elastic | No | 10 × 10 (3.94 × 3.94) | 10 × 12.2 (3.94 × 4.80) | 76 |
| 12 | 1.4X | 1.28X | Semi-elastic | No | 10 × 10 (3.94 × 3.94) | 9.6 × 11.6 (3.78 × 4.57) | 79 |
| 13 | 1.45X | 1.3X | Semi-elastic | No | 10 × 10 (3.94 × 3.94) | 9.5 × 11.8 (3.74 × 4.65) | 79 |
| 14 | 1.5X | 1.36X | Semi-elastic | Yes | 10 × 10 (3.94 × 3.94) | 10 × 10.5 (3.94 × 4.13) | 78 |
| 15 | 1.45X | 1.3X | Non-elastic | Yes | 10 × 10 (3.94 × 3.94) | 10 × 10.3 (3.94 × 4.06) | 80 |
| 16 | 1.45X | 1.3X | Non-elastic | No | 10 × 10 (3.94 × 3.94) | 10 × 11.25 (3.94 × 4.43) | 80 |

The heat set materials, Samples 14 and 15, maintained their original dimensions better than the materials that were necked and not heat set, based on a comparison between the sample size before and after cutting from the roll. Further, all of the materials, regardless of use of elastic or inelastic adhesive, exhibited the same degree of permanent set. There was little difference between the permanent set of the laminates made with the semi-elastic adhesive and those made with the inelastic adhesive, indicating that the small amount of elastic adhesive used does not bear on the overall extensibility and retractability of the nonwoven web laminate.

The samples were additionally tested for tensile properties in the transverse dimension (TD) and WVTR according tothe test methods described above. The results are summarized in Table 6.

TABLE 6

| Sample | Actual Draw | Adhesive Type | Heat Applied | TD Load at 50% Elongation lb. (kg) | TD Peak Strain % | TD Peak Load lb. (kg) | Unstretched WVTR g/m²24 hr |
|---|---|---|---|---|---|---|---|
| C9 | 1.03X | Non-elastic | No | 5.73 (2.60) | 62.5 | 6.24 (2.83) | 1667 |
| C10 | 1.03X | Elastic | No | 4.85 (2.20) | 89.7 | 6.15 (2.79) | 2121 |
| 11 | 1.32X | Non-elastic | No | 0.0904 (0.041) | 175 | 4.56 (2.07) | 1272 |
| 12 | 1.28X | Elastic | No | 0.375 (0.170) | 201 | 4.72 (2.14) | 1222 |
| 13 | 1.3X | Elastic | No | 0.617 (0.280) | 212 | 4.78 (2.17) | 903 |
| 14 | 1.36X | Elastic | Yes | 0.419 (0.190) | 192 | 3.57 (1.62) | 1482 |
| 15 | 1.3X | Non-elastic | Yes | 0.375 (0.170) | 174 | 3.37 (1.53) | 1400 |
| 16 | 1.3X | Non-elastic | No | 0.190 (0.086) | 174 | 4.52 (2.05) | N/A |

When the samples were elongated 50%, the control (unnecked) materials, Samples C9 and C10, exhibited a significantly higher load than the necked materials, Samples 11–16, indicating that a much greater force was needed to extend the control samples in the transverse dimension.

Example 3

Strands of elastomeric filaments in the form of rubber bands were attached lengthwise to the longitudinal dimension of the film side of the necked laminate of Sample 6 from Example 1 above, using 3M "Super77" spray adhesive. The entire film surface was sprayed with the adhesive. The stretched rubber bands were pressed against the adhesive and held there for about 15 seconds. While the rubber bands were still under tension, baby powder (as available from Johnson & Johnson), was sprinkled on the adhesive coated sample to eliminate the adhesive effect in locations other than at the rubber band attachment locations. Upon release of the biasing force, the elastomeric filaments recovered, drawing the necked laminate along with it. The thus formed composite material exhibited LD stretch and recovery and TD extensibility and retractability. FIGS. 20 and 21 show images of the thus formed composite material.

Example 4

A composite material was made as essentially described above for Example 3, except that the elastomeric filaments were not stretched and were attached perpendicular to the longitudinal dimension and the striated rugosities. In other words, the elastomeric filaments were attached in the transverse dimension of the necked laminate as can be seen in FIG. 22. The thus formed composite material exhibited TD stretch and recovery.

Example 5

A Stretch Bonded Laminate (SBL) of a 73 gsm elastic material as an inner elastic material, which had a standard polypropylene spunbond facings such as that made by the Kimberly-Clark Corporation of Dallas, Tex., attached to both sides of the inner elastic material, was carefully delaminated from one of the spunbond layers. "Stretch bonded" conventionally refers to an elastic member being bonded to another member while the elastic member is extended at least about 25 percent of its relaxed length. "Stretch bonded laminate" refers to a material having at least two layers in which one layer is a gatherable layer and the other layer is an elastic layer. The layers are joined together when the elastic layer is in an extended condition so that upon relaxing the layers, the gatherable layer is gathered. Such a material may be stretched to the extent that the non-elastic material gathered between the bond locations allows the elastic material to elongate. One type of stretch bonded laminate is disclosed, for example, by commonly assigned U.S. Pat. No. 4,720,415 to Vander Wielen et al., in which multiple layers of the same polymer produced from multiple banks of extruders are used.

The elastic material with one spunbond facing was attached to the laminates from Example 1 above. For the elastic material of the delaminated SBL used herein, the elastic material was formed by meltblowing a blend of 70 percent, by weight, of an A-B-A' block copolymer having polystyrene "A" and "A" endblocks and a poly(ethylene-butylene) "B" midblock (obtained from the Shell Chemical Company under the trade designation KRATON® GX 1657) and 30 percent, by weight, of a polyethylene (obtained from U.S.I. Chemical Company under the trade designation PE Na601).

Meltblowing of the elastic material was accomplished by extruding the blend of materials through an extruder and through a meltblowing die as described in commonly assigned U.S. Pat. No. 4,663,220 to Wisneski et al.

Figure 19A:
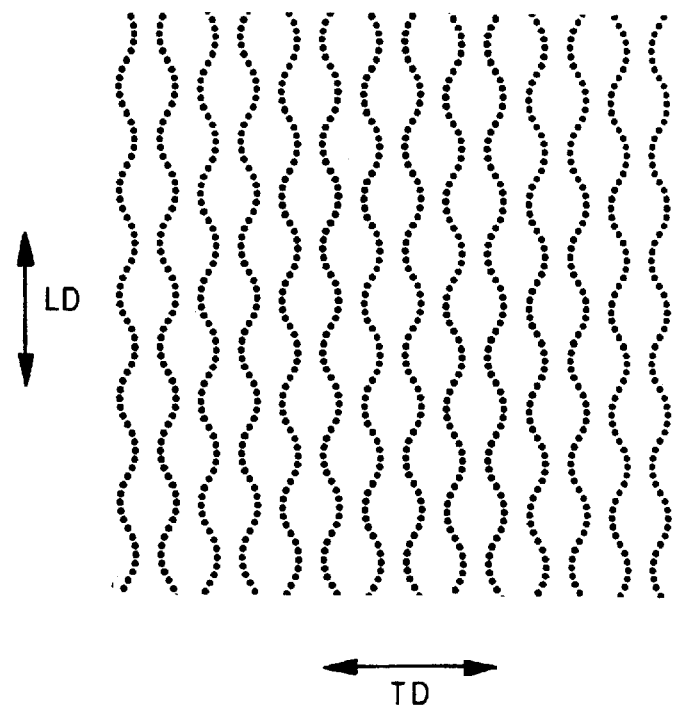
FIGS. 19*a* and *b* depict sine wave and dot bonding patterns, respectively, used to join the necked laminate to the elastic material to form a composite material of the present invention.

The elastic material and spunbond layer were then laminated to the necked laminates of Example 1 above to form composite materials as follows in Table 7. The elastic material side was bonded directly to the film side of the necked laminate through the use of sine wave pattern bond plate and Carver Press (Model #1528, Serial #2518-66). The bond pattern used is shown in FIG. 19a. A press temperature of 150° F. (65.56° C.) was used, and the bonding period was 15 seconds. The force used was 20,000 pounds (88,960 Newtons) as indicated by the gauge on the Carver Press. The sample size was about 9×10 inches (22.86×25.4 cm).

Figure 25:
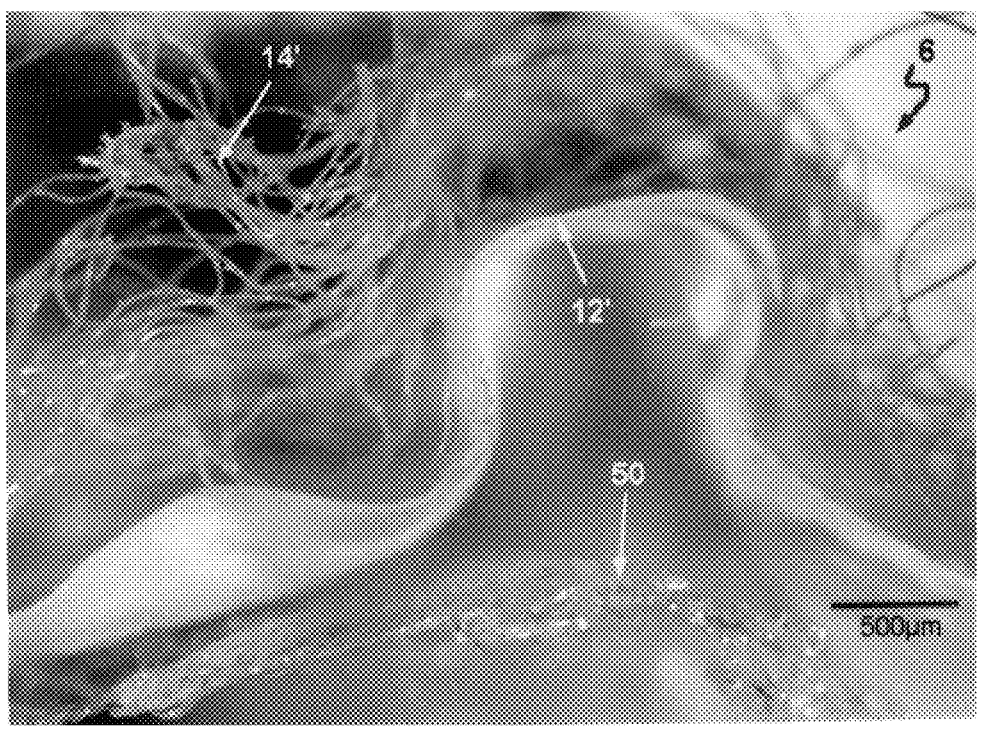
FIG. 25 is a cross-sectional optical photomicrograph of the composite material, in this case using an stretched elastic meltblown nonwoven web to form the elastic material layer according to the present invention.
Figure 26:
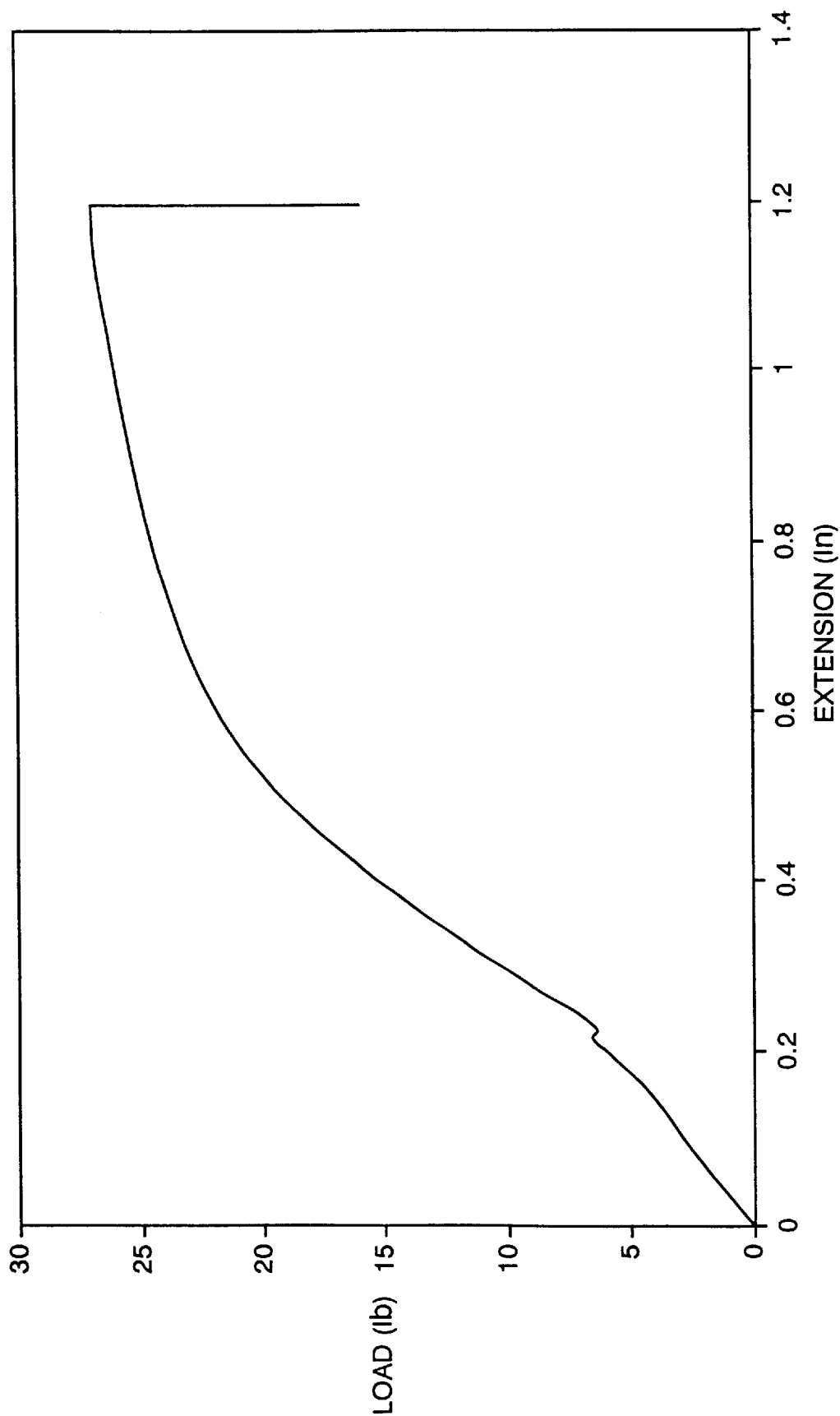
FIGS. 26–28 graphically illustrate results of LD tensile testing load versus extension curves for various samples.
Figure 27:
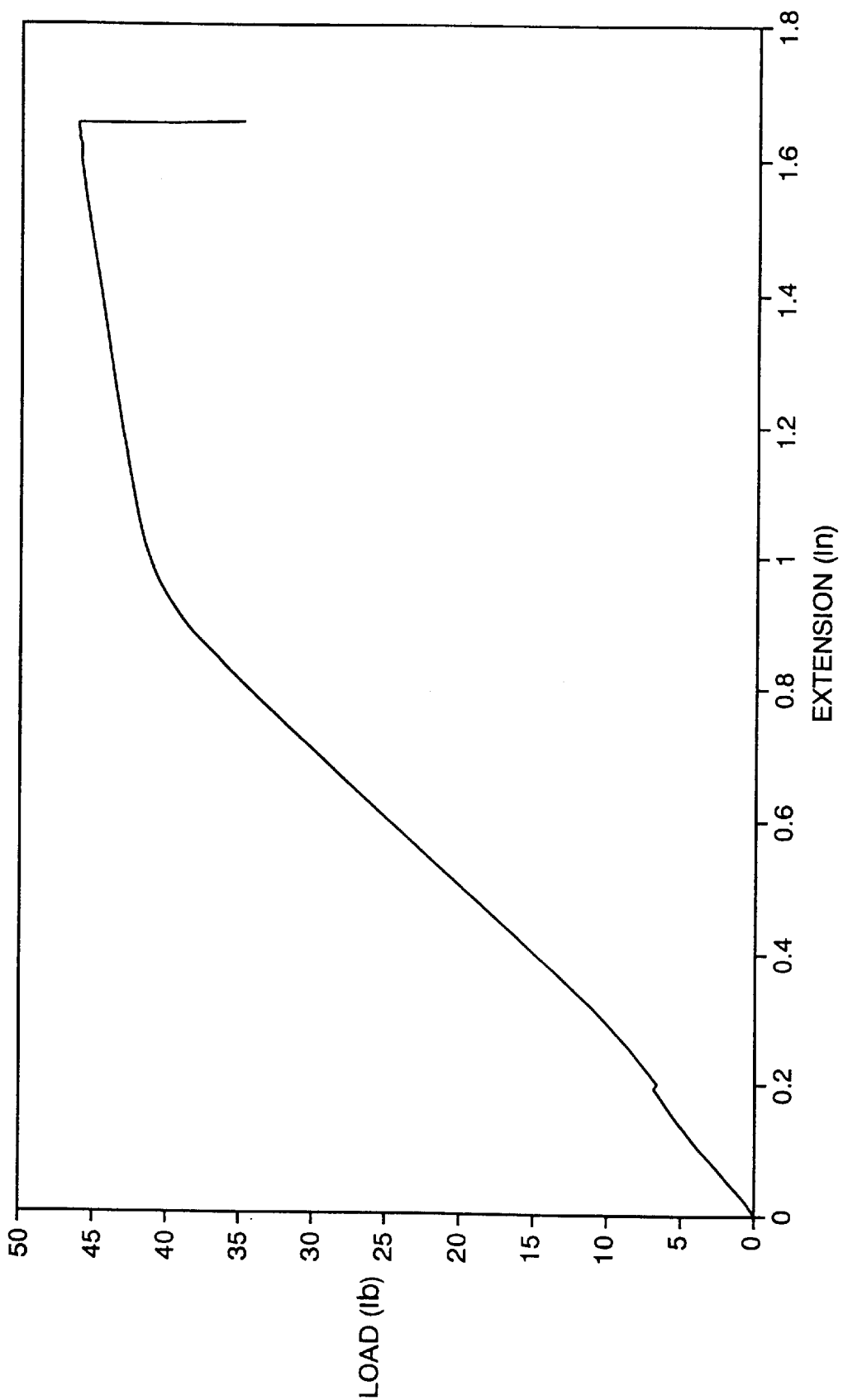
Figure 28:
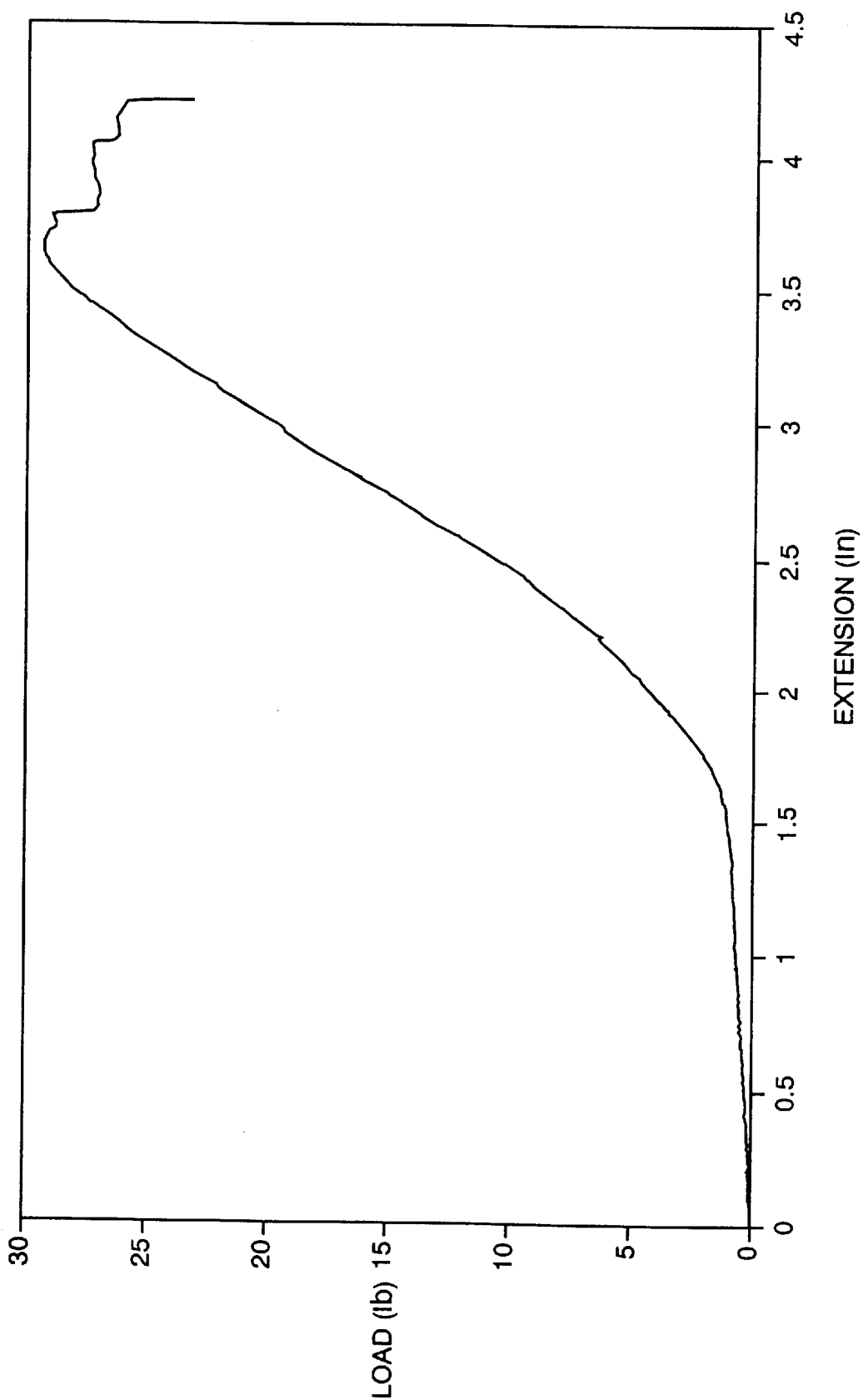
Figure 29:
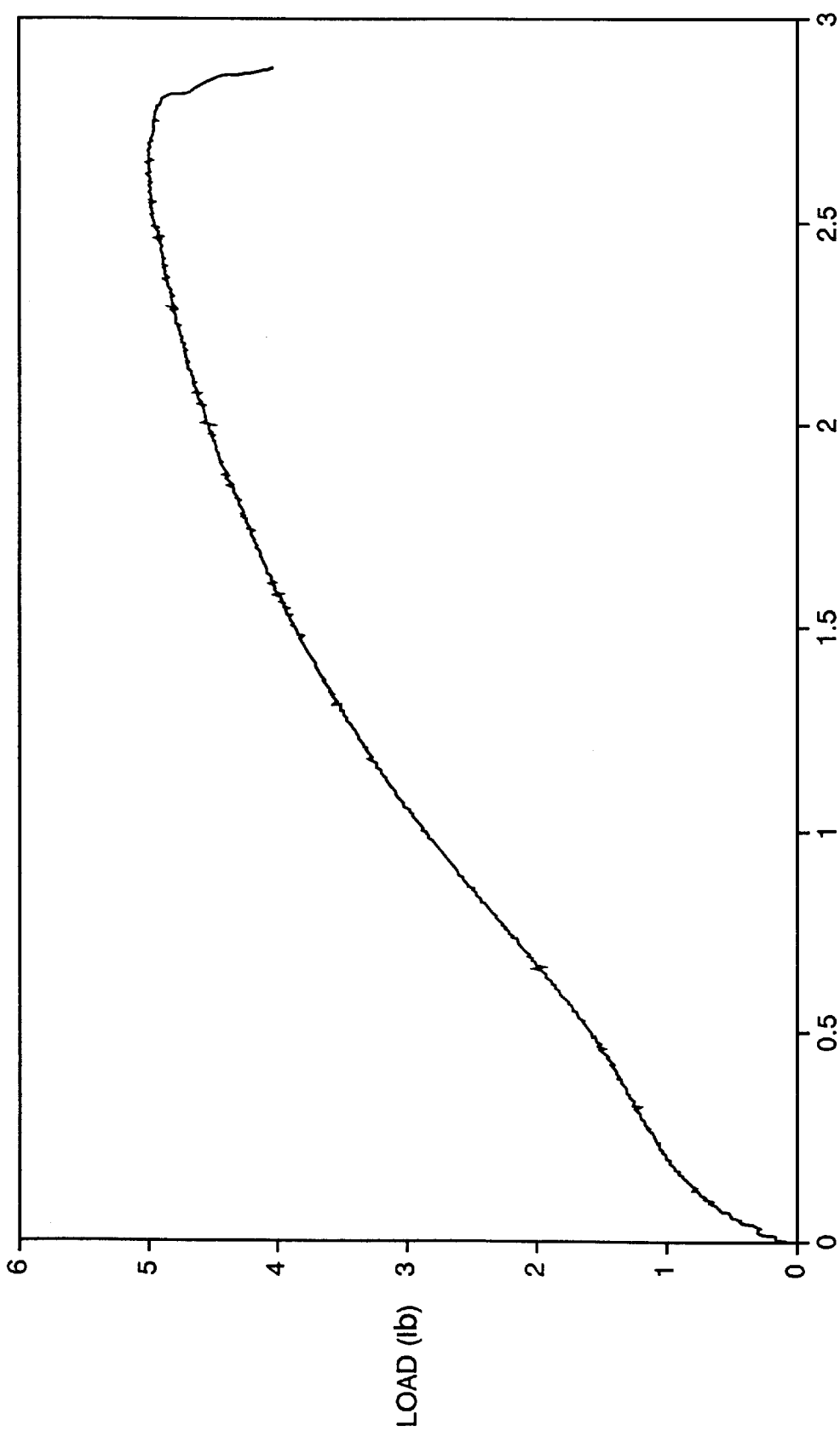
FIGS. 29–31 graphically illustrate results of TD tensile testing load versus extension curves for various samples.
Figure 30:
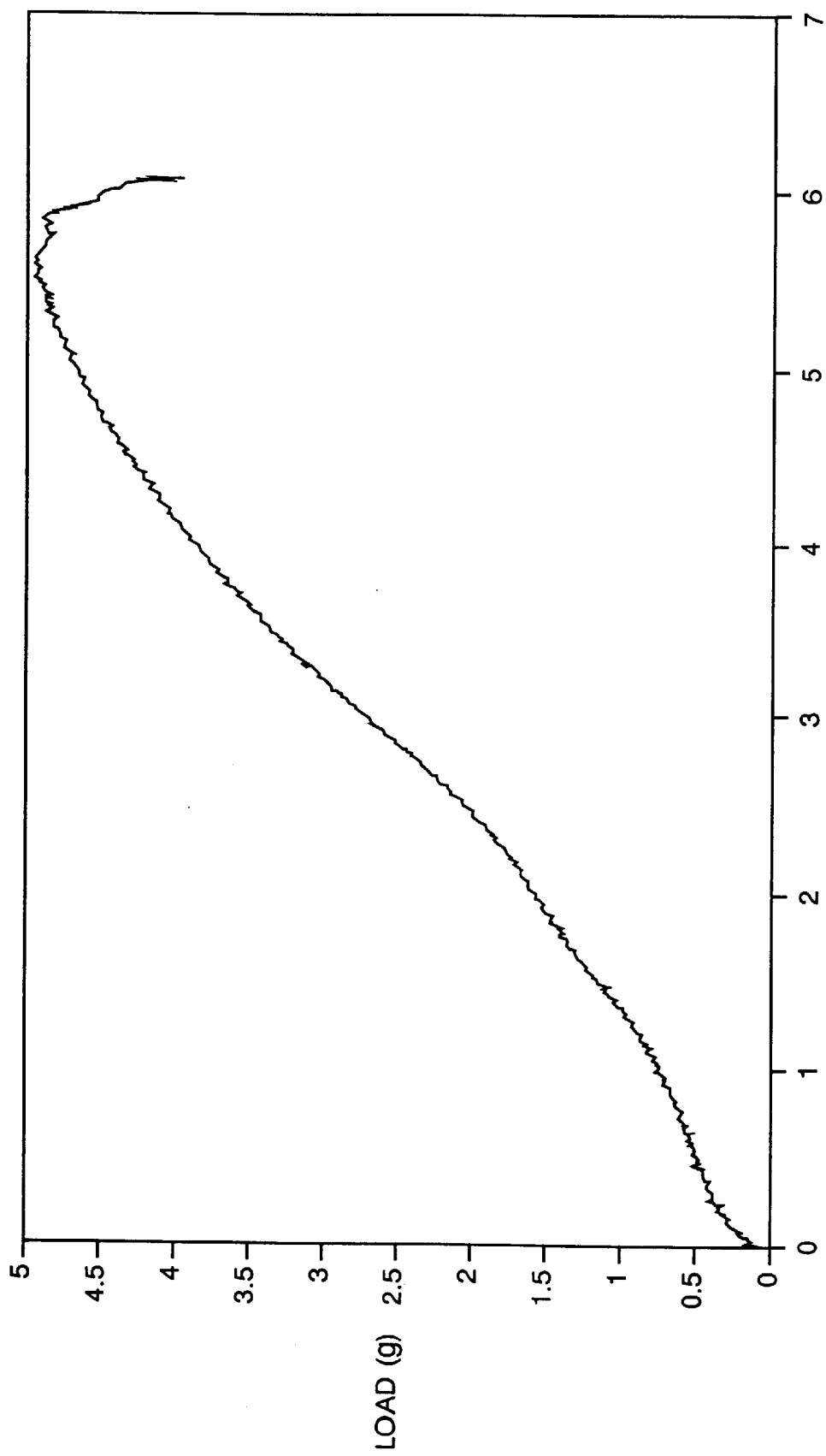
Figure 31:
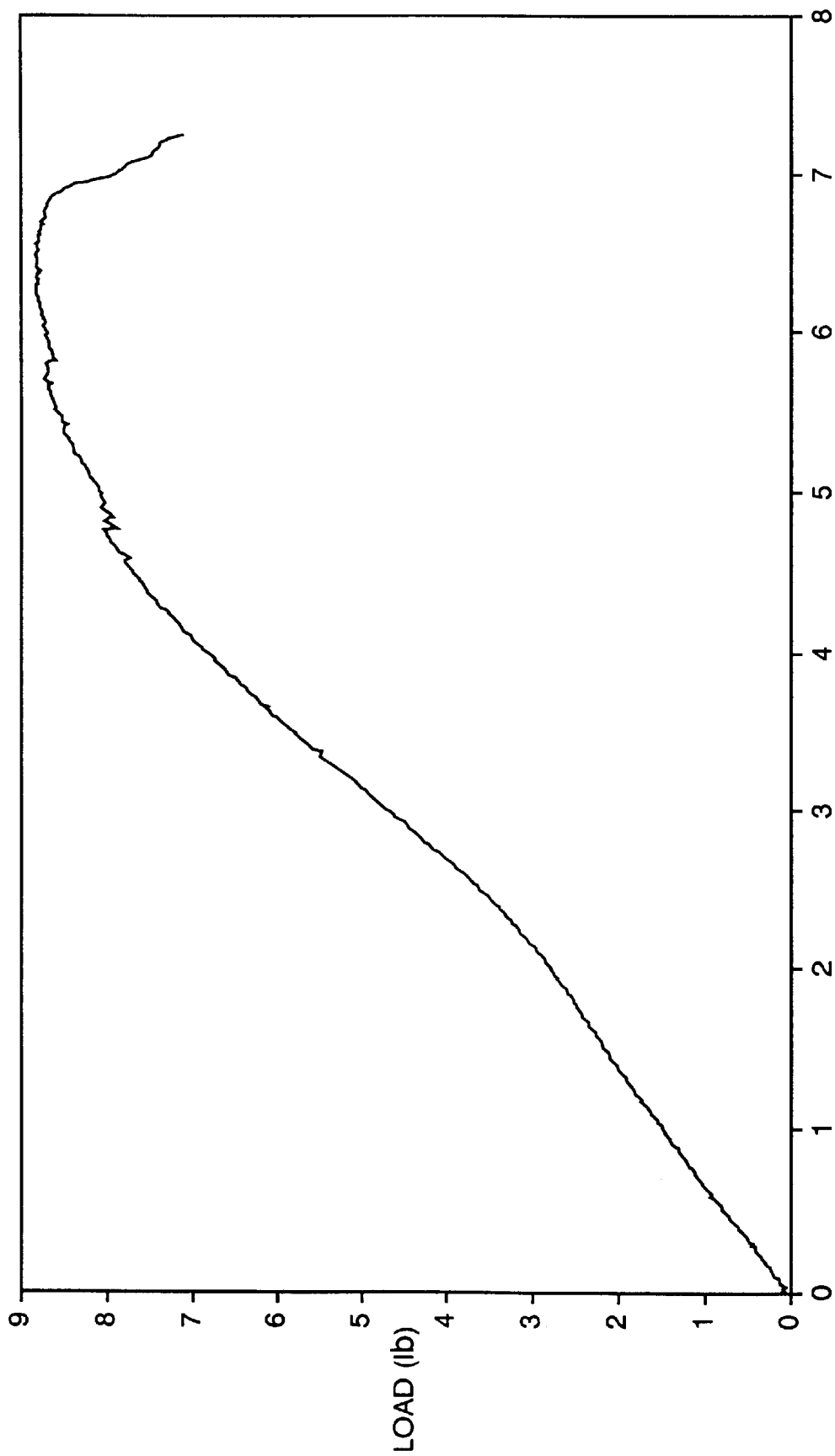

Samples 1–8 of Example 1 above were used to form the necked laminate for the composite materials of Samples 9–16, respectively. The Samples were elongated to break and the peak load and elongation at that peak load were recorded as follows in Table 7 below. By having the additional spunbond layer (from the SBL), "TD Peak Strain" increases for all of the Samples 9–16 to about 150 to 160%. This was because the peak load is now augmented by the SBL spunbond layer as is shown by the high TD peak loads. The one exception is that Sample 14 (which was Sample 6 with the attached elastic layer and the additional spunbond layer) had a strain of 189.657% as compared to Sample 6's strain of 197.79% because Sample 6 had such a high elongation itself. FIG. 25 is a cross-sectional optical photomicrograph of a composite material wherein the elastic material was not stretched showing the multiple layers of Sample 14.

TABLE 7

| Sample | Description | TD Peak Strain | TD Peak Load |
|---|---|---|---|
| C1 | Laminate Control (Total Draw 5.0x, Necking Draw 1.0x) | 92.15 | 2319.03 |
| C2 | Laminate (Total Draw 3.6x, Necking Draw 1.0x) | 100.823 | 2795.73 |
| C3 | Laminate (Total Draw 3.9x, Necking Draw 1.1x) | 99.98 | 2792.10 |
| C4 | Laminate (Total Draw 4.3x, Necking Draw 1.2x) | 94.993 | 2758.96 |
| C5 | Laminate (Total Draw 4.6x, Necking Draw 1.3x) | 126.92 | 2465.67 |
| C6 | Laminate (Total Draw 5.0x, Necking Draw 1.4x) | 197.79 | 2263.64 |
| C7 | Laminate (Total Draw 5.2x, Necking Draw 1.45x) | 144.25 | 2478.84 |
| C8 | Laminate (Total Draw 5.2x, Necking Draw 1.45x) | 141.24 | 2131.53 |
| 9 | Laminate 1 with SBL attached | 165.055 | 8891.14 |
| 10 | Laminate 2 with SBL attached | 157.08 | 8863.44 |
| 11 | Laminate 3 with SBL attached | 150.283 | 10312.16 |
| 12 | Laminate 4 with SBL attached | 153.473 | 9129.49 |
| 13 | Laminate 5 with SBL attached | 168.35 | 8913.38 |
| 14 | Laminate 6 with SBL attached | 189.657 | 8996.92 |
| 15 | Laminate 7 with SBL attached (same as laminate 8) | 153.665 | 8564.71 |
| 16 | Laminate 8 with SBL attached | 138.765 | 7894.15 |

Figure 16:
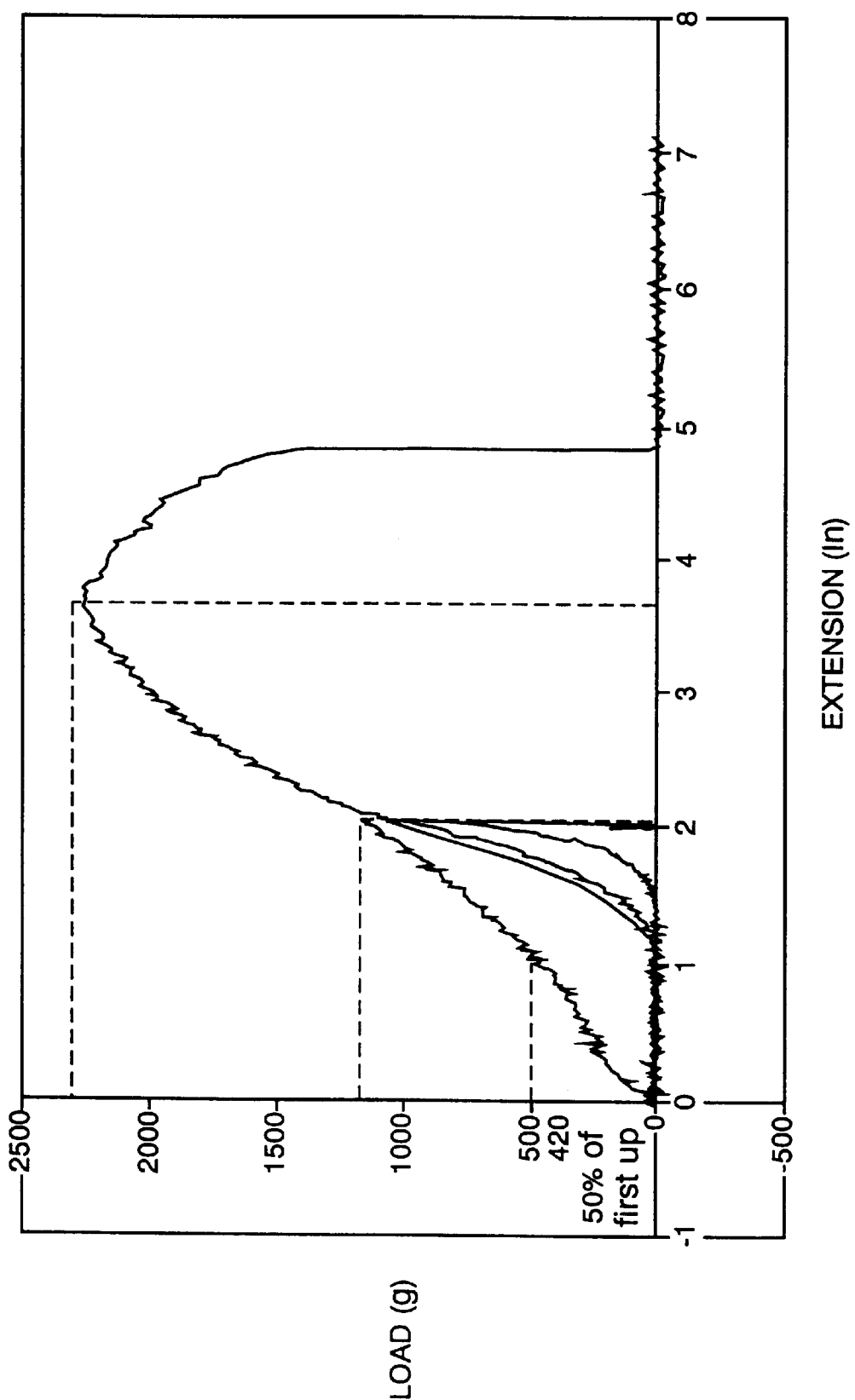
FIGS. 16–18 graphically illustrate results of cycling testing done on various samples.
Figure 17:
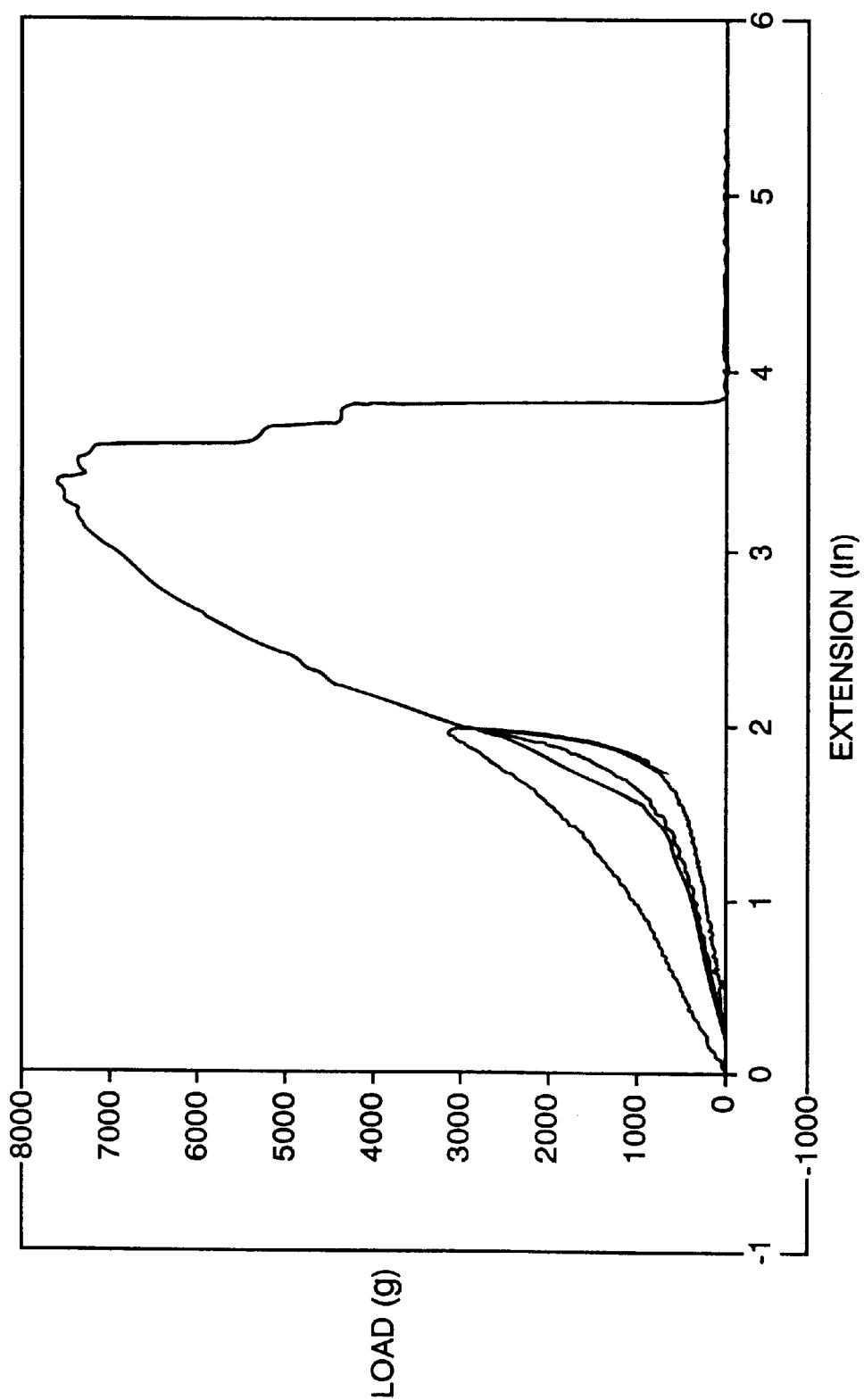

In Table 8, Samples 1–8 of Example 1 above are compared with Samples 9–16, respectively for the cycling test performed as described above. Each of the Samples was cycled to different lengths depending on "Elongation at Peak Load" from the tensile tests above. As can be deduced from this data, elastic materials helped to maintain the extension force and retractive force after the initial stretch, e.g. Samples 1–8 extended without tearing but did not retract very much, or at least very quickly. Samples 9–16, on the other hand, stretched and recovered in the TD direction as can be seen by the lower permanent set and the maintenance of the extension force and retractive force at 50% of the elongation distance. FIG. 16 shows cycling for Sample 6, while FIG. 17 shows cycling for Sample 1. Sample 6 has a high permanent set as compared to Sample 14.

TABLE 8

| Sample | % elongation cycled to | at 50% of elongation cycled to in grams | | | | Permanent Set (%) | TD Peak Load (g) | Elong @ Peak Load (%) |
|---|---|---|---|---|---|---|---|---|
| | | First up | Third up | First Down | Second Down | | | |
| C1 | 50 | 1027 | 98 | 5 | 6 | 62 | 2400 | 92 |
| 9 | 85 | 2757 | 458 | 242 | 231 | 20 | 8900 | 178 |
| C2 | 55 | 1513 | 97 | 1.4 | 13 | 61 | 2900 | 90 |
| 10 | 81 | 2815 | 446 | 237 | 217 | 21 | 10700 | 175 |
| C3 | 55 | 1114 | 57 | 8 | 11 | 64 | 3100 | 104 |
| 11 | 78 | 1913 | 374 | 225 | 206 | 20 | 9700 | 168 |
| C4 | 52 | 1141 | 33 | 3 | 7 | 64 | 2900 | 118 |
| 12 | 78 | 1915 | 396 | 234 | 217 | 20 | 9800 | 185 |
| C5 | 66 | 448 | 5 | 0 | 5 | 72 | 2700 | 157 |
| 13 | 87 | 1530 | 340 | 225 | 206 | 19 | 10400 | 216 |
| C6 | 101 | 420 | 12 | 9 | 6.6 | 76 | 2300 | 194 |
| 14 | 98 | 1064 | 380 | 246 | 230 | 19 | 8100 | 174 |
| C7 | 75 | 650 | 3.5 | 10 | 6 | 72 | 2600 | 151 |
| 15 | 80 | 1354 | 344 | 181 | 192 | 21 | 9800 | 188 |
| C8 | 73 | 193 | 24 | 2 | 4 | 79 | 2000 | 215 |
| 16 | 72 | 637 | 306 | 200 | 200 | 25 | 8100 | 182 |

A Stretch Bonded Laminate (SBL) having a 73 gsm elastic material was formed as described above for Example 5 except that both spunbond facings were removed from Samples 18–22. The inner elastic material, the KRATON® elastic meltblown, was then combined without stretching to the necked laminates of Example 1 above as follows: Sample 18 was made from Sample C1; Sample 19 was made from Sample C2; and Samples 20 and 21 were made from Sample 6. Also, this time, a press temperature of 120° F. (48.89° C.) and bonding period of 30 seconds was used.

Figure 18:
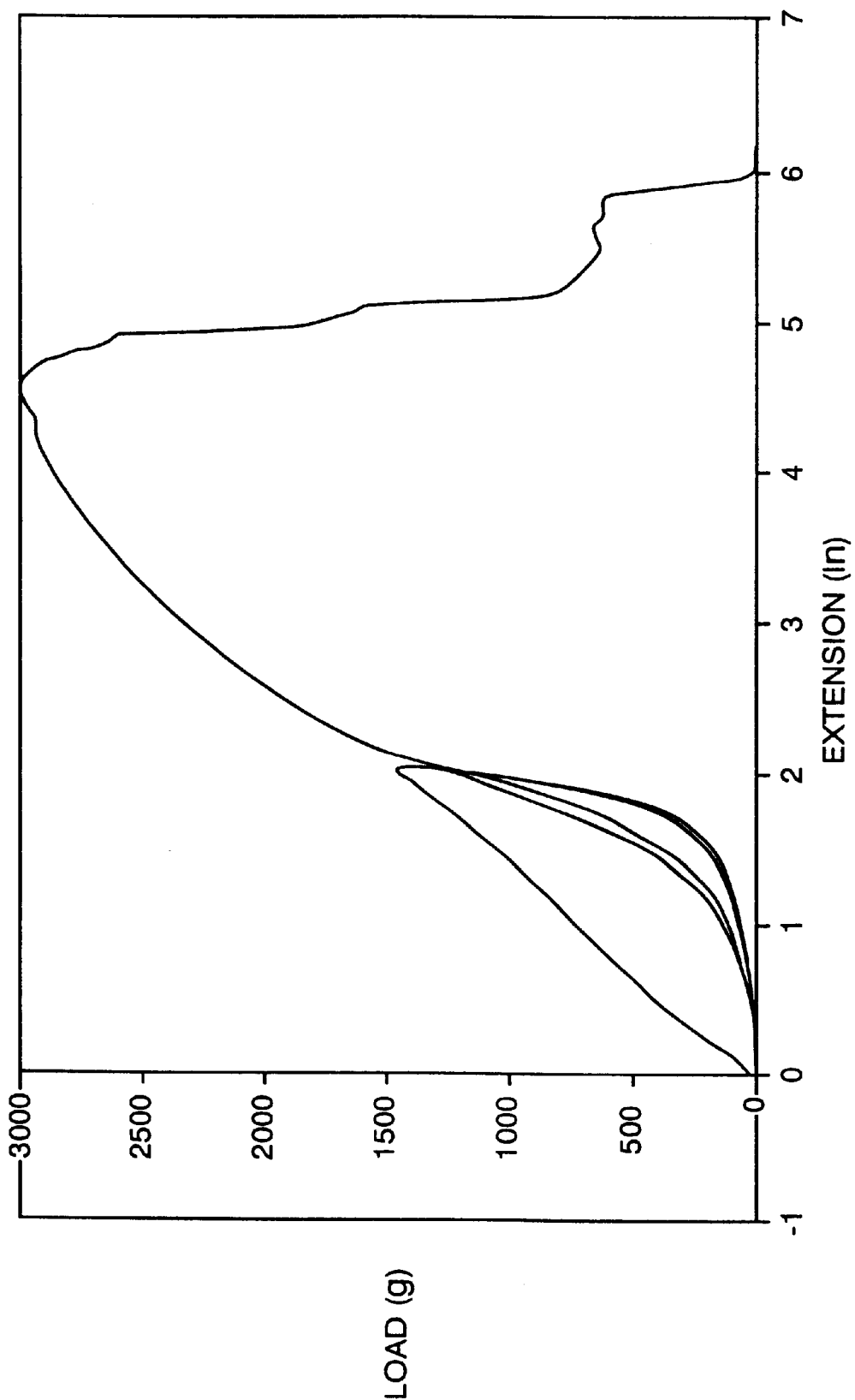
Figure 19B:
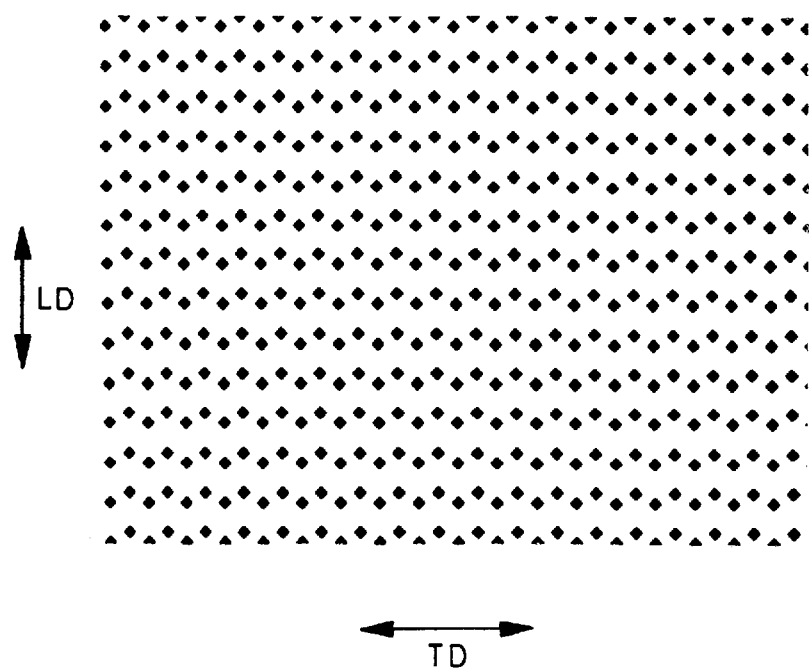

Sample sizes were 8×10 inches (20.32×25.4 cm). The sine wave bond pattern from FIG. 19a was used for Samples 18–20, while the dot bond pattern from FIG. 19b was used for Sample 21. These samples were cycle tested as described above for Example 2 and the results are reported below in Table 9. Again, the permanent set was greatly reduced when the elastic material was used to make the composite material. The extensive and retractive forces were significantly increased. FIG. 16 shows cycling for Sample 6, while FIG. 18 shows cycling for Sample 20.

TABLE 9

| Sample | % elongation cycled to | at 50% of elongation cycled to in grams | | | | Permanent Set (%) | TD Peak Load (g) | Elong @ Peak Load (%) |
|---|---|---|---|---|---|---|---|---|
| | | First up | Third up | First Down | Second Down | | | |
| C1 | 50 | 1027 | 98 | 5 | 6 | 62 | 2400 | 92 |
| 18 | 51 | 1326 | 172 | 58 | 51 | 40 | 3400 | 100 |
| C2 | 55 | 1513 | 97 | 1.4 | 13 | 61 | 2900 | 90 |
| 19 | 56 | 1694 | 178 | 56 | 47 | 41 | 3500 | 94 |
| C6 | 101 | 420 | 12 | 9 | 6.6 | 76 | 2300 | 194 |
| 20 | 102 | 683 | 112 | 70 | 65 | 32 | 3000 | 242 |
| 21 | 102 | 747 | 125 | 80 | 74 | 27 | 2900 | 221 |

Table 10 provides results from WVTR and hydrohead testing for all of the above described Samples, including Sample 22 which was made by stretching Sample 20 100% in the transverse direction.

TABLE 10

| Sample | Description | WVTR g/m$^2$/24 h | Hydrohead mbar |
|---|---|---|---|
| C1 | Laminate Control (Total Draw 5.0x, Necking Draw 1.0x) | 2799 | 353 |
| C2 | Laminate (Total Draw 3.6x, Necking Draw 1.0x) | 1759 | 265 |
| C3 | Laminate (Total Draw 3.9x, Necking Draw 1.1x) | 1004 | 316 |
| C4 | Laminate (Total Draw 4.3x, Necking Draw 1.2x) | 886 | 437 |
| C5 | Laminate (Total Draw 4.6x, Necking Draw 1.3x) | 1474 | 383 |
| C6 | Laminate (Total Draw 5.0x, Necking Draw 1.4x) | 1213 | 454 |
| C7 | Laminate (Total Draw 5.2x, Necking Draw 1.45x) | 1793 | 383 |
| C8 | Laminate (Total Draw 5.2x, Necking Draw 1.45x) | 1140 | 387 |
| 9 | Laminate 1 with SBL attached | 2362 | 253 |
| 10 | Laminate 2 with SBL attached | 1404 | 331 |
| 11 | Laminate 3 with SBL attached | 1118 | 427 |
| 12 | Laminate 4 with SBL attached | 970 | 457 |
| 13 | Laminate 5 with SBL attached | 1126 | 356 |
| 14 | Laminate 6 with SBL attached | 168 | 239 |
| 15 | Laminate 7 with SBL attached (same as laminate 8) | 1293 | 100 |
| 16 | Laminate 8 with SBL attached | 791 | 104 |
| 18 | Laminate 1 with unstretched Kraton attached | 2819 | 242 |
| 19 | Laminate 2 with unstretched Kraton attached | 1550 | 289 |
| 20 | Laminate 6 with unstretched Kraton attached | 1476 | 310 |
| 21 | Laminate 20 w/dot pattern instead of sine | 1471 | 350 |
| 22 | Laminate 20 stretched 2x | 2407 | 207 |

Table 11 below summarizes the WVTR data for Samples C1, C2, and 6, corresponding to their counterparts from above in Example 5 (Samples 9, 10, and 14) and Example 6 (18, 19, and 20), respectively. Composite materials which have the elastic material which is not stretched, therefore, have not been adversely affected with respect to breathability by addition of the elastic material.

TABLE 11

| Sample | Necked Laminate | Example 2 | Example 3 |
|--------|-----------------|-----------|-----------|
| C1 | 2799 | 2362 | 2819 |
| C2 | 1759 | 1404 | 1550 |
| 6 | 1213 | 1368 | 1476 |

Example 7

Sample 17 was made by adding the elastic material (KRATON® meltblown nonwoven web) from the inner elastic material described in Example 6 above to Sample 6 from Example 1 above. The elastic material was first stretched in the LD and bonded in the stretched state to the film side of Sample 6. Bonding was accomplished using the Carver Press as described above for Example 5. The bond pattern used was the sine wave pattern shown in FIG. 19a. A press temperature of 110° F. (43.33° C.) was used, and the bonding period was 15 seconds. The force used was 20,000 pounds (88,960 Newtons). The sample size was about 6×6 inches (15.24×15.24 cm). The samples were tested and the results reported in Table 12 below. Exemplary tensile testing curves are shown in FIGS. 26–31 for both LD and TD testing. FIG. 25 is a cross-sectional optical photomicrograph of the composite material of the present invention showing the multiple layers of Sample 17. Some of the samples were stretched as indicated and retested for WVTR to mimic breathability when the composite material was stretched as it would likely be in actual use. Sample 17 has both stretch and recovery in the LD and TD, as well as in all directions, which is not specifically indicated by this data. This Sample also has excellent liquid (water) barrier properties, breathability and has a very nice appearance and feel.

TABLE 12

| Sample | Description | WVTR g/m²/ 24 hr | Hydro-head mbar | LD Peak Strain % | LD Peak Load g | TD Peak Strain % | TD Peak Load g |
|--------|-------------|------------------|-----------------|------------------|----------------|------------------|----------------|
| C1 | Laminate Control (Total Draw 5.0X, Necking Draw 1.0X) | 2799 | 353 | 35.7 | 11631 | 92.15 | 2319 |
| 6 | Laminate (Total Draw 5.0X Necking Draw 1.4X) | 1213 | 454 | 56.62 | 20010 | 197.79 | 2264 |
| | Laminate 6 stretched 2X | 3960 | 207 | | | | |
| 17 | Laminate 6 with stretched KRATON ® attached | 1859 | 260* | 126.64 | 15014 | 196.53 | 3979 |
| | Laminate 17 stretched 2X in LD | 1424 | | | | | |
| | Laminate 17 stretched 2X in TD | 3018 | | | | | |

*Supported by a lightweight (approximatety 0.4 osy) layer of spunbond since it is elastic and would otherwise break under the weight of the water.

Figure 32:
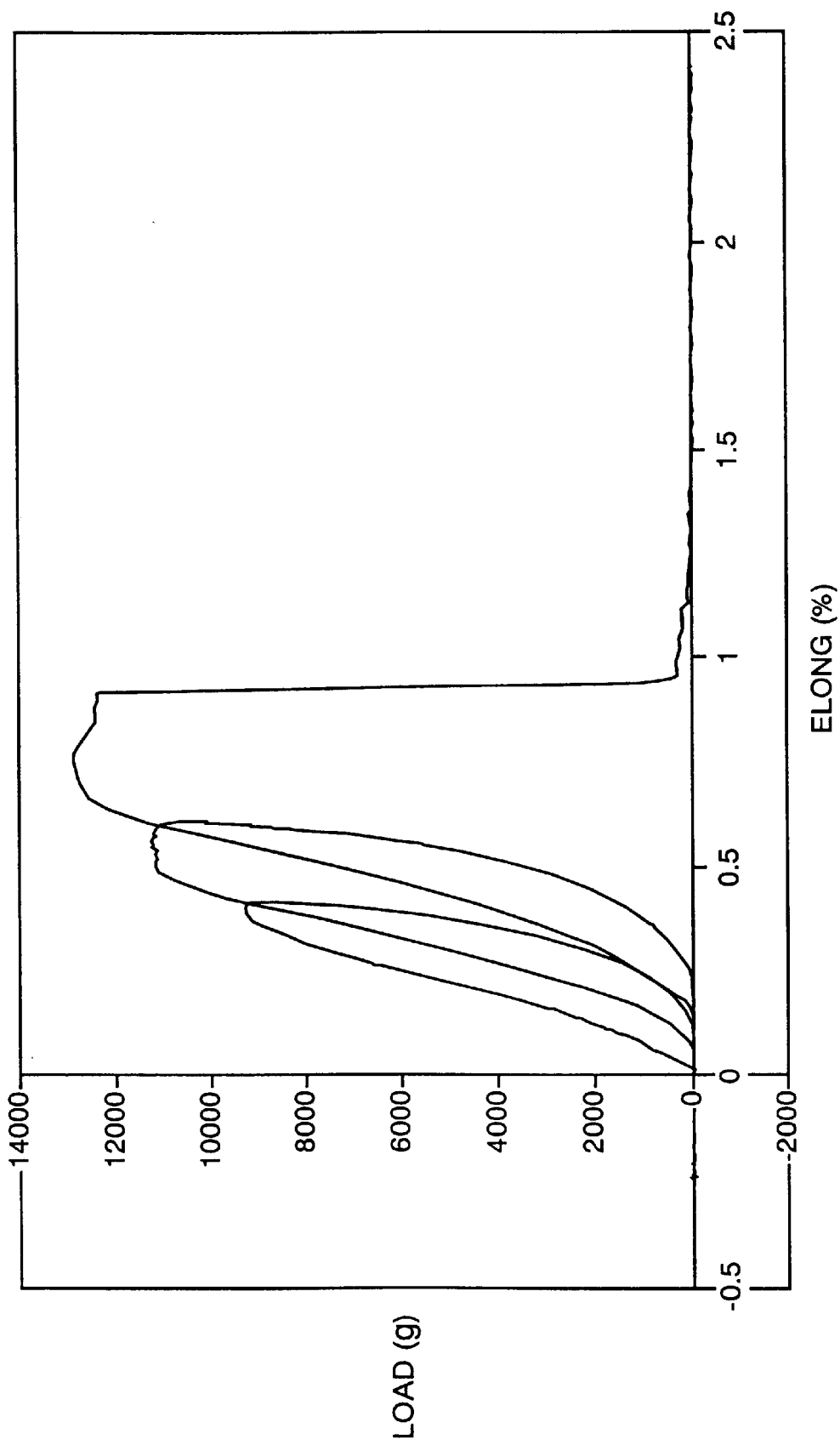
FIGS. 32–34 graphically illustrate results of LD cycling testing done on various samples.
Figure 33:
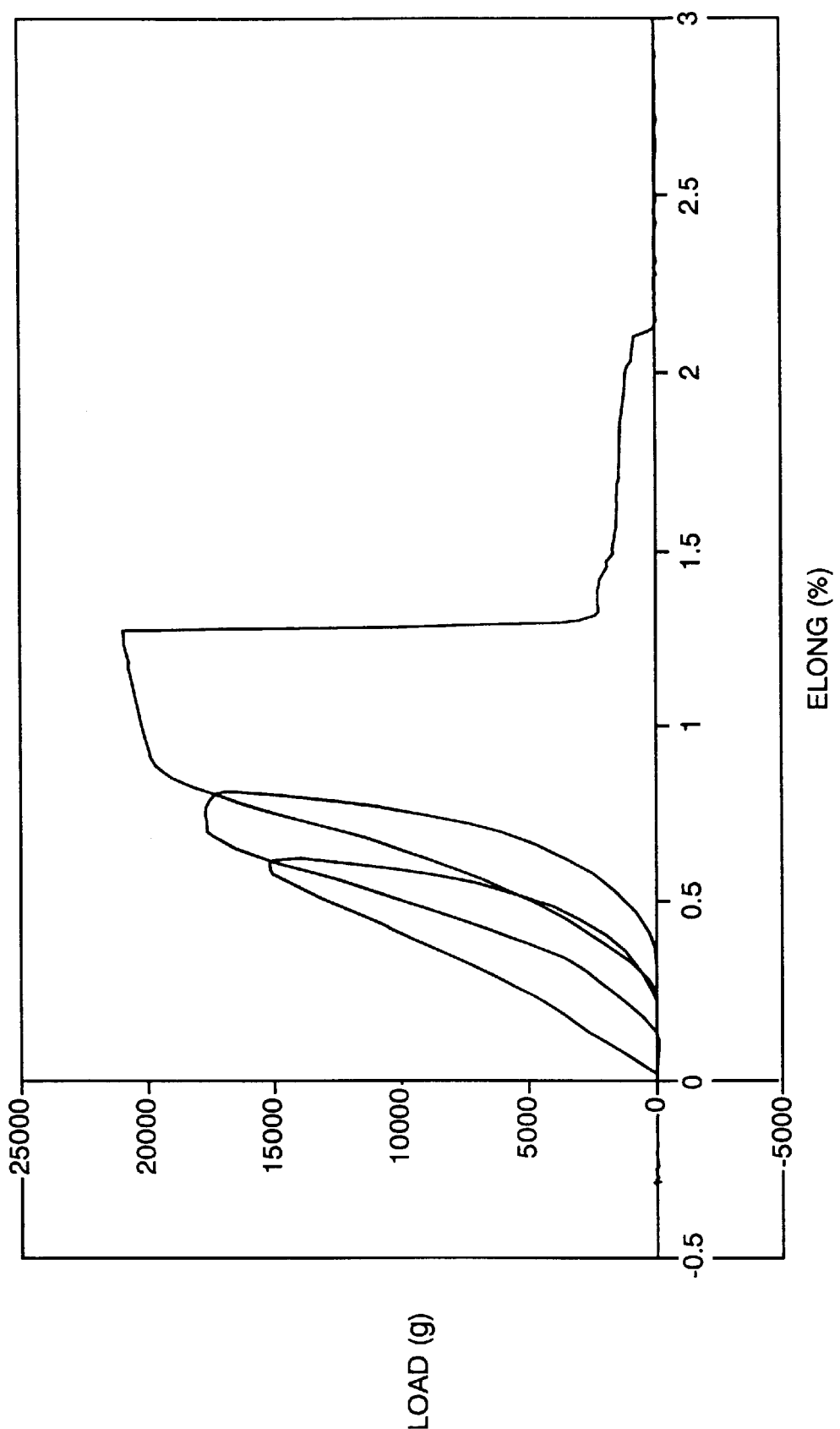
Figure 34:
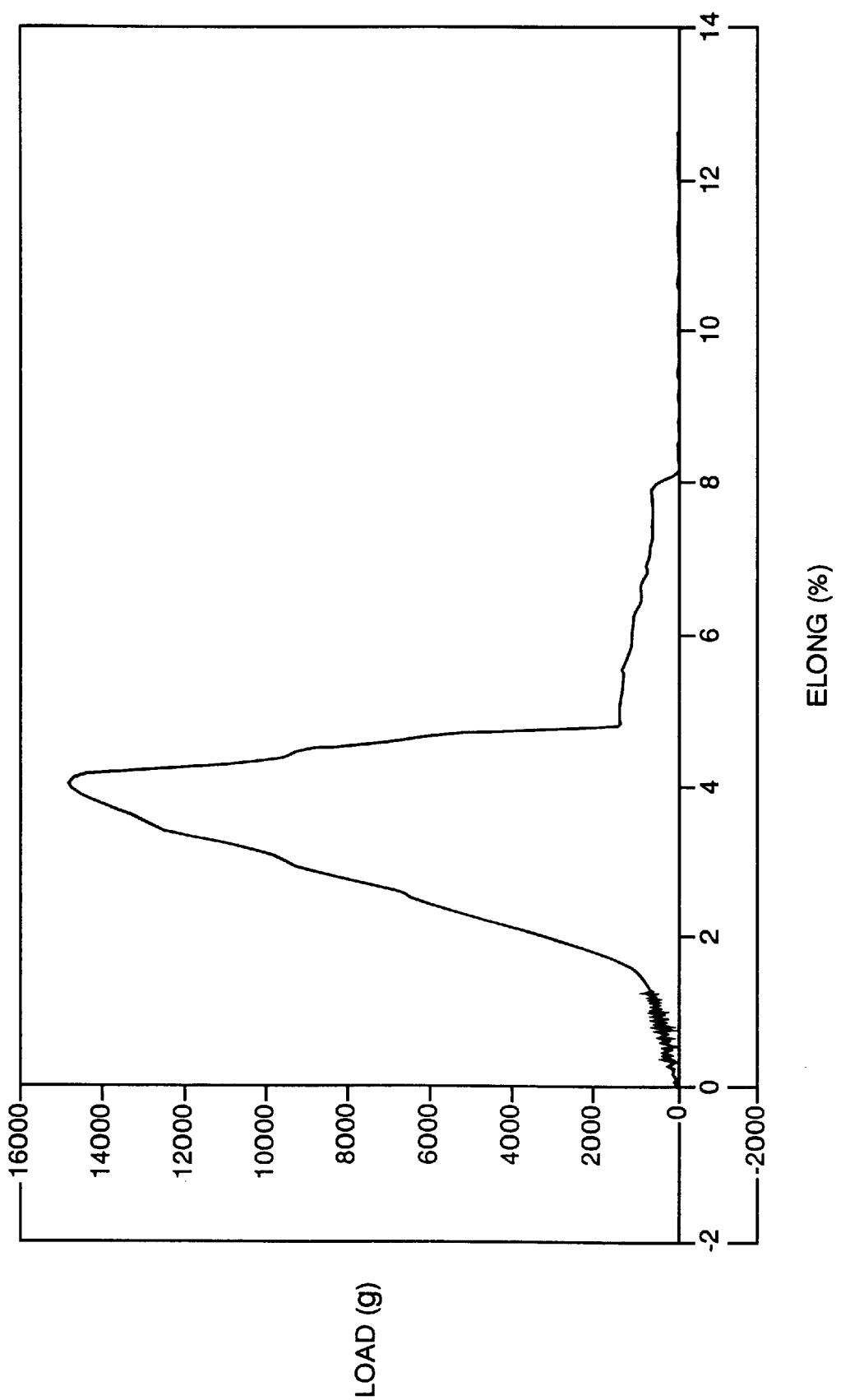
Figure 35:
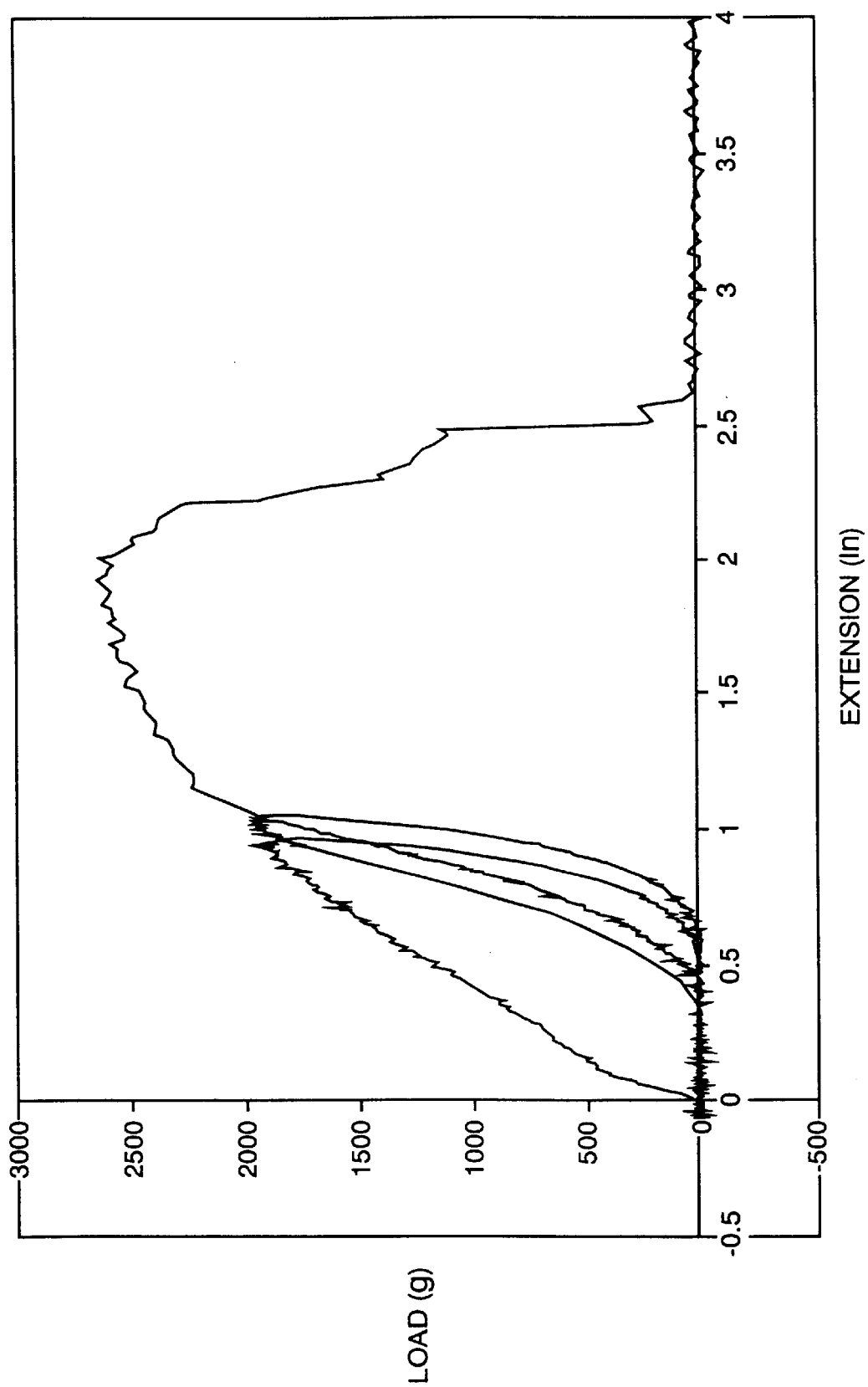
FIGS. 35–37 graphically illustrate results of TD cycling testing done on various samples.
Figure 36:
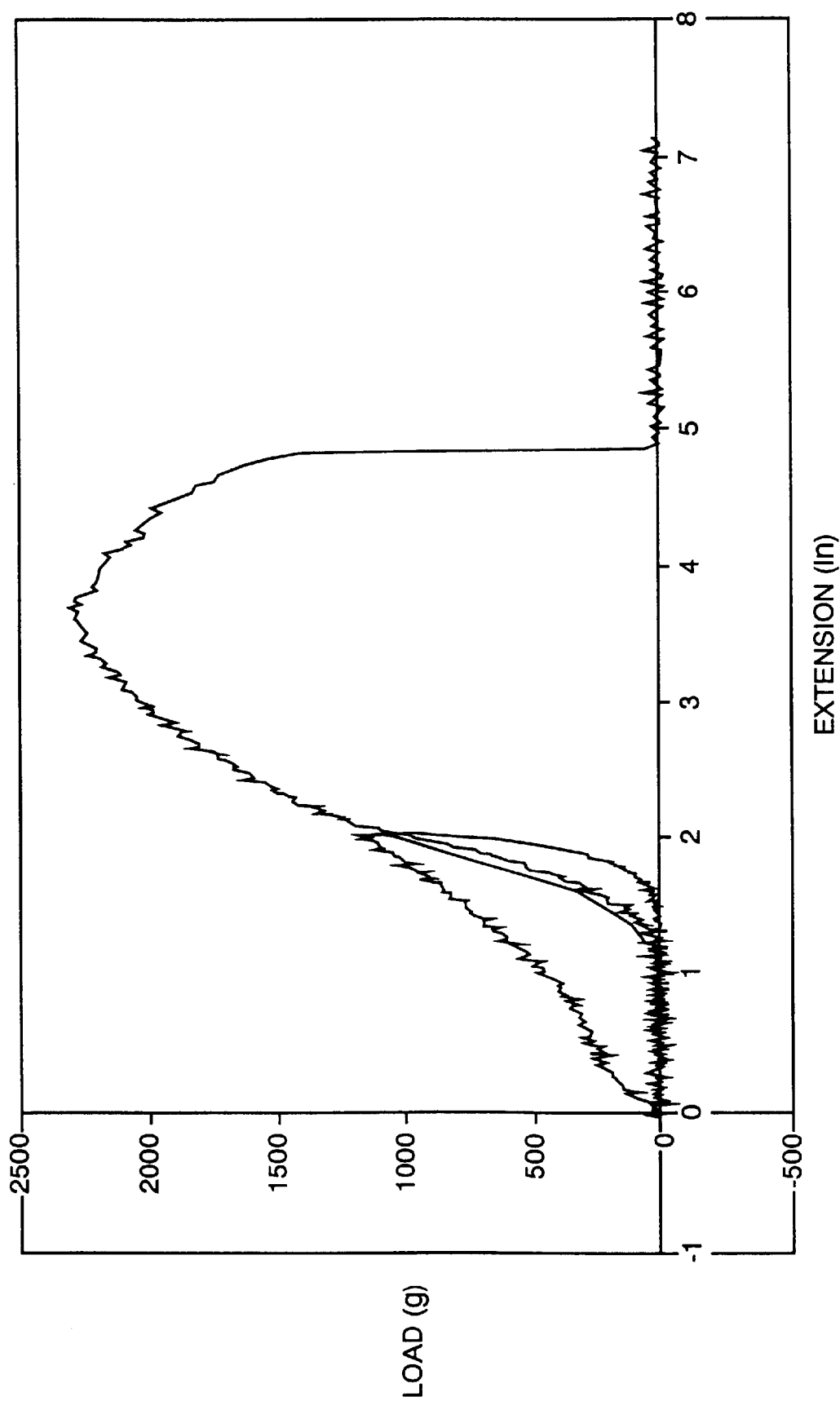
Figure 37:
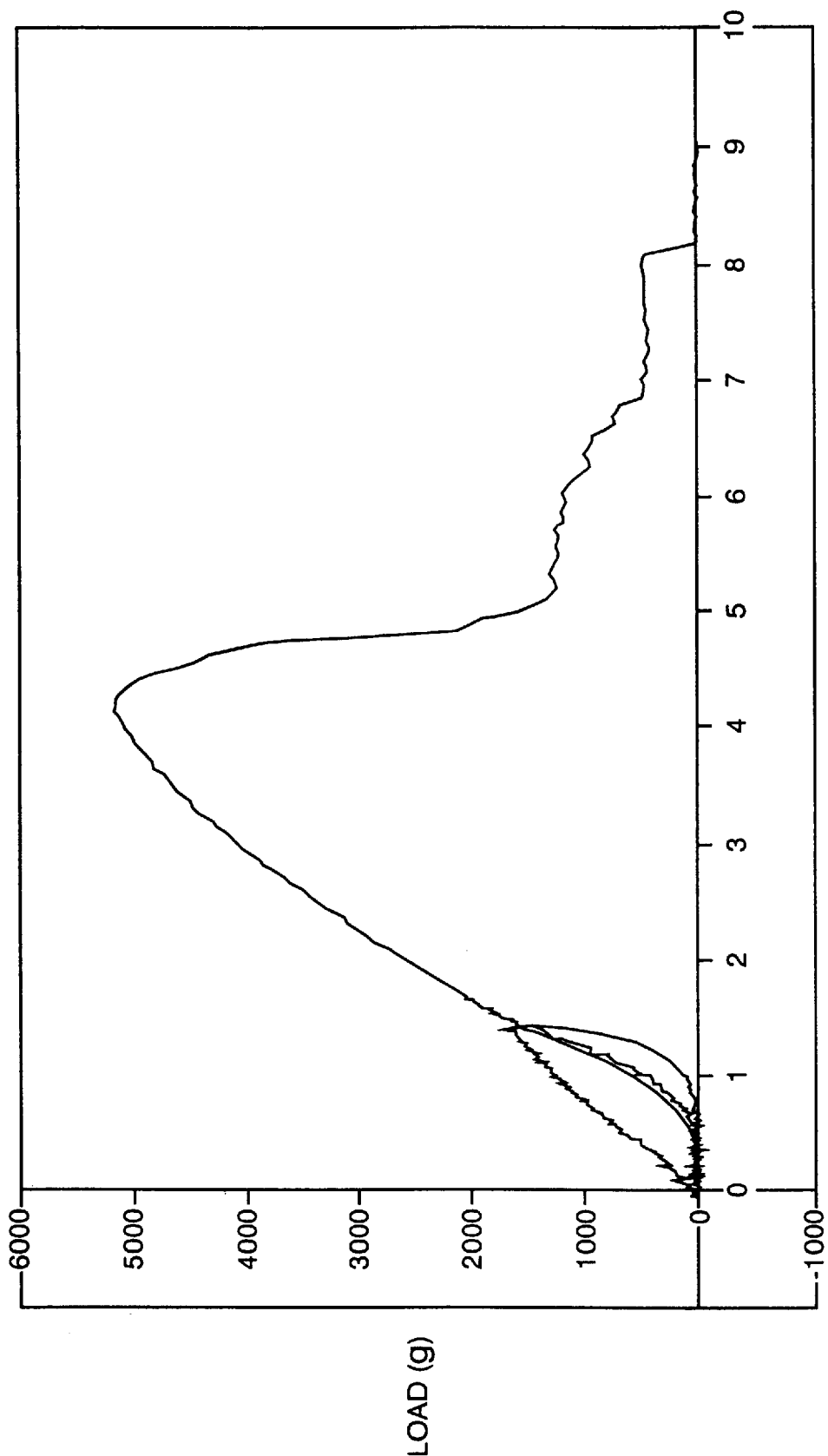

These samples were cycle tested as described above for Example 5 and the results are reported below in Tables 13 and 14. The Samples in Table 13 were cycle tested in the LD which is graphically illustrated in FIGS. 32–34. The Samples in Table 14 were cycle tested in the LD which is graphically illustrated in FIGS. 35–37.

TABLE 13

| | | at 50% of elongation cycled to in grams | | | | | TD Peak | Elong @ |
|---|---|---|---|---|---|---|---|---|
| Sample | % elongation cycled to | First up | Third up | First Down | Second Down | Permanent Set (%) | Load (g) | Peak Load (%) |
| C1 | 21 | 4378 | 476 | 631 | 16 | 29 | 12533 | 43 |
| 6 | 31 | 7088 | 971 | 732 | 7 | 28 | 20536 | 64 |
| 17 | 66 | 339 | 252 | 199 | 18 | 18 | 15437 | 189 |

TABLE 14

| Sample | % elongation cycled to | at 50% of elongation cycled to in grams | | | | Permanent Set (%) | TD Peak Load (g) | Elong @ Peak Load (%) |
| --- | --- | --- | --- | --- | --- | --- | --- | --- |
| | | First up | Third up | First Down | Second Down | | | |
| C1 | 50 | 1027 | 98 | 5 | 6 | 62 | 2400 | 92 |
| 6 | 101 | 420 | 12 | 9 | 6.6 | 76 | 2300 | 194 |
| 17 | 72 | 905 | 107 | 12 | 14 | 58 | 4662 | 177 |

Having thus described the invention in detail, it should be apparent that various modifications can be made in the present invention without departing from the spirit and scope of the following claims.

We claim:

1. A composite material comprising:
   a) at least one first layer of a non-elastic neckable material;
   b) at least one second layer of a non-elastic film attached to said at least one first layer to form a laminate; wherein said laminate is necked in a first dimension to form a necked laminate and wherein said second film layer has striated rugosities in a dimension perpendicular to said first dimension; and
   c) at least one layer of an elastic material attached to said necked laminate.

2. The composite material of claim 1, wherein said material exhibits extension and retraction in at least one dimension and stretch and recovery in at least one dimension.

3. The composite material of claim 2, wherein said striated rugosities comprise trapezoidal, crenellated, or pleated striations.

4. The composite material of claim 2, wherein said means of attaching comprises point bonding, thermal point bonding, adhesive bonding, or sonic welding.

5. The composite material of claim 4, wherein adhesive bonding is used to attached the layers.

6. The composite material of claim 2, wherein said first dimension is defined by a transverse dimension and said perpendicular dimension is defined by a longitudinal dimension.

7. The composite material of claim 2, wherein said material is breathable.

8. The composite material of claim 2, wherein said non-elastic neckable material has a basis weight of from about 0.3 osy (10 gsm) to about 2.7 osy (90 gsm).

9. The composite material of claim 2, wherein said non-elastic neckable material or said non-elastic film comprises a polyolefin.

10. The composite material of claim 2 or 9, wherein said neckable material comprises a spunbond nonwoven material.

11. A conformable composite material for use in a garment comprising:
   a) at least one first layer of a non-elastic neckable material;
   b) at least one second layer of a non-elastic film attached to said at least one first layer to form a laminate; wherein said laminate is necked in a first dimension to form a necked laminate and wherein said second film layer has striated rugosities in a dimension perpendicular to said first dimension; and
   c) at least one layer of an elastic material attached to said necked laminate; wherein a biasing force applied to said first dimension of said material will cause said material to extend, stretch and conform around the body of the user.

12. The conformable composite material of claim 11, wherein said striated rugosities comprise trapezoidal, crenellated, or pleated striations.

13. The conformable composite material of claim 11, wherein said means of attaching comprises thermal point bonding, point bonding, adhesive bonding, or sonic welding.

14. The conformable composite material of claim 13, wherein adhesive bonding is used to attach the layers.

15. The conformable composite material of claim 11, wherein said first dimension is defined by a transverse dimension and said perpendicular dimension is defined by a longitudinal dimension.

16. The conformable composite material of claim 11, wherein said non-elastic neckable material has a basis weight of from about 0.3 osy (10 gsm) to about 2.7 osy (90 gsm).

17. The conformable composite material of claim 11, wherein said composite material is breathable.

18. The conformable composite material of claim 11, wherein said laminate forms at least a portion of a personal care absorbent article.

19. The conformable composite material of claim 11, 17 or 18, wherein said laminate forms at least a portion of an outer cover for a personal care absorbent article.

20. The conformable composite material of claim 11 wherein said composite material contains apertures.

21. The conformable composite material of claim 20 wherein said composite material forms at least a portion of a liner for a personal care absorbent article.

22. The conformable composite material of claim 11, wherein said laminate forms at least a portion of a protective garment.

23. The conformable composite material of claim 11 or 20, wherein said laminate forms at least a portion of a facemask.

24. A breathable, conformable composite material for use in a garment, comprising:
   a) at least one first layer of a non-elastic neckable spunbond material having a basis weight of from about 0.3 osy (10 gsm) to about 0.7 osy (24 gsm);
   b) at least one second layer of a non-elastic film containing from about 20% to about 45% by volume of filler, said second film layer attached to said non-elastic neckable spunbond material to form a laminate; wherein said laminate is necked in a first dimension to about 30% to about 80% of its original width to form a necked laminate, and wherein said film layer has striated rugosities in a dimension perpendicular to said first dimension, such that a biasing force applied to said first dimension of said laminate will cause said necked laminate to extend and conform around the body of the user; and c) at least one layer of a stretched elastic material attached to said necked laminate such that the composite material exhibits stretch and recovery in at least one dimension.

25. The breathable, conformable composite material of claim 24 wherein said composite material exhibits stretch and recovery in multiple dimensions.

* * * * *